(12) United States Patent
Wallace et al.

(10) Patent No.: US 11,154,024 B2
(45) Date of Patent: Oct. 26, 2021

(54) **SINGLE NUCLEOTIDE POLYMORPHISM (SNP) MARKERS FOR *PHASEOLUS VULGARIS* L. AND METHODS OF USE THEREOF IN SELECTION EFFICIENCY WITH BREEDING STRATEGIES**

(71) Applicant: Oregon State University, Corvallis, OR (US)

(72) Inventors: Lyle T. Wallace, Corvallis, OR (US); James R. Myers, Corvallis, OR (US)

( * ) Notice: Subject to any disclaimer, the term of this patent is extended or adjusted under 35 U.S.C. 154(b) by 267 days.

(21) Appl. No.: 16/535,342

(22) Filed: Aug. 8, 2019

(65) Prior Publication Data

US 2020/0008380 A1 Jan. 9, 2020

Related U.S. Application Data

(63) Continuation of application No. 15/837,732, filed on Dec. 11, 2017, now Pat. No. 10,426,112.

(51) Int. Cl.

| | |
|---|---|
| *A01H 5/10* | (2018.01) |
| *C12N 15/82* | (2006.01) |
| *A01H 5/02* | (2018.01) |
| *A01H 1/04* | (2006.01) |
| *C12Q 1/6895* | (2018.01) |
| *A01H 6/54* | (2018.01) |

(52) U.S. Cl.
CPC .................. *A01H 5/02* (2013.01); *A01H 1/04* (2013.01); *A01H 5/10* (2013.01); *A01H 6/545* (2018.05); *C12N 15/8213* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | |
|---|---|---|
| 9,414,553 B2 | 8/2016 | de Haan et al. |
| 2017/0159067 A1 | 6/2017 | Charne et al. |
| 2017/0238493 A1 | 8/2017 | Reuling et al. |

FOREIGN PATENT DOCUMENTS

| | | |
|---|---|---|
| WO | 2016/049531 | 3/2016 |

OTHER PUBLICATIONS

Results from BLAST® search for sequences producing significant alignments relative to SEQ ID No. 9 in the GenBank, obtained on Jun. 29, 2021.*
Aghoram et al., "A mutation in a 3-keto-acyl-ACP synthase II gene is associated with elevated palmitic acid levels in soybean seeds", Crop Science, Crop Science Society of America, Oct. 2, 2006, 46:2453-2459.
Ariyarathne et al., "Molecular mapping of disease resistance genes for halo blight, common bacterial blight, and bean common mosaic virus in a segregating population of common bean", J. Amer. Soc. Hort. Sci. 1999, 124(6): 654-662.
Baldina et al., "Metabolite Profiling of Italian Tomato Landraces with Different Fruit Types", Frontiers in Plant Science, May 19, 2016, 1-13, 7:664.
Baldwin et al., "Flavor Trivia and Tomato Aroma: Biochemistry and Possible Mechanisms for Control of Important Aroma Components", HortScience, Oct. 2000, 35(6):1013-1022.
Barra et al., "Chemical analysis of french beans (*Phaseolus vulgaris* L.) by headspace solid phase microextraction (HS-SPME) and simultaneous distillation/extraction (SDE)", ScienceDirect, Food Chemistry, 2007, 101:1279-1284.
Bassett, "A Revised Linkage Map of Common Bean", HortScience, Jul. 1991, 26(7):834-836.
Bassi et al., "Linkage and mapping of quantitative trait loci associated with angular leafspot and powdery mildew resistance in common beans", Genetics and Molecular Biology, Brazil, 2017, 40(1):109-122.
Bauchet et al., "Identification of major loci and genomic regions controlling acid and volatile content in tomato fruit: implications for flavor improvement" New Phytologist, 2017, 215: 624-641.
Baysal et al., "Lipoxygenase in fruits and vegetables: A review", ScienceDirect, Enzyme and Microbial Technology, 2007, 40: 491-496.
Beebe et al., "Quantitative Trait Loci for Root Architecture Traits Correlated with Phosphorus Acquisition in Common Bean", Crop Science, Crop Science Society of America, Jan. 24, 2006, 46:413:423.
Bhakta et al., "A predictive model for time-to-flowering in the common bean based on QTL and environmental variables", Genes, Genomes, Genetics, Dec. 2017, 7:3901-3912.
Birkett et al., "New roles for cis-jasmone as an insect semiochemical and in plant defense", PNAS, Aug. 1, 2000, 97(16): 9329-9334.
Bojanowski et al., "Retronasal Perception of Odors", Physiology & Behavior, Elsevier Inc., 2012, 107:484-487.
Bradbury et al., "TASSEL:software for association mapping of complex traits in diverse samples" Bioinformatics, 2007, 23:2633-2635.
Buttery et al., "Fresh Tomato Aroma Volatiles: A Quantitative Study", J. Agric. Food Chem., American Chemical Society, 1987, 35: 540-544.

(Continued)

*Primary Examiner* — Bratislav Stankovic
(74) *Attorney, Agent, or Firm* — Stradley Ronon Stevens & Young, LLP

(57) ABSTRACT

The invention provides processes for marker assisted selection of common beans expressing volatile compounds that provide flavor traits associated with single nucleotide polymorphisms (SNPs) and/or sequences flanking SNPs, as well as allele-specific oligo sequence primers configured to anneal to related SNPs and to report the presence or absence of SNPs with fluorescent signals using a PCR assay, a KASP assay (i.e., modified PCR assay), or other molecular marker assay, e.g., SSR, capable of identifying the presence or absence of SNPs and/or portions of flanking sequences of the SNPs, all of which enhances selection efficiency in common bean breeding strategies.

6 Claims, 11 Drawing Sheets
(9 of 11 Drawing Sheet(s) Filed in Color)
Specification includes a Sequence Listing.

(56) References Cited

OTHER PUBLICATIONS

Cadic et al., "Combined linkage and association mapping of flowering time in Sunflower (*Helianthus annuus* L.)", Theor. Appl. Genet., 2013, 126:1337-1356.

Chacon et al., "Domestication patterns in common bean (*Phaseolus vulgaris* L.) and the origin of the Mesoamerican and Andean cultivated races" Theoretical and Applied Genetics, 2005, 110(3):432-444.

Cichy et al., "Genetic diversity and genome wide association analysis of cooking time in dry bean (*Phaseolus vulgaris* L.)" Theor. Appl. Genet, 2015, 128:1555-1567.

Cichy et al., Abstract of "QTL Analysis of canning quality and color retention in black beans (*Phaseolus vulgaris* L.)" Molecular Breeding 33(1): 139-154.

Croft et al., "Volatile Products of the Lipoxygenase Pathway Evolved from *Phaseolus vulgaris* (L.) Leaves Inoculated with Pseudomonas syringae pv phaseolicola" Plant Physiol, 1993, 101:13-24.

Diaz et al., "Phenotypic evaluation and QTL analysis of yield and symbiotic nitrogen fixation in a common bean population grown with two levels of phosphorus supply", Mol. Breeding, 2017, 37:76.

Dijksterhuis et al., "Multivariate data analysis in sensory and consumer science: an overview of developments", Trends in Food Science & Technology, Jun. 1995, 6: 206-211.

Drewnowski, "Taste Preferences and Food Intake", Annu. Rev. Nutr. 1997, 17:237-53.

Dubey et al., "An overview of the non-mevalonate pathway for terpenoid biosynthesis in plants", J. Biosci. Sep. 2003, 28: 637-646.

Dudareva et al., "Biosynthesis, function and metabolic engineering of plant volatile organic compounds", New Phytologist, 2013, 198:16-32.

Ender et al., "Identification of QTL Associated with White Mold Resistance in Common Bean", Crop Sci., Crop Science Society of America, Oct. 27, 2005, 45:2482-2490.

Fardo et al. "On family-based genome-wide association studies with large pedigrees: observations and recommendations", BMC Proceedings, 2014, 8(Suppl 1):S26.

Freyre et al., "Towards an integrated linkage map of common bean. 4. development of a core linkage map and alignment of RFLP maps" Theor. Appl. Genet., 1998, 97:847-856.

Gao et al., "Avoiding the high Bonferroni penalty in genome-wide association studies", NIH Public Access, Author Manuscript, Genet. Epidemiol, Jan. 2010, 34(1): 100-105, 1-12.

Gaut, "The complex domestication history of the common bean", Nature Genetics, Jul. 2014, 46(7): 663-664.

Gepts, "Origin and Evolution of Common Bean: Past Events and Recent Trends", HortScience, Dec. 1998, 33(7): 1124-1130.

Goh et al., "Effects of normalization on quantitative traits in association test", BMC Bioinformatics, Dec. 14, 2009, 10(415): 1-8.

Gunaseelan et al., "Linalool prevents oxidative stress activated protein kinases in single UVB-exposed human skin cells", Plos One, May 3, 2017, 12(5): e0176699, 1-20.

Hagerty et al., "Mapping Fusarium solani and Aphanomyces euteiches Root Rot Resistance and Root Architecture Quantitative Trait Loci in Common Bean", Crop Sci., Crop Science, Sep.-Oct. 2015, 55:1969-1977.

Hart et al., "Genotyping-by-Sequencing Enabled Mapping and Marker Development for the By-2 Potyvirus Resistance Allele in Common Bean", The Plant Genome, Mar. 2015, 8(1): 1-14.

Heil et al., "Within-plant signaling by volatiles leads to induction and priming of an indirect plant defense in nature", PNAS, Mar. 27, 2007, 104(13): 5467-5472.

Hinterholzer et al., "Identification of the key odorants in raw French beans and changes during cooking", Z Lebensm Unters Forsch A, 1998, 207: 219-222.

Holmans, "Non-parametric Linkage" in Handbook of Statistical Genetics, John Wiley & Sons, Ltd., West Sussex, England, 2007, 3(1): 1168-1189.

Huang et al., "Natural Variations and Genome-Wide Association Studies in Crop Plants" Annu. Rev. Plant Biol., 2014, 65:531-551.

Jansen et al., "High Resolution of Quantitative Traits Into Multiple Loci via Interval Mapping", Genetics, Apr. 1994, 136:1447-1455.

Jansen, "Controlling the Type I and Type II Errors in Mapping Quantitative Trait Loci", Genetics, Nov. 1994, 138:871-881.

Jansen, "Interval Mapping of Multiple Quantitative Trait Loci", Genetics, Sep. 1993, 135: 205-211.

Jansen, "Quantitative Trait Loci in Inbred Lines", in Handbook of Statistical Genetics, John Wiley & Sons Ltd., West Sussex, England, 2007, 3(1):589-622.

Johnson et al., "Accounting for multiple comparisons in a genome-wide association study (GWAS)", BMC Genomics, 2010, 11:724, 1-6.

Jombart, "adegenet: an R package for the multivariate analysis of genetic markers", Bioinformatics, Oxford University Press, 2008, 24(11):1403-1405.

Jung et al., Confirmation of QTL Associated with Common Bacterial Blight Resistance in Four Different Genetic Backgrounds in Common Bean. Crop Sci., Sep. 1999, 39:1448-1455.

Kader, "Flavor quality of fruits and vegetables", J. Sci. Food Agric., 2008, 88:1863-1868.

Kalisz et al., "Short review: Variation and constraint in plant evolution and development", Heredity, 2008, 100:171-177.

Kamfwa et al., "Genome-Wide Association Analysis of Symbiotic Nitrogen Fixation in Common Bean", Theor. Appl. Genet., 2015, 128: 1999-2017.

Kamfwa et al., "Genome-Wide Association Study of Agronomic Traits in Common Bean" The Plant Genome, Jul. 10, 2015, 8(2): 1-12.

Keller et al., "Fine-Mapping of a major QTL controlling angular leaf spot resistance in common bean (*Phaseolus vulgaris* L.)", Theor. Appl. Genet., 2015, 128:813-826.

Kelly, J.D. 1988. The impact of the Dwarf Lethal (DL) genes on bean breeding programs at MSU. Annu. Rept. Bean Improv. Coop. 31:192-193.

Klee et al., "Genetic challenges of flavor improvement in tomato", Apr. 2013, 29(4): 257-262.

Klee, "Improving the flavor of fresh fruits: genomics, biochemistry, and biotechnology", New Phytologist, 2010, 187:44-56.

Koinange, E.M.K., Singh, S.P., Gepts, P. 1996. Genetic control of the domestication syndrome in common bean. Crop Sci. 36(4): 1037-1045.

Kolkman et al., "QTL Conferring Resistance and Avoidance to White Mold in Common Bean", Crop Sci., 2003, 43:539-548.

Korte et al., "The advantages and limitations of trait analysis with GWAS: a review", Plant Methods, 2013, 9(29): 1-9.

Kunishima et al., "Identification of (Z)-3:(E)-2-hexenal isomerases essential to the production of the leaf aldehyde in plants", J. Biol. Chem., JBC Papers in Press., M116.726687, Apr. 29, 2016, 1-28.

Kuznetsova et al., "lmerTest Package: Tests in Linear Mixed Effects Models", Journal of Statistical Software, Dec. 2017, 82(13):1-26.

Laird et al., "The Fundamentals of Modern Statistical Genetics", Springer Science + Business Media, Dordrecht, Netherlands, 75, 91-92.

Lewinsohn et al., "Enhanced Levels of the Aroma and Flavor Compound S-Linalool by Metabolic Engineering of the Terpenoid Pathway in Tomato Fruits", Plant Physiology, Nov. 2001, 127:1256-1265.

Lim et al., "The role of congruency in taste—odor interactions", Food Quality and Preference, 2014, 34:5-13.

Liu et al., "Iterative usage of fixed and random effect models for powerful and efficient genome-wide association studies", PLoS Genetics, Feb. 1, 2016, 12:1-24.

Loutfi et al., "Electronic noses for food quality: a review" Journal of Food Engineering, 2015, 144: 103-111.

Lumen et al., "Formation of volatile flavor compounds in green beans from linoleic and linolenic acids", Journal of Food Science, 1978, 43:698-708.

MacLeod et al., "Flavor Volatiles of Some Cooked Vegetables", Journal of Food Science, 1970, 35:734-738.

Mamidi et al., "Genome-wide association studies identifies seven major regions responsible for iron deficiency chlorosis in soybean (*Glycine max*)", PLoS One, Sep. 2014, 9(9): e107469, 1-13.

(56) References Cited

OTHER PUBLICATIONS

Mamidi et al., "Investigation of the domestication of common bean (Phaseolus vulgaris) using multilocus sequence data" Functional Plant Biology, CSIRO Publishing, 2011, 38:953-967.

Matsui et al., "Green leaf volatiles: Hydroperoxide lyase pathway of oxylipin metabolism", Current Opinion in Plant Biology, 2006, 9:274-280.

Mayer et al., "Studies on the Aroma of Five Fresh Tomato Cultivars and the Precursors of cis- and trans-4,5-Epoxy-(E)-2-Decenals and Methional", Journal of Agricultural and Food Chemistry, 2008, 56:3749-3757.

Miklas et al., "Inheritance and QTI Analysis of Field Resistance to Ashy Stem Blight in Common Bean", Crop Science, Jul.-Aug. 1998, 38(4): 916-921.

Miklas et al., "Selective Mapping of QTL Conditioning Disease Resistance in Common Bean", Crop Sci., 1996, 36(5): 1344-1351.

Morton et al., "Sequential Tests for the Detection of Linkage", American Journal of Human Genetics, 1955, 7(3): 277-318.

Mosciano, G. 1991a. Organoleptic characteristics of flavor materials. Perfumer & Flavorist Magazine 16:49-54.

Mosciano, G. 1991b. Organoleptic characteristics of flavor materials. Perfumer & Flavorist Magazine 16:79-81.

Mosciano, G. 1993a. Organoleptic characteristics of flavor materials. Perfumer & Flavorist Magazine 18:38-41.

Mosciano, G. 1993b. Organoleptic characteristics of flavor materials. Perfumer & Flavorist Magazine 18:33-35.

Mosciano, G. 1997. Organoleptic characteristics of flavor materials. Perfumer & Flavorist Magazine 22:41-75.

Mosciano, G. 1998. Organoleptic characteristics of flavor materials. Perfumer & Flavorist Magazine 23:33-49.

Mosciano, G. 2007. Organoleptic characteristics of flavor materials. Perfumer & Flavorist Magazine 32:54-56.

Moyroud et al., "Prediction of Regulatory Interactions from Genome Sequences Using a Biophysical Model for the *Arabidopsis* LEAFY Transcription Factor", The Plant Cell, 2011, 23:1293-1306.

Mukeshimana et al., "Quantitative Trait Loci Associated with Drought Tolerance in Common Bean", Crop Science, Mar. 21, 2014, 54:923-938.

Myers et al., "Improvement of Snap Bean", in: Common Bean Improvement in the Twenty-First Century, Kluwer Academic Publishers, Dordrecht, The Netherlands, 1999, 289-329.

Myles et al., "Association Mapping: Critical Considerations Shift from Genotyping to Experimental Design", The Plant Cell, Aug. 2009, 21: 2194-2202.

Noble et al., "Use of Multivariate Statistics in Understanding Wine Flavor", Food Reviews International, 2002, 18(1): 1-21.

Noordermeer et al.,"Fatty Acid Hydroperoxide Lyase: A Plant Cytochrome P450 Enzyme Involved in Wound Healing and Pest Resistance", Chembiochem, 2001, 2:494-504.

Nyholt et al., "All LODs Are Not Created Equal", American Journal of Human Genetics, 2000, 67:282-288.

Orin, "Garden Beans Offer Year-Round Source of Great Flavor, Nutrition", UC Santa Cruz for the Gardener Series, Mar. 12, 2008, 1-6, www.escholarship.org/uc/item/5c20h3qs.

Park et al., "Mapping of QTL for Seed Size and Shape Traits in Common Bean", Journal of the American Society for Horticultural Science, 2000, 125(4):466-475.

Perseguini et al., "Genome-Wide Association Studies of Anthracnose and Angular Leaf Spot Resistance in Common Bean (*Phaseolus vulgaris* L.)", Plos One, Mar. 1, 2016, 11(3): e0150506, 1-19.

Pfeiffer et al., "Taste—Aroma Interactions in a Ternary System: A Model of Fruitiness Perception in Sucrose/Acid Solutions", Perception & Psychophysics, 2006, 68(2):216-227.

Porras-Hurtado et al., "An overview of Structure: applications, parameter settings, and supporting software", Frontiers in Genetics, May 29, 2013, 4(98):1-13.

Quiros et al., "Comparison of volatile components in raw and cooked green beans by GC-MS using dynamic headspace sampling and microwave desorption", European Food Research and Technology, 2000, 210:226-230.

Rambla et al., "The expanded tomato fruit volatile landscape", Journal of Experimental Botany, Apr. 1, 2014, 65(16):4613-4623.

Rodriguez et al., "Biosynthesis of carotenoids in carrot: An underground story comes to light", Archives of Biochemistry and Biophysics, 2013, 539:110-116.

Rubatzky et al., "World vegetables: principles, production, and nutritive values", Aspen Publishers, Inc., Gaithersburg, Maryland, 1996, 2nd ed. pp. 488-498.

Schmutz et al., "A reference genome for common bean and genome-wide analysis of dual domestications", Nature Genetics, Jun. 8, 2014, 46:707-713.

Singh et al., "Inheritance of Crippled Trifoliolate Leaves Occurring in Interracial Crosses of Common Bean and its Relationship with Hybrid Dwarfism", Journal of Heredity, 1996, 87(6):464-469.

Singh et al., "Races of common bean (Phaseolus vulgaris, Fabaceae)", 1991, Economic Botany 45(3):379-396.

Stevens et al., "Inheritance of oct-1en-3-ol and linalool in canned snap beans (*Phaseolus vulgaris* L.)", Proceedings of the American Society for Horticultural Science, 1967, 91:274-285.

Stevens et al., "Volatile components of canned snap beans (*Phaseolus vulgaris* L.)", Proceedings of the American Society for horticultural Science, 1967, 91:833-845.

Tieman et al., "A chemical genetic roadmap to improved tomato flavor", Plant Science, 2017, 355:391-394.

Tieman et al., "The Chemical Interactions Underlying Tomato Flavor Preferences", Current Biology, Jun. 5, 2012, 22(11):1035-9.

Toya et al., "Inheritance of 1-octen3-ol concentration in frozen pods of bush snap beans, *Phaseolus vulgaris* L.", Journal of the American Society for Horticultural Science, 1976, 101:196-198.

Toya et al., "The Influence of Processing and Maturity on Volatile Components in Bush Snap Beans, *Phaseolus vulgaris* L.", Journal of the American Society for Horticultural Science, 1974, 99(6):493. 497.

United States Department of Agriculture—National Agricultural Statistics Service (NASS), Jul. 12, 2017, Press Release. www.nass.usda.gov/Statistics _by_State /Washington/Publications/Current_News_Release/2017/Veg_ann.pdf.

United States Department of Agriculture, Agricultural Research Service, Nutrient Data Laboratory. USDA National Nutrient Database for Standard Reference, Release 28. Version Current: Sep. 2015, slightly revised May 2016. www.ars.usda.gov/northeast-area/beltsville-md/beltsville-human-nutrition-research-center/nutrient-data-laboratory/docs/sr28-download-files/.

Utto et al., "Hexanal reduces infection of tomatoes by Botrytis cinerea whilst maintaining quality", 2008, 47(3): 434-437.

Valdisser et al., "In-depth genome characterization of a Brazilian common bean core collection using DArTseq high-density SNP genotyping", BMC Genomics, 2017, 18:423.

Valsova et al., "Genome and transcriptome analysis of the Meso-american common bean and the role of gene duplications in establishing tissue and temporal specialization of genes", Genome Biology, 2016, 17:32.

Van Ruth et al., "Volatile compounds of rehydrated french beans, bell peppers and leeks. Part 1. Flavour release in the mouth and in three mouth model systems", Food Chemistry, 1995, 53:15-22.

Van Ruth et al., "Volatile compounds of rehydrated french beans, bell peppers and leeks. Part II. Gas chromatography/sniffing port analysis and sensory evaluation", Food Chemistry, 1995, 54:1-7.

Viteri et al., "A New Common Bacterial Blight Resistance QTL in VAX 1 Common Bean and Interaction of the New QTL, SAP6, and SU91 with Bacterial Strains", Crop Science, Apr. 28, 2015, 54:1598-1608.

Vogt, "Phenylpropanoid Biosynthesis", Molecular Plant, 2010, 3:2-20.

Wallace et al., "Centers of domestication for Chinese, Spanish, and BeanCAP snap bean populations", Annual Report Bean Improvement Cooperation, 2017, 60:147.

Zeng, "Precision Mapping of Quantitative Trait Loci", Genetics Society of America, 1993, 136:1457-1468.

Zhang et al., "Genome-Wide Association Mapping for Tomato Volatiles Positively Contributing to Tomato Flavor" Frontiers in Plant Science, Nov. 27, 2016, doi: 10.3389/fpls.2015.01042., 6(1042): 1-13.

(56) References Cited

OTHER PUBLICATIONS

Zhao et al., "Association Mapping of Main Tomato Fruit Sugars and Organic Acids", Frontiers in Plant Science, Aug. 26, 2016, doi: 10.3389/fpls.2016.01286, 7(1286): 1-11.
Zhu et al., "Novel Alleles for Black and Gray Seed Color Genes in Common Bean" Crop Science, Jun. 16, 2017, 57:1603-1610.
Zhu et al., "Status and Prospects of Association Mapping in Plants" The Plant Genome, Jul. 2008, 1(1):5-20.

\* cited by examiner

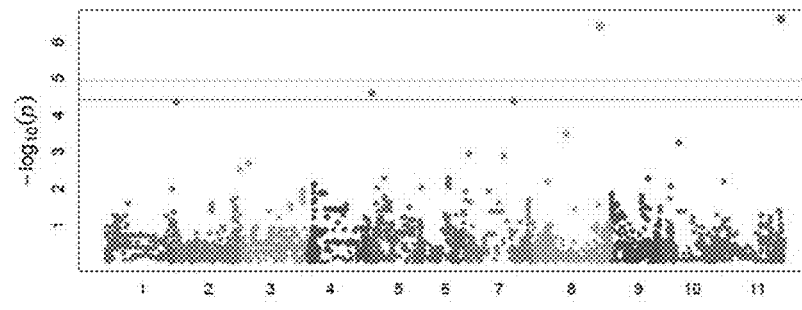 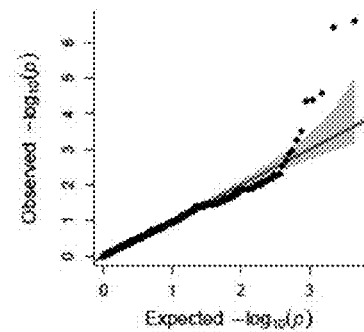
Figure 6A  Figure 6B
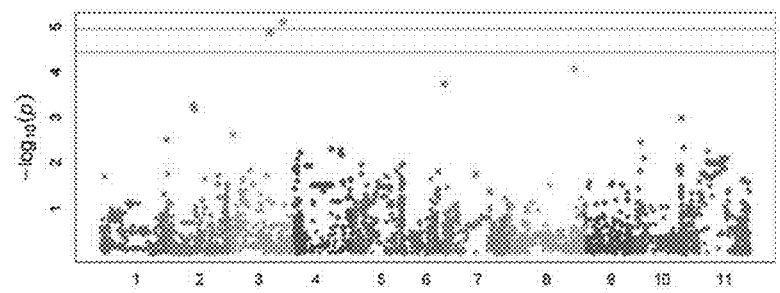 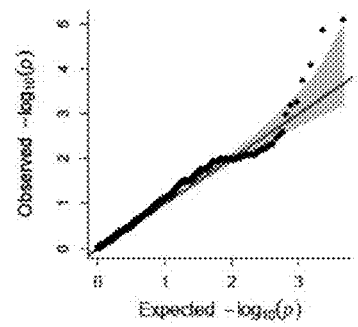
Figure 7A  Figure 7B
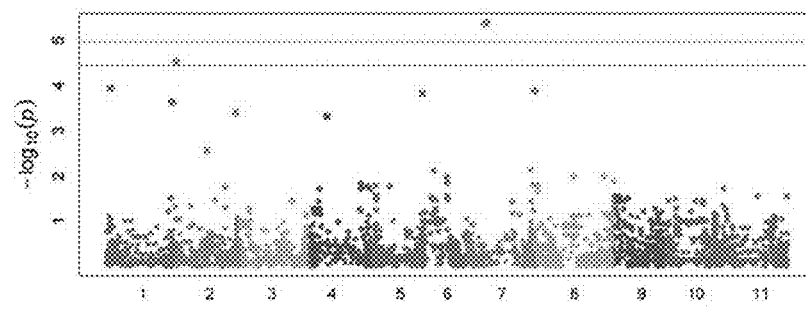 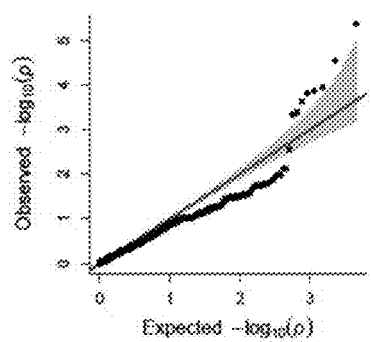
Figure 8A  Figure 8B

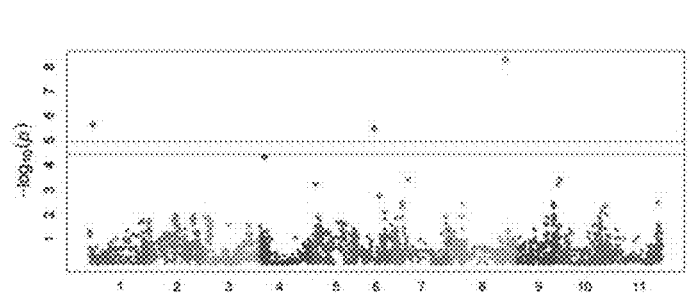
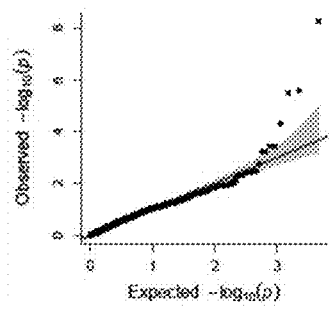
Figure 9A          Figure 9B
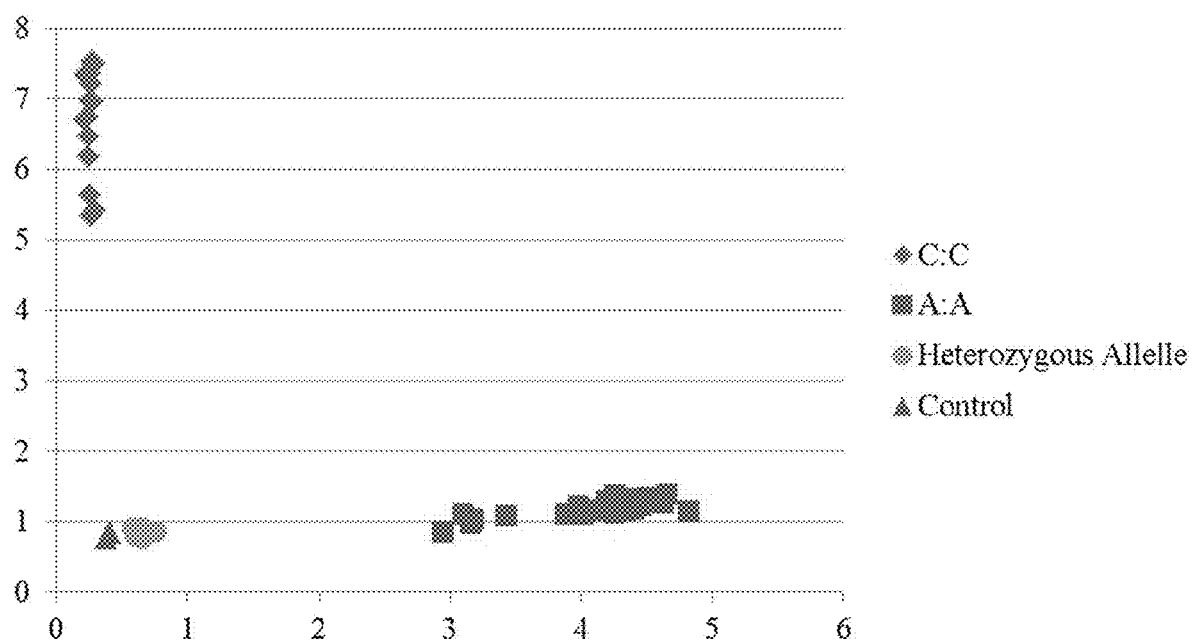
Figure 10

SEQUENCE LISTING

```
<160> NUMBER OF SEQ ID NOS: 91

<210> SEQ ID NO 1
<211> LENGTH: 32
<212> TYPE: DNA
<213> ORGANISM: Phaseolus vulgaris
<220> FEATURE:
<221> NAME/KEY: misc_feature
<222> LOCATION: (32)..(32)
<223> OTHER INFORMATION: n is t or g

<400> SEQUENCE: 1
ttctactttg aatattaaga ttcatgtgca tn                                     32

<210> SEQ ID NO 2
<211> LENGTH: 33
<212> TYPE: DNA
<213> ORGANISM: Phaseolus vulgaris
<220> FEATURE:
<221> NAME/KEY: misc_feature
<222> LOCATION: (33)..(33)
<223> OTHER INFORMATION: n is g or a

<400> SEQUENCE: 2
gtaatcatat tcaaataagt tttatttatt can                                    33

<210> SEQ ID NO 3
<211> LENGTH: 26
<212> TYPE: DNA
<213> ORGANISM: Phaseolus vulgaris
<220> FEATURE:
<221> NAME/KEY: misc_feature
<222> LOCATION: (26)..(26)
<223> OTHER INFORMATION: n is a or g

<400> SEQUENCE: 3
gtaagatgac cttctgaagg aactgn                                            26

<210> SEQ ID NO 4
<211> LENGTH: 28
<212> TYPE: DNA
<213> ORGANISM: Phaseolus vulgaris
<220> FEATURE:
```

```
<221> NAME/KEY: misc_feature
<222> LOCATION: (28)..(28)
<223> OTHER INFORMATION: n is t or c

<400> SEQUENCE: 4
ctatttacag agcataagtg gattcttn                                            28

<210> SEQ ID NO 5
<211> LENGTH: 27
<212> TYPE: DNA
<213> ORGANISM: Phaseolus vulgaris
<220> FEATURE:
<221> NAME/KEY: misc_feature
<222> LOCATION: (27)..(27)
<223> OTHER INFORMATION: n is c or a

<400> SEQUENCE: 5
gaacatagat cgttaagcaa ctatgtn                                             27

<210> SEQ ID NO 6
<211> LENGTH: 32
<212> TYPE: DNA
<213> ORGANISM: Phaseolus vulgaris
<220> FEATURE:
<221> NAME/KEY: misc_feature
<222> LOCATION: (32)..(32)
<223> OTHER INFORMATION: n is t or g

<400> SEQUENCE: 6
tgatctttat ctatttcctt ttaagacaac an                                       32

<210> SEQ ID NO 7
<211> LENGTH: 30
<212> TYPE: DNA
<213> ORGANISM: Phaseolus vulgaris
<220> FEATURE:
<221> NAME/KEY: misc_feature
<222> LOCATION: (30)..(30)
<223> OTHER INFORMATION: n is g or t

<400> SEQUENCE: 7
aggttttgat gaaaatatgc ttattgatgn                                          30

<210> SEQ ID NO 8
<211> LENGTH: 29
<212> TYPE: DNA
<213> ORGANISM: Phaseolus vulgaris
<220> FEATURE:
<221> NAME/KEY: misc_feature
<222> LOCATION: (29)..(29)
<223> OTHER INFORMATION: n is g or a

<400> SEQUENCE: 8
gttttctaag actatgttat tcttgagcn                                           29

<210> SEQ ID NO 9
<211> LENGTH: 24
<212> TYPE: DNA
<213> ORGANISM: Phaseolus vulgaris
<220> FEATURE:
<221> NAME/KEY: misc_feature
<222> LOCATION: (24)..(24)
<223> OTHER INFORMATION: n is a or g

<400> SEQUENCE: 9
actcactgct cacttcagct actn                                                24
```

-continued

```
<210> SEQ ID NO 10
<211> LENGTH: 23
<212> TYPE: DNA
<213> ORGANISM: Phaseolus vulgaris
<220> FEATURE:
<221> NAME/KEY: misc_feature
<222> LOCATION: (23)..(23)
<223> OTHER INFORMATION: n is a or g

<400> SEQUENCE: 10
agattctcta actcgtgcgt acn                                              23

<210> SEQ ID NO 11
<211> LENGTH: 29
<212> TYPE: DNA
<213> ORGANISM: Phaseolus vulgaris
<220> FEATURE:
<221> NAME/KEY: misc_feature
<222> LOCATION: (29)..(29)
<223> OTHER INFORMATION: n is t or c

<400> SEQUENCE: 11
acgttttgcc aaatttatgg tgcaaattn                                        29

<210> SEQ ID NO 12
<211> LENGTH: 32
<212> TYPE: DNA
<213> ORGANISM: Phaseolus vulgaris
<220> FEATURE:
<221> NAME/KEY: misc_feature
<222> LOCATION: (32)..(32)
<223> OTHER INFORMATION: n is t or g

<400> SEQUENCE: 12
catacaaata atataactttt taaggatcca an                                   32
```

```
<210> SEQ ID NO 13
<211> LENGTH: 25
<212> TYPE: DNA
<213> ORGANISM: Phaseolus vulgaris
<220> FEATURE:
<221> NAME/KEY: misc_feature
<222> LOCATION: (25)..(25)
<223> OTHER INFORMATION: n is c or a

<400> SEQUENCE: 13
ctggttaaat tctccttgtc ttagn                                            25

<210> SEQ ID NO 14
<211> LENGTH: 121
<212> TYPE: DNA
<213> ORGANISM: Phaseolus vulgaris
<220> FEATURE:
<221> NAME/KEY: misc_feature
<222> LOCATION: (61)..(61)
<223> OTHER INFORMATION: n is a or c

<400> SEQUENCE: 14
agtttggttc ctctgaattt atatttattt tattacatga gttttttttt tataataatt      60
natgcacatg aatcttaata ttcaaagtag aaactaatct tgataccaca tatttaaagt     120
g                                                                    121

<210> SEQ ID NO 15
<211> LENGTH: 121
<212> TYPE: DNA
<213> ORGANISM: Phaseolus vulgaris
<220> FEATURE:
```

-continued

<221> NAME/KEY: misc_feature
<222> LOCATION: (61)..(61)
<223> OTHER INFORMATION: n is t or c

<400> SEQUENCE: 15
caaaatttgc tgactgctta ggttttgcat ataattggtg aatacagatt accaatttta      60
ntgaataaat aaaacttatt tgaatatgat tacctgctga gaaacacgaa ctgcctctgt     120
c                                                                    121

<210> SEQ ID NO 16
<211> LENGTH: 121
<212> TYPE: DNA
<213> ORGANISM: Phaseolus vulgaris
<220> FEATURE:
<221> NAME/KEY: misc_feature
<222> LOCATION: (61)..(61)
<223> OTHER INFORMATION: n is a or g

<400> SEQUENCE: 16
gaagaactca atatttatgt caaaagaaaa cgatagtaag atgaccttct gaaggaactg      60
naaattgttg aataaaactt ttcaagtctg gaccactggt tttacctgca tagagattgt     120
a                                                                    121

<210> SEQ ID NO 17
<211> LENGTH: 121
<212> TYPE: DNA
<213> ORGANISM: Phaseolus vulgaris
<220> FEATURE:
<221> NAME/KEY: misc_feature
<222> LOCATION: (61)..(61)
<223> OTHER INFORMATION: n is a or g

<400> SEQUENCE: 17
tgtgtacaga atgcggggtg aaagaaaatg aagaatggtg gtggcagatt tattttggaa      60
naagaatcca cttatgctct gtaaatagtg tattctgaag gtatgggtga agagtgaaga     120
a                                                                    121

<210> SEQ ID NO 18
<211> LENGTH: 121
<212> TYPE: DNA
<213> ORGANISM: Phaseolus vulgaris
<220> FEATURE:
<221> NAME/KEY: misc_feature
<222> LOCATION: (61)..(61)
<223> OTHER INFORMATION: n is t or g

<400> SEQUENCE: 18
atttcatcaa cttcacatca ccgattctca aattctcttt attctcatgt gttgcaaaat      60
nacatagttg cttaacgatc tatgttcaga attctgattc gttgctaatt gttagtgatt     120
a                                                                    121

<210> SEQ ID NO 19
<211> LENGTH: 121
<212> TYPE: DNA
<213> ORGANISM: Phaseolus vulgaris
<220> FEATURE:
<221> NAME/KEY: misc_feature
<222> LOCATION: (61)..(61)
<223> OTHER INFORMATION: n is a or c

<400> SEQUENCE: 19
ttcttccttc tactttgtat cacaggcagt tccttctgac acattacaag attatatttt      60

```
ntgttgtcttt aaaaggaaat agataaagat caagaaaaat aggggaaggt aaaccatatg    120
a                                                                    121

<210> SEQ ID NO 20
<211> LENGTH: 121
<212> TYPE: DNA
<213> ORGANISM: Phaseolus vulgaris
<220> FEATURE:
<221> NAME/KEY: misc_feature
<222> LOCATION: (61)..(61)
<223> OTHER INFORMATION: n is t or g

<400> SEQUENCE: 20
tttattctag atttggctgc ttgaaattta taggttttga tgaaaatatg cttattgatg    60
ntcttgtgcc tagcagaggt tctctcatta gcacacaata caaacatgaa ctacgtattg    120
a                                                                    121

<210> SEQ ID NO 21
<211> LENGTH: 121
<212> TYPE: DNA
<213> ORGANISM: Phaseolus vulgaris
<220> FEATURE:
<221> NAME/KEY: misc_feature
<222> LOCATION: (61)..(61)
<223> OTHER INFORMATION: n is t or c

<400> SEQUENCE: 21
ggtcaaagaa gcaattaaag ataaaaaaaa tagacaaggg tgaaatctga atgtgatctg    60
ngctcaagaa taacatagtc ttagaaaaca tcttcatttt gaacaaaatc ttaaagggag    120
a                                                                    121

<210> SEQ ID NO 22
<211> LENGTH: 121
<212> TYPE: DNA
<213> ORGANISM: Phaseolus vulgaris
<220> FEATURE:
<221> NAME/KEY: misc_feature
<222> LOCATION: (61)..(61)
<223> OTHER INFORMATION: n is a or g

<400> SEQUENCE: 22
ttcatcattt cctccaacat aaaccatact tcttattact cactgctcac ttcagctact    60
ncttctgctt gattgcattt cgattaatcc gcttcttaat acttcacaaa tctcaatacc    120
c                                                                    121

<210> SEQ ID NO 23
<211> LENGTH: 121
<212> TYPE: DNA
<213> ORGANISM: Phaseolus vulgaris
<220> FEATURE:
<221> NAME/KEY: misc_feature
<222> LOCATION: (61)..(61)
<223> OTHER INFORMATION: n is g or a

<400> SEQUENCE: 23
ttgtcgatgt gagattttca atacatccgc ttacgttgag attctctaac tcgtgcgtac    60
nactatatat ttatgagtgg tccgataata aacccaacaa actctcatta tgatagattc    120
t                                                                    121

<210> SEQ ID NO 24
```

```
<211> LENGTH: 121
<212> TYPE: DNA
<213> ORGANISM: Phaseolus vulgaris
<220> FEATURE:
<221> NAME/KEY: misc_feature
<222> LOCATION: (61)..(61)
<223> OTHER INFORMATION: n is a or g

<400> SEQUENCE: 24
atttgtcaaa gagacaatag tgtaaagttc cggagtagga gagaaatttt ggaaaattag      60
naatttgcac cataaatttg gcaaaacgtg gattaaggtt tttgtgagaa acaaataatg     120
g                                                                    121

<210> SEQ ID NO 25
<211> LENGTH: 121
<212> TYPE: DNA
<213> ORGANISM: Phaseolus vulgaris
<220> FEATURE:
<221> NAME/KEY: misc_feature
<222> LOCATION: (61)..(61)
<223> OTHER INFORMATION: n is c or a

<400> SEQUENCE: 25
atatttcatg catctccatg ttttcaagtg gccacatata gaatatcatc tgcatctatt      60
nttggatcct taaaagttat attatttgta tgatttcata ttctccttac tatatcaatt     120
a                                                                    121

<210> SEQ ID NO 26
<211> LENGTH: 121
<212> TYPE: DNA
<213> ORGANISM: Phaseolus vulgaris
<220> FEATURE:
<221> NAME/KEY: misc_feature
<222> LOCATION: (61)..(61)
<223> OTHER INFORMATION: n is g or t

<400> SEQUENCE: 26
ttccaaattg tgcatctact aaccatattc cttcctgcag caacatggat agtaccccaa      60
nctaagacaa ggagaattta accagaccac aacacaatga gcataccaga ccctagagga     120
a                                                                    121

<210> SEQ ID NO 27
<211> LENGTH: 32
<212> TYPE: DNA
<213> ORGANISM: Artificial Sequence
<220> FEATURE:
<223> OTHER INFORMATION: SNP 1 Forward Primer 1

<400> SEQUENCE: 27
ttctactttg aatattaaga ttcatgtgca tt                                   32

<210> SEQ ID NO 28
<211> LENGTH: 30
<212> TYPE: DNA
<213> ORGANISM: Artificial Sequence
<220> FEATURE:
<223> OTHER INFORMATION: SNP 1 Forward Primer 2

<400> SEQUENCE: 28
ctactttgaa tattaagatt catgtgcatg                                      30

<210> SEQ ID NO 29
<211> LENGTH: 30
```

<210> SEQ ID NO 30
<211> LENGTH: 33
<212> TYPE: DNA
<213> ORGANISM: Artificial Sequence
<220> FEATURE:
<223> OTHER INFORMATION: SNP 1 Reverse Primer

<400> SEQUENCE: 29
agtttggttc ctctgaattt atatttattt　　　　　　　　　　　　　　　　　　　30

<210> SEQ ID NO 30
<211> LENGTH: 33
<212> TYPE: DNA
<213> ORGANISM: Artificial Sequence
<220> FEATURE:
<223> OTHER INFORMATION: SNP 2 Forward Primer 1

<400> SEQUENCE: 30
gtaatcatat tcaaataagt tttatttatt cag　　　　　　　　　　　　　　　　33

<210> SEQ ID NO 31
<211> LENGTH: 33
<212> TYPE: DNA
<213> ORGANISM: Artificial Sequence
<220> FEATURE:
<223> OTHER INFORMATION: SNP 2 Forward Primer 2

<400> SEQUENCE: 31
gtaatcatat tcaaataagt tttatttatt caa　　　　　　　　　　　　　　　　33

<210> SEQ ID NO 32
<211> LENGTH: 30
<212> TYPE: DNA
<213> ORGANISM: Artificial Sequence
<220> FEATURE:
<223> OTHER INFORMATION: SNP 2 Reverse Primer

<400> SEQUENCE: 32
ctgcttaggt tttgcatata attggtgaat　　　　　　　　　　　　　　　　　　30

<210> SEQ ID NO 33
<211> LENGTH: 26
<212> TYPE: DNA
<213> ORGANISM: Artificial Sequence
<220> FEATURE:
<223> OTHER INFORMATION: SNP 3 Forward Primer 1

<400> SEQUENCE: 33
gtaagatgac cttctgaagg aactga　　　　　　　　　　　　　　　　　　　　26

<210> SEQ ID NO 34
<211> LENGTH: 24
<212> TYPE: DNA
<213> ORGANISM: Artificial Sequence
<220> FEATURE:
<223> OTHER INFORMATION: SNP 3 Forward Primer 2

<400> SEQUENCE: 34
aagatgacct tctgaaggaa ctgg　　　　　　　　　　　　　　　　　　　　　24

<210> SEQ ID NO 35
<211> LENGTH: 29
<212> TYPE: DNA
<213> ORGANISM: Artificial Sequence
<220> FEATURE:
<223> OTHER INFORMATION: SNP 3 Reverse Primer

<400> SEQUENCE: 35
ccagtggtcc agacttgaaa agtttttatt                                      29

<210> SEQ ID NO 36
<211> LENGTH: 29
<212> TYPE: DNA
<213> ORGANISM: Artificial Sequence
<220> FEATURE:
<223> OTHER INFORMATION: SNP 4 Forward Primer 1

<400> SEQUENCE: 36
actatttaca gagcataagt ggattctttt                                      29

<210> SEQ ID NO 37
<211> LENGTH: 28
<212> TYPE: DNA
<213> ORGANISM: Artificial Sequence
<220> FEATURE:
<223> OTHER INFORMATION: SNP 4 Forward Primer 2

<400> SEQUENCE: 37
ctatttacag agcataagtg gattcttc                                        28

<210> SEQ ID NO 38
<211> LENGTH: 29
<212> TYPE: DNA
<213> ORGANISM: Artificial Sequence
<220> FEATURE:
<223> OTHER INFORMATION: SNP 4 Reverse Primer

<400> SEQUENCE: 38
agaatggtgg tggcagattt attttggaa                                       29

<210> SEQ ID NO 39
<211> LENGTH: 27
<212> TYPE: DNA
<213> ORGANISM: Artificial Sequence
<220> FEATURE:
<223> OTHER INFORMATION: SNP 5 Forward Primer 1

<400> SEQUENCE: 39
gaacatagat cgttaagcaa ctatgtc                                         27

<210> SEQ ID NO 40
<211> LENGTH: 29
<212> TYPE: DNA
<213> ORGANISM: Artificial Sequence
<220> FEATURE:
<223> OTHER INFORMATION: SNP 5 Forward Primer 2

<400> SEQUENCE: 40
ctgaacatag atcgttaagc aactatgta                                       29

<210> SEQ ID NO 41
<211> LENGTH: 29
<212> TYPE: DNA
<213> ORGANISM: Artificial Sequence
<220> FEATURE:
<223> OTHER INFORMATION: SNP 5 Reverse Primer

<400> SEQUENCE: 41
agaatggtgg tggcagattt attttggaa                                       29

<210> SEQ ID NO 42
<211> LENGTH: 32
<212> TYPE: DNA
<213> ORGANISM: Artificial Sequence

```
<220> FEATURE:
<223> OTHER INFORMATION: SNP 6 Forward Primer 1

<400> SEQUENCE: 42
tgatctttat ctatttcctt ttaagacaac at                                   32

<210> SEQ ID NO 43
<211> LENGTH: 31
<212> TYPE: DNA
<213> ORGANISM: Artificial Sequence
<220> FEATURE:
<223> OTHER INFORMATION: SNP 6 Forward Primer 2

<400> SEQUENCE: 43
gatctttatc tatttccttt taagacaaca g                                    31

<210> SEQ ID NO 44
<211> LENGTH: 29
<212> TYPE: DNA
<213> ORGANISM: Artificial Sequence
<220> FEATURE:
<223> OTHER INFORMATION: SNP 6 Reverse Primer

<400> SEQUENCE: 44
gcagttcctt ctgacacatt acaagatta                                       29

<210> SEQ ID NO 45
<211> LENGTH: 30
<212> TYPE: DNA
<213> ORGANISM: Artificial Sequence
<220> FEATURE:
<223> OTHER INFORMATION: SNP 7 Forward Primer 1

<400> SEQUENCE: 45
aggttttgat gaaaatatgc ttattgatgg                                      30

<210> SEQ ID NO 46
<211> LENGTH: 32
<212> TYPE: DNA
<213> ORGANISM: Artificial Sequence
<220> FEATURE:
<223> OTHER INFORMATION: SNP 7 Forward Primer 2

<400> SEQUENCE: 46
ataggttttg atgaaaatat gcttattgat gt                                   32

<210> SEQ ID NO 47
<211> LENGTH: 25
<212> TYPE: DNA
<213> ORGANISM: Artificial Sequence
<220> FEATURE:
<223> OTHER INFORMATION: SNP 7 Reverse Primer

<400> SEQUENCE: 47
atgagagaac ctctgctagg cacaa                                           25

<210> SEQ ID NO 48
<211> LENGTH: 29
<212> TYPE: DNA
<213> ORGANISM: Artificial Sequence
<220> FEATURE:
<223> OTHER INFORMATION: SNP 8 Forward Primer 1

<400> SEQUENCE: 48
gttttctaag actatgttat tcttgagcg                                       29
```

<210> SEQ ID NO 49
<211> LENGTH: 29
<212> TYPE: DNA
<213> ORGANISM: Artificial Sequence
<220> FEATURE:
<223> OTHER INFORMATION: SNP 8 Forward Primer 2

<400> SEQUENCE: 49
gttttctaag actatgttat tcttgagca                                    29

<210> SEQ ID NO 50
<211> LENGTH: 30
<212> TYPE: DNA
<213> ORGANISM: Artificial Sequence
<220> FEATURE:
<223> OTHER INFORMATION: SNP 8 Reverse Primer

<400> SEQUENCE: 50
aaatagacaa gggtgaaatc tgaatgtgat                                   30

<210> SEQ ID NO 51
<211> LENGTH: 24
<212> TYPE: DNA
<213> ORGANISM: Artificial Sequence
<220> FEATURE:
<223> OTHER INFORMATION: SNP 9 Forward Primer 1

<400> SEQUENCE: 51
actcactgct cacttcagct acta                                         24

<210> SEQ ID NO 52
<211> LENGTH: 23
<212> TYPE: DNA
<213> ORGANISM: Artificial Sequence
<220> FEATURE:
<223> OTHER INFORMATION: SNP 9 Forward Primer 2

<400> SEQUENCE: 52
ctcactgctc acttcagcta ctg                                          23

<210> SEQ ID NO 53
<211> LENGTH: 29
<212> TYPE: DNA
<213> ORGANISM: Artificial Sequence
<220> FEATURE:
<223> OTHER INFORMATION: SNP 9 Reverse Primer

<400> SEQUENCE: 53
cggattaatc gaaatgcaat caagcagaa                                    29

<210> SEQ ID NO 54
<211> LENGTH: 24
<212> TYPE: DNA
<213> ORGANISM: Artificial Sequence
<220> FEATURE:
<223> OTHER INFORMATION: SNP 10 Forward Primer 1

<400> SEQUENCE: 54
gagattctct aactcgtgcg taca                                         24

<210> SEQ ID NO 55
<211> LENGTH: 23
<212> TYPE: DNA
<213> ORGANISM: Artificial Sequence
<220> FEATURE:
<223> OTHER INFORMATION: SNP 10 Forward Primer 2

```
<400> SEQUENCE: 55
agattctcta actcgtgcgt acg                                              23

<210> SEQ ID NO 56
<211> LENGTH: 29
<212> TYPE: DNA
<213> ORGANISM: Artificial Sequence
<220> FEATURE:
<223> OTHER INFORMATION: SNP 10 Reverse Primer

<400> SEQUENCE: 56
gttgggttta ttatcggacc actcataaa                                        29

<210> SEQ ID NO 57
<211> LENGTH: 29
<212> TYPE: DNA
<213> ORGANISM: Artificial Sequence
<220> FEATURE:
<223> OTHER INFORMATION: SNP 11 Forward Primer 1

<400> SEQUENCE: 57
acgttttgcc aaatttatgg tgcaaattt                                        29

<210> SEQ ID NO 58
<211> LENGTH: 28
<212> TYPE: DNA
<213> ORGANISM: Artificial Sequence
<220> FEATURE:
<223> OTHER INFORMATION: SNP 11 Forward Primer 2

<400> SEQUENCE: 58
cgttttgcca aatttatggt gcaaattc                                         28

<210> SEQ ID NO 59
<211> LENGTH: 29
<212> TYPE: DNA
<213> ORGANISM: Artificial Sequence
<220> FEATURE:
<223> OTHER INFORMATION: SNP 11 Reverse Primer

<400> SEQUENCE: 59
ccggagtagg agagaaattt tggaaaatt                                        29

<210> SEQ ID NO 60
<211> LENGTH: 32
<212> TYPE: DNA
<213> ORGANISM: Artificial Sequence
<220> FEATURE:
<223> OTHER INFORMATION: SNP 12 Forward Primer 1

<400> SEQUENCE: 60
catacaaata atataacttt taaggatcca at                                    32

<210> SEQ ID NO 61
<211> LENGTH: 32
<212> TYPE: DNA
<213> ORGANISM: Artificial Sequence
<220> FEATURE:
<223> OTHER INFORMATION: SNP 12 Forward Primer 2

<400> SEQUENCE: 61
catacaaata atataacttt taaggatcca ag                                    32

<210> SEQ ID NO 62
```

```
<211> LENGTH: 29
<212> TYPE: DNA
<213> ORGANISM: Artificial Sequence
<220> FEATURE:
<223> OTHER INFORMATION: SNP 12 Reverse Primer

<400> SEQUENCE: 62
ggccacatat agaatatcat ctgcatcta                                    29

<210> SEQ ID NO 63
<211> LENGTH: 25
<212> TYPE: DNA
<213> ORGANISM: Artificial Sequence
<220> FEATURE:
<223> OTHER INFORMATION: SNP 13 Forward Primer 1

<400> SEQUENCE: 63
ctggttaaat tctccttgtc ttagc                                        25

<210> SEQ ID NO 64
<211> LENGTH: 27
<212> TYPE: DNA
<213> ORGANISM: Artificial Sequence
<220> FEATURE:
<223> OTHER INFORMATION: SNP 13 Forward Primer 2

<400> SEQUENCE: 64
gtctggttaa attctccttg tcttaga                                      27

<210> SEQ ID NO 65
<211> LENGTH: 25
<212> TYPE: DNA
<213> ORGANISM: Artificial Sequence
<220> FEATURE:
<223> OTHER INFORMATION: SNP 13 Reverse Primer

<400> SEQUENCE: 65
tgcagcaaca tggatagtac cccaa                                        25

<210> SEQ ID NO 66
<211> LENGTH: 32
<212> TYPE: DNA
<213> ORGANISM: Phaseolus vulgaris

<400> SEQUENCE: 66
ttctactttg aatattaaga ttcatgtgca tt                                32

<210> SEQ ID NO 67
<211> LENGTH: 29
<212> TYPE: DNA
<213> ORGANISM: Phaseolus vulgaris

<400> SEQUENCE: 67
ctactttgaa tattaagatt catgtgcat                                    29

<210> SEQ ID NO 68
<211> LENGTH: 32
<212> TYPE: DNA
<213> ORGANISM: Phaseolus vulgaris

<400> SEQUENCE: 68
gtaatcatat tcaaataagt tttatttatt ca                                32

<210> SEQ ID NO 69
<211> LENGTH: 33
```

```
<212> TYPE: DNA
<213> ORGANISM: Phaseolus vulgaris

<400> SEQUENCE: 69
gtaatcatat tcaaataagt tttatttatt caa                                   33

<210> SEQ ID NO 70
<211> LENGTH: 26
<212> TYPE: DNA
<213> ORGANISM: Phaseolus vulgaris

<400> SEQUENCE: 70
gtaagatgac cttctgaagg aactga                                          26

<210> SEQ ID NO 71
<211> LENGTH: 23
<212> TYPE: DNA
<213> ORGANISM: Phaseolus vulgaris

<400> SEQUENCE: 71
aagatgacct tctgaaggaa ctg                                             23

<210> SEQ ID NO 72
<211> LENGTH: 28
<212> TYPE: DNA
<213> ORGANISM: Phaseolus vulgaris

<400> SEQUENCE: 72
actatttaca gagcataagt ggattctt                                        28

<210> SEQ ID NO 73
<211> LENGTH: 28
<212> TYPE: DNA
<213> ORGANISM: Phaseolus vulgaris

<400> SEQUENCE: 73
ctatttacag agcataagtg gattcttc                                        28

<210> SEQ ID NO 74
<211> LENGTH: 27
<212> TYPE: DNA
<213> ORGANISM: Phaseolus vulgaris

<400> SEQUENCE: 74
gaacatagat cgttaagcaa ctatgtc                                         27

<210> SEQ ID NO 75
<211> LENGTH: 28
<212> TYPE: DNA
<213> ORGANISM: Phaseolus vulgaris

<400> SEQUENCE: 75
ctgaacatag atcgttaagc aactatgt                                        28

<210> SEQ ID NO 76
<211> LENGTH: 32
<212> TYPE: DNA
<213> ORGANISM: Phaseolus vulgaris

<400> SEQUENCE: 76
tgatctttat ctatttcctt ttaagacaac at                                   32

<210> SEQ ID NO 77
```

<210> SEQ ID NO 77
<211> LENGTH: 30
<212> TYPE: DNA
<213> ORGANISM: Phaseolus vulgaris

<400> SEQUENCE: 77
gatctttatc tatttccttt taagacaaca                                30

<210> SEQ ID NO 78
<211> LENGTH: 30
<212> TYPE: DNA
<213> ORGANISM: Phaseolus vulgaris

<400> SEQUENCE: 78
aggttttgat gaaaatatgc ttattgatgg                                30

<210> SEQ ID NO 79
<211> LENGTH: 31
<212> TYPE: DNA
<213> ORGANISM: Phaseolus vulgaris

<400> SEQUENCE: 79
ataggttttg atgaaaatat gcttattgat g                              31

<210> SEQ ID NO 80
<211> LENGTH: 28
<212> TYPE: DNA
<213> ORGANISM: Phaseolus vulgaris

<400> SEQUENCE: 80
gttttctaag actatgttat tcttgagc                                  28

<210> SEQ ID NO 81
<211> LENGTH: 29
<212> TYPE: DNA
<213> ORGANISM: Phaseolus vulgaris

<400> SEQUENCE: 81
gttttctaag actatgttat tcttgagca                                 29

<210> SEQ ID NO 82
<211> LENGTH: 24
<212> TYPE: DNA
<213> ORGANISM: Phaseolus vulgaris

<400> SEQUENCE: 82
actcactgct cacttcagct acta                                      24

<210> SEQ ID NO 83
<211> LENGTH: 22
<212> TYPE: DNA
<213> ORGANISM: Phaseolus vulgaris

<400> SEQUENCE: 83
ctcactgctc acttcagcta ct                                        22

<210> SEQ ID NO 84
<211> LENGTH: 23
<212> TYPE: DNA
<213> ORGANISM: Phaseolus vulgaris

<400> SEQUENCE: 84
gagattctct aactcgtgcg tac                                       23

-continued

```
<210> SEQ ID NO 85
<211> LENGTH: 23
<212> TYPE: DNA
<213> ORGANISM: Phaseolus vulgaris

<400> SEQUENCE: 85
agattctcta actcgtgcgt acg                                        23

<210> SEQ ID NO 86
<211> LENGTH: 29
<212> TYPE: DNA
<213> ORGANISM: Phaseolus vulgaris

<400> SEQUENCE: 86
acgttttgcc aaatttatgg tgcaaattt                                  29

<210> SEQ ID NO 87
<211> LENGTH: 27
<212> TYPE: DNA
<213> ORGANISM: Phaseolus vulgaris

<400> SEQUENCE: 87
cgttttgcca aatttatggt gcaaatt                                    27

<210> SEQ ID NO 88
<211> LENGTH: 31
<212> TYPE: DNA
<213> ORGANISM: Phaseolus vulgaris

<400> SEQUENCE: 88
catacaaata ataaactttt aaggatcca a                                31

<210> SEQ ID NO 89
<211> LENGTH: 32
<212> TYPE: DNA
<213> ORGANISM: Phaseolus vulgaris

<400> SEQUENCE: 89
catacaaata ataaactttt aaggatcca ag                               32

<210> SEQ ID NO 90
<211> LENGTH: 25
<212> TYPE: DNA
<213> ORGANISM: Phaseolus vulgaris

<400> SEQUENCE: 90
ctggttaaat tctccttgtc ttagc                                      25

<210> SEQ ID NO 91
<211> LENGTH: 26
<212> TYPE: DNA
<213> ORGANISM: Phaseolus vulgaris

<400> SEQUENCE: 91
gtctggttaa attctccttg tcttag                                     26
```

SINGLE NUCLEOTIDE POLYMORPHISM (SNP) MARKERS FOR *PHASEOLUS VULGARIS* L. AND METHODS OF USE THEREOF IN SELECTION EFFICIENCY WITH BREEDING STRATEGIES

CROSS REFERENCE TO RELATED APPLICATION

This application is a continuation of and claims the benefit of U.S. patent application Ser. No. 15/837,732, titled "Single Nucleotide Polymorphism (SNP) Markers for *Phaseolus Vulgaris* L. and Methods of Use Thereof in Selection Efficiency with Breeding Strategies," filed on Dec. 12, 2017, the entirety of which is incorporated herein by reference.

FIELD

The present invention relates generally to plant molecular biology in the field of breeding common beans (*Phaseolus vulgaris* L.). More specifically, the invention relates to single nucleotide polymorphism (SNP) markers and flanking sequences of certain SNPs located on chromosomes 1, 2, 3, 6, 7, 8, and 11 of the common bean genome (see, Phytozyme: *Phaseolus vulgaris, v*2.1), associated with the phenotypic expression of volatile (flavor) compounds, such as, 3-hexen-1-ol, 1-octen-3-ol, linalool, 1-penten-3-ol, 1-hexanol, and/or β-ionone, which are associated with the flavor and taste quality of the common bean, as well as methods of using one or more molecular markers (i.e., SNP, SNP flanking sequence, PCR primer for a SNP) to identify flavor and taste qualities associated with volatiles in the common bean for the purposes of efficiency with breeding strategies, and introgression of genes associated with the SNP markers.

Also, the present invention provides common bean seeds, plant parts, cells, and/or tissues comprising any one or more of the molecular markers, i.e., SNP 1 through SNP 13, in their genome, and comprising otherwise a genome of a cultivated common bean.

BACKGROUND

The common bean (*Phaseolus vulgaris* L.), also known as the string bean, field bean, flageolet bean, French bean, garden bean, green bean, haricot bean, pop bean, snap bean, or snap, is a herbaceous annual plant grown worldwide for its edible dry seed (known as just "beans") or unripe fruit ("green beans"). Its botanical classification, along with other *Phaseolus* species, is as a member of the legume family Fabaceae. Wild *P. vulgaris* is native to the Americas and was domesticated separately in Mesoamerica and in the southern Andes region. This provides the basis for the domesticated common bean having two gene pools.

The main categories of common beans, as characterized by their use, are dry beans, which are seeds harvested at complete maturity, snap beans, which are tender pods with reduced fiber harvested before the seed development phase, and shell beans, which are seeds harvested at physiological maturity.

The common bean is a highly variable species with a long history of cultivation. Over 130 varieties of common beans are known. All wild members of the species have a climbing habit. Most cultivars are classified as "pole beans" or "bush beans" depending on their growth habits. Pole beans have a climbing habit and produce a twisting vine, which must be supported by poles, trellises, or other means. Bush beans are short plants that grow to not more than 2 feet (61 cm) in height, often without needing support to grow. Bush beans generally reach maturity and produce all of their fruit in a relatively short period of time, then cease to produce.

There are many varieties specialized for use as green beans due to the succulence and flavor of their pods. These varieties are usually grown in home vegetable gardens. Pod color can be green, yellow, purple, red, or streaked. Shapes range from thin "fillet" types to wide "romano" types and more common types in between. Examples of bush (dwarf) types include, but are not limited to, 'Blue Lake 274', 'Bush Kentucky Wonder', 'Derby', 'Dwarf French Bean Seeds—Safari (Kenyan Bean)', and 'Purple Teepee'. Examples of pole type green beans include, but are not limited to, 'Algarve French Climbing Bean', 'Blue Lake FM-1 Pole Bean', 'Golden Gate Pole Bean', 'Kentucky Blue Pole Bean', and 'Kentucky Wonder'.

Volatile compounds provide the primary source of flavor in common beans. Common beans are known to produce at least a hundred volatile compounds in their pods (Barra et al., 2007). Flavor volatiles are derived primarily from three biosynthetic pathways in plants (Lewinsohn et al., 2001). The three pathways are those for fatty acids, carotenoids/terpenoids, and the phenylpropanoid/shikimic acid. The fatty acid pathway begins with acetyl CoA and proceeds through palmitic acid, stearic acid, and oleic acid. Oleic acid is converted in the plastids to linoleic acid and linolenic acid through the action of desaturases. Linoleic and linolenic acids are, in turn, converted to volatile compounds important to flavor through the action of a lipoxygenase followed by a hydroperoxide lyase (Noordermeer et al., 2001). This pathway leads to the majority of flavor volatiles in common beans, such as 1-octen-3-ol, 1-penten-3-one, 1-penten-3-ol, hexanal, 1-hexanol, 2-hexenal, and 3-hexen-1-ol (De Lumen et al., 1978). Alternatively, acetyl CoA can be used in either the melavolate or non-melavolate pathway for terpenoid synthesis (Dubey et al. 2003). The melavolate pathway and non-melavolate pathway result in isopentenyl diphosphate (IPP) and dimethylallyl diphosphate (DMAPP). IPP and DMAPP are believed to be interchangeable through an isomerase and are the substrates for geranyl diphosphate synthase to produce geranyl diphosphate (GPP). GPP can either be used to produce monoterpenes, such as linalool, or undergo additional enzymatic changes to produce sesquiterpenes, carotenoids, or polyterpenes. The breakdown of carotenoids by the carotenoid cleavage dioxygenase I (CCD1) enzyme results in β-ionone (Wei et al., 2011). Both linalool and β-ionone are known to be present in common bean pods. Finally, the shikimic pathway followed by the phenylpropanoid pathway generates numerous volatile compounds in addition to an array of other compounds, such as flavonoids, lignans, esters, coumarins, and stilbenes (Vogt, 2010).

Early research on the genetics of flavor in snap beans was focused on linalool and 1-octen-3-ol because these compounds were present in variable amounts depending on the bean cultivar, and because these compounds appeared to be important to the characteristic flavor of snap beans (Stevens et al., 1967a; Toya et al., 1976). The results of crosses of beans expressing linalool and 1-octen-3-ol suggested that the amount of these two compounds in a bean were controlled by a small number of loci. This early genetic research was particularly focused on several Blue Lake commercial lines, which share a common ancestry with significant inheritance from the Mesoamerican center of domestication.

There is little known about the inheritance of flavor traits in common beans other than two early studies by Stevens et al. (1967a) and Toya et al. (1976). These studies predate the advent of molecular markers in plant breeding and did not identify quantitative trait loci (QTL), SNPs, or even chromosomes related to the inheritance of flavor traits in common beans. Moreover, Stevens and Toyo disagreed on the number of loci present, but did show that linalool and 1-octen-3-ol levels are heritable traits.

The common bean is a diploid species with 22 chromosomes (Sarbhoy 1978; Maréchal et al. 1978). The chromosomes are small in size and similar in morphology. The genome size of *P. vulgaris* is about a 580 Mbp/haploid genome (Bennett and Leitch 2005). The genome relates to two distinct evolutionary lineages, i.e., Andean and Mesoamerican, that predate domestication (Debouck et al. 1993; Kami et al. 1995). The genome sequence of common bean (*P. vulgaris* L.) was published in 2014 by Schmutz et al. It is also published by Phytozyme, which is the Plant Comparative Genomics portal of the Department of Energy's Joint Genome Institute. The Phytozyme genome for the common bean is published as *Phaseolus vulgaris, v2.1* (Common bean), see, Phytozome.jgi.doe.gov/pz/portal.html#!info?alias=Org_Pvulgaris, and is incorporated herein by reference. This published genome includes about 27,433 total loci containing 36,995 protein-coding transcripts. See, Phytozyme: *Phaseolus vulgaris, v2.1*. In the common bean, the levels of duplication and the amount of highly repeated sequences are generally low. Early mapping experiments demonstrated that most loci are single copy (Vallejos et al. 1992; Freyre et al. 1998; McClean et al. 2002).

With the emergence of the genomic era in the field of common beans, it became possible to conduct genome wide association study (GWAS) mapping of this important crop. Due to the amount of recombination events over time in a natural population in comparison to the limited number of recombination events in a biparental cross, GWAS tends to give higher genomic resolution in comparison to linkage mapping studies. GWAS mapping is also faster because a study can be completed in a single season on an established population of beans, in comparison to the need to grow multiple generations to perform biparental linkage studies.

The flavor of green beans involves complicated interactions between different volatiles. This makes the task of breeding flavor qualities associated with volatiles into later generations challenging. In this regard, the goal of developing new common bean cultivars requires evaluation of parents and the progeny of crosses in the F1, F2, or later generations. To reach this goal, a breeder must carefully select and develop plants that have desired flavor traits in cultivars. The absence of predictable success of any given cross requires that a breeder make several crosses with different breeding objectives, all of which is time consuming, costly, and requires growth time and space, pedigree selection, and numerous crossing and backcrossing steps. To date, bean breeders have typically focused on traits with simpler genetics as compared to flavor traits, and a more immediate impact on the bottom line, such as high yield.

Thus, there is an ongoing need for the development of stable, high yield cultivars of common beans that express superior flavor quality traits, as well as the identification and development of molecular markers for genes relevant to flavor traits, and methods of using flavor-specific molecular markers for refining bean breeding schemes to develop superior cultivars having high quality taste. For example, it would be extremely helpful if bean breeders could use molecular markers to determine whether genes relating to specific flavor traits are present in any given common bean population, then use the presence or absence of certain genes in a common bean population to develop efficient breeding designs. Molecular markers for flavor volatiles would allow selection of superior lines in early generations, without wasting time or space on poor selections. It would provide an objective measure to identify the selections because the ability of a plant breeder to actually taste hundreds or thousands of potential selections in the field is highly limited and impractical. Indeed, molecular markers, e.g., a SNP, a SNP flanking sequence, a PCR primer(s) for a SNP, could be beneficial for use in marker assisted identification of candidate bean populations and marker assisted selection for efficient breeding. SNP markers are direct marker systems for tagging genes and could be used to rapidly identify genes in plants that express desired flavor traits.

DESCRIPTION OF THE FIGURES

The patent or application file contains at least one drawing executed in color. Copies of this patent or patent application publication with color drawing(s) will be provided by the Office upon request and payment of the necessary fee.

Additional aspects, features, and advantages of the invention, as to its operation, will be understood and will become more readily apparent when the invention is considered in light of the following description of illustrative embodiments made in conjunction with the accompanying drawings, wherein:

FIG. 6A shows a Manhattan plot and FIG. 6B shows a QQ plot for FarmCPU GWAS of 1-hexanol. 1PC was used, and data was not transformed. Chromosomes are shown on the x-axis of the Manhattan plot and negative log p-values on the y-axis. Bonferroni cutoffs for all markers and effective markers are shown as lines across the Manhattan plot. Shown on the x-axis of the QQ plot are expected negative log p-values and on the y-axis are observed negative log p-values.

FIG. 7A shows a Manhattan plot and FIG. 7B shows a QQ plot for the FarmCPU GWAS for 1-penten-3-ol. 1PC was used, and data was not transformed. Chromosomes are shown on the x-axis of the Manhattan plot and negative log p-values on the y-axis. Bonferroni cutoffs for all markers and effective markers are shown as lines across the Manhattan plot. Shown on the x-axis of the QQ plot are expected negative log p-values and on the y-axis are observed negative log p-values.

FIG. 8A shows a Manhattan plot and FIG. 8B shows a QQ plot for the FarmCPU GWAS of β-ionone. 1PC was used, and data was not transformed. Chromosomes are shown on the x-axis of the Manhattan plot and negative log p-values on the y-axis. Bonferroni cutoffs for all markers and effective marker β-ionone s are shown as lines across the Manhattan plot. Shown on the x-axis of the QQ plot are expected negative log p-values and on the y-axis are observed negative log p-values.

FIG. 9A shows a Manhattan plot and FIG. 9B shows a QQ plot for the FarmCPU GWAS of 3-hexen-1-ol. 1PC was used, and data was not transformed. Chromosomes are shown on the x-axis of the Manhattan plot and negative log p-values on the y-axis. Bonferroni cutoffs for all markers and effective markers are shown as lines across the Manhattan plot. Shown on the x-axis of the QQ plot are expected negative log p-values and on the y-axis are observed negative log p-values.

FIG. 10 illustrates a cluster (Cartesian) plot of fluorescent signals reporting each individual DNA sample obtained from a bean line (see, TABLE J) having SNP 1. The FAM fluorescence value associated with the FAM-labelled oligo sequence (FAM-labeled primer) is plotted on the X axis. The data points plotted close to the X axis represent high FAM signal and no HEX signal generated during the KASP reaction, and the related bean line samples (see, TABLE J), are homozygous for the allele reported by FAM, i.e., A. The HEX fluorescence value associated with the HEX-labelled oligo sequence (HEX-labeled primer) is plotted on the Y axis. The data points plotted close to the Y axis represent high HEX signal and no FAM signal generated during the KASP reaction, and the related bean line samples (see, TABLE J), are homozygous for the allele reported by HEX, i.e., C. A sample that is heterozygous contains both the allele reported by FAM and the allele reported by HEX and generated half as much FAM fluorescence and half as much HEX fluorescence in comparison to the samples that are homozygous for these alleles. This data point is plotted in the center of the plot, representing half FAM signal and half HEX signal. The KASP reaction without any template DNA, i.e., no template control (NTC), is included as a negative control to ensure reliability and did not generate any fluorescence, and the data point is plotted at the origin.

DESCRIPTION OF EMBODIMENTS OF THE INVENTION

Figure 1:
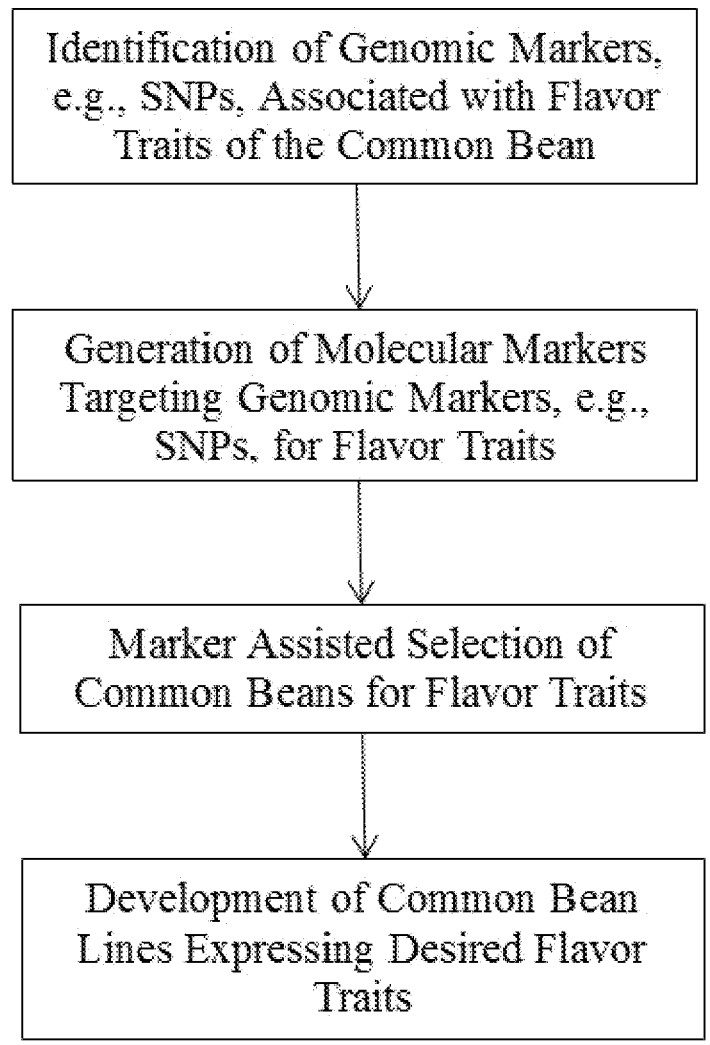
FIG. 1 is a flow chart illustrating general methods of the molecular marker selection of the present invention.

Illustrative and alternative embodiments and operational details of the single nucleotide polymorphism (SNP) markers for *Phaseolus vulgaris*, as well as methods of use thereof in selection efficiency with breeding common beans, are discussed in detail below with reference to the figures and the following definitions of terms.

Definitions

The capital letter "A" is used in reference to the nucleotide adenine.

The term "allele" is one or more alternative forms of a gene at a particular locus, all of which alleles relate to one trait or characteristic at a specific locus. In a diploid cell of an organism, alleles of a gene are located at a specific location, or locus on a chromosome. One allele is present on each chromosome of the pair of homologous chromosomes. A diploid plant species may comprise a large number of different alleles at a particular locus. These may be identical alleles of the gene (homozygous) or two different alleles (heterozygous).

The capital letter "C" is used in reference to the nucleotide cytosine.

The terms "common bean genome," "physical position on the common bean genome" and specific "chromosome" number are used in reference to the physical genome of cultivated common bean, see *Phaseolus vulgaris* v2.1 (Common bean) available at Phytozome.jgi.doe.gov/pz/portal.html#!info?alias=Org_Pvulgaris, the physical chromosomes, and the physical position on the chromosomes. So, for example SNP 1 is a T or G nucleotide positioned physically at base number 2939690 of chromosome 1.

The term "pure line" means the progeny of a single homozygous individual produced by repeated selfing.

The term "cultivar," also known as "cultivated variety" refers to a product of plant breeding that is released for access to producers that is uniform, distinct, stable, and new.

The term "cultivated common bean" or "domesticated common bean" refers to plants of *Phaseolus vulgaris*, i.e., common bean varietals, breeding lines or cultivars, cultivated by humans.

The term "Dickson Collection" refers to numerous common beans sourced from an uncatalogued set of accessions collected by Michael Dickson (Emeritus, Cornell Univ., Ithaca, N.Y.) in China in 1991.

The terms "F1", "F2", "F3", etc., (which "F" refers to filial generation) are used to refer to related generations following a cross between two parent plants or parent lines and later crosses between progeny of earlier crosses. Plants grown from the seeds produced by crossing two plants or lines are called the F1 generation. Crossing and/or selfing F1 plants results in the F2 generation, etc.

The capital letter "G" is used in reference to the nucleotide guanine.

The term "gene" is a genomic DNA sequence having a transcribed region, which is transcribed into a messenger RNA molecule (mRNA) in a cell, and an operably linked regulatory region, e.g. a promoter. Different alleles of a gene are different alternatives of the gene.

The term "heirloom" refers to a plant genotype that is maintained by gardeners or farmers in relative isolation, and through open pollination. Heirloom plants are typically not used in large-scale agriculture.

The term "Kompetitive Allele Specific PCR" or "KASP" is a homogenous, fluorescence-based genotyping variant of Polymerase Chain Reaction. KASP is based on allele-specific oligo extension and fluorescence resonance energy transfer for signal generation. KASP genotyping assays are based on competitive allele-specific PCR and enable bi-allelic scoring of single nucleotide polymorphisms (SNPs) and insertions and deletions at specific loci. The SNP-specific KASP Assay mix and the universal KASP Master mix are added to DNA samples. Reaction volumes can be either 5 µl or 10 µl. Half of the reaction volume must be KASP Master mix meaning that 2.5 µl of a 5 µl reaction or 5 µl of a 10 µl reaction must be KASP Master mix. The remaining volume in the reaction may be filled by water if necessary, but must contain 5 ng to 50 ng of genomic DNA and either 0.07 µl of KASP Assay mix for the 5 µl reaction or 0.14 µl of KASP Assay mix for the 10 µl reaction. A thermal cycling reaction is then performed wherein the thermal cycler conditions begin with 94° C. held for 15 minutes for "hot start activation", which is necessary to activate the Taq polymerase. After this phase, the temperature cycles ten times through the following: 94° C. for 20 seconds, and 61° C. to 55° C. for 60 seconds, dropping 0.6° C. per cycle from 61° C. down to 55° C. over 10 cycles. In the last phase, the temperature cycles 26 times from 94° C. for 20 seconds followed by 55° C. for 60 seconds. The end-point fluorescent reading is made with any FRET capable instrument that can excite fluorophores between 485 nm and 575 nm and read light emissions between 520 nm and 610 nm. Such instruments may include, but are not limited to, the following makes and models: Biotek Synergy 2, ABI 7500, ABI 7300, ABI 7900, ABI ViiA7, Roche LC480, Agilent Mx3000P/3005P, Illumina EcoRT, and BIO-RAD CFX. A passive reference dye, 5-carboxy-X-rhod-amine succinimidyl ester (ROX), is included in the master mix to allow for the normalization of the HEX and FAM signals due to slight variations in well volume. The KASP Assay mix contains three assay-specific non-labelled oligomers: two allele-specific forward primers and one common reverse primer. The allele-specific forward primers each have a unique tail sequence (on the 5' end) that corresponds with a universal FRET (fluorescence resonant energy transfer) cassette. One allele-specific forward primer is labelled with FAM™ dye, and the other allele-specific forward primer is labelled with HEX™ dye. The KASP Master mix contains the universal FRET cassettes, ROX™ passive reference dye, taq polymerase, free nucleotides, and $MgCl_2$ in an optimized buffer solution. During thermal cycling, the relevant allele-specific forward primer binds to the template and elongates, thus attaching the tail sequence to the newly synthesized strand. The complement of the allele-specific tail sequence is then generated during subsequent rounds of PCR, enabling the FRET cassette to bind to the DNA. The FRET cassette is no longer quenched and emits fluorescence. Bi-allelic discrimination is achieved through the competitive binding of two allele-specific forward primers, each with a unique tail sequence that corresponds with two universal FRET (fluorescence resonant energy transfer) cassettes with primers for a SNP; one labelled with FAM™ dye and the other with HEX™ dye. Upon completion of the KASP reactions, the resulting fluorescence is measured, the raw data is interpreted, and genotypes are assigned to the DNA samples by plotting fluorescence values for each sample on a cluster plot (Cartesian plot). The fluorescent signal from each individual DNA sample is represented as an independent data point on a cluster plot. One axis is used to plot the FAM fluorescence value (typically the X axis) and the second axis is used to plot the HEX fluorescence value (typically the Y axis) for each sample. A sample that is homozygous for an allele reported by FAM will only generate FAM fluorescence during the KASP reaction. This data point is plotted close to the X axis, representing high FAM signal and no HEX signal. A sample that is homozygous for the allele reported by HEX will only generate HEX fluorescence during the KASP reaction. This data point is plotted close to the Y axis, representing high HEX signal and no FAM signal. A sample that is heterozygous will contain both the allele reported by FAM and the allele reported by HEX. This sample will generate half as much FAM fluorescence and half as much HEX fluorescence as the samples that are homozygous for these alleles. This data point is plotted in the center of the plot, representing half FAM signal and half HEX signal. The KASP reaction without any template DNA is included as a negative control to ensure reliability. This is referred to as a no template control (NTC) and will not generate any fluorescence and the data point will therefore be plotted at the origin.

The term "landrace" refers to a population of plants, typically genetically heterogeneous, commonly developed in traditional agriculture from many years of farmer-directed selection, and which is specifically adapted to local conditions. Landraces tend to be relatively genetically uniform, but are more diverse than members of a standardized or formal breed.

The term "locus" (singular) or "loci" (plural) means a specific place or places, or a site on a chromosome where a gene or molecular marker, such as a SNP, is found.

The term "marker" is a nucleotide sequence or a fragment of such sequence, e.g., a single nucleotide polymorphism (SNP), used as a point of reference at an identifiable physical location on a chromosome (e.g. restriction enzyme cutting site, gene) whose inheritance can be tracked. Markers can be derived from genomic nucleotide sequences or from expressed nucleotide sequences (e.g., from a spliced RNA, cDNA, etc.). The term can also refer to nucleic acid sequences complementary to or flanking a marker. The term can also refer to nucleic acid sequences used as a molecular marker probe, primer, primer pair, or a molecule that can be used to identify the presence of a marker locus, e.g., a nucleic acid probe that is complementary to a marker locus sequence, and is capable of amplifying sequence fragments using PCR and modified PCR reaction methods. Examples of markers associated with flavor traits of common beans, i.e., volatile compounds, include SNP 1 through SNP 13 and/or flanking sequences of the *P. vulgaris* genome related to SNP 1 through SNP 13 (see, TABLE A, TABLE B, and TABLE C), as well as primers capable of identifying SNP 1 through SNP 13 (see, TABLE H), or a fragment of such sequences. Markers of the present invention can include sequences having 95% or better sequence identity to any of the sequences provided in SEQ ID NOS: 1-91, or any fragment thereof.

The term "marker assay" refers generally to a molecular marker assay, such as PCR, KASP, or SSR, for example, used to identify whether a certain DNA sequence or SNP, for example, is present in a sample of DNA. For example, a marker assay can include a molecular marker assay, e.g., KASP assay, which can be used to test whether a cultivated, landrace, heirloom, or pureline *P. vulgaris* plant has a SNP associated with an expression of a trait from DNA extracted from the *P. vulgaris* plant. Markers corresponding to genetic polymorphisms between members of a population can be detected by methods commonly used in the art including, PCR-based sequence specific amplification methods, detection of restriction fragment length polymorphisms (RFLPs), detection of amplified variable sequences of the plant genome, detection of simple sequence repeats (SSRs), detection of single nucleotide polymorphisms (SNPs), or detection of amplified fragment length polymorphisms (AFLPs). Well established methods are also known for the detection of expressed sequence tags (ESTs) and SSR markers derived from EST sequences and randomly amplified polymorphic DNA (RAPD).

The term "marker assisted selection" or "MAS" is a process of identifying and using the presence (or absence) of one or more molecular markers, e.g., a SNP, associated with a particular locus or to a particular chromosome region, to select plants for the presence of the specific locus. For example, the presence of a SNP known to be associated with a volatile compound can be used to detect and/or select common bean plants expressing the volatile compound of interest. MAS can be used to quickly introgress simply inherited traits, test early generations, break up linkage drag, pyramid genes, and/or authenticate the identity of a cultivar.

The term "parent line" refers to a genotype that has been selected for crossing in the initial stages of plant breeding. Such plants are typically genetically uniform and stable.

The term "plant" includes the whole plant, or any part or derivative thereof, such as, for example, leaves, stems, roots, root stock, root tips, flowers, pods, seeds, plant cells, plant cell or tissue cultures from which whole plants can be regenerated. Any reference to "seeds of a plant" can include either seeds from which the plant can be grown, or seeds produced on the plant, after self-fertilization or cross-fertilization.

The term "breeding line" is used in reference to genotypes resulting from breeding programs that may have a combination of traits that are of special interest to plant breeders.

The term "plant varietal" or "plant variety" is a group of plants in the same botanical taxonomy that express phenotypic characteristics resulting from a certain genotype or a combination of genotypes (i.e., F1 hybrids), that are distinguishable from any other phenotypic characteristics resulting from a different genotype within that species, and can be propagated without any change in the phenotypic expression.

The term "PVP" is an acronym for Plant Variety Protection and is used in reference to PVP certificates that protect certain intellectual property rights of breeders in new varieties of seeds and tubers and are issued by the Plant Variety Protection Office of the U.S. Department of Agriculture.

A "single-nucleotide polymorphism" or "SNP" is a variation in a single nucleotide that occurs at a specific position in a DNA sequence of a genome, where each variation is present to some appreciable degree within members of the same species or a paired chromosome (e.g., >1%). A SNP serves as a molecular marker used to assist in locating genes associated with certain traits expressed by genes related to the SNP. For example, at a specific base position in a genome, the base C may appear in a majority of the members of the same species, but in a minority of members of that same species, the position is occupied by the base A. The SNP at this specific base position, and the two possible nucleotide variations—C or A—are alleles for this base position. A SNP may fall within coding sequences of a gene, a non-coding region of a gene, or in intergenic regions. Reference to a SNP genotype at a specific position on a (+) strand or (−) strand of DNA, e.g., at locus 2939690 of chromosome 1 is T or G at position 32 of SEQ ID NO: 1, or of a sequence comprising at least 95% or more sequence identity to the SEQ ID NO: 1, means that the SNP genotype is present in a variant sequence at a nucleotide corresponding to the same nucleotide.

The terms "SSR" or "simple sequence repeat" refers to a polymorphic locus present in DNA consists of repeating units of 1-6 base pairs in length. Different alleles can have different numbers of the repeating SSR, resulting in different lengths of the alleles, as detectable, for example, by gel electrophoresis after amplification of the allele. These variations allow tracking of genotypic variation in breeding programs.

The capital letter "T" is used in reference to the nucleotide thymine.

The term "traditional breeding techniques" encompasses conventional approaches to breeding including, but not limited to, pedigree breeding, ideotype breeding, population breeding, hybrid breeding, plant domestication, pure line, and mass selection, any of which can be used in crossing, backcrossing, selfing, selection, double haploid production, mutation breeding, etc., as known to a common bean breeder, but exclude genetic modification, transformation, and transgenic methods, but by which an introgression fragment of a chromosome can be obtained, identified, and/or transferred to the next generation.

The term "wild common bean" or "primitive common bean" plants are common bean plants that possess the phenotype of a naturally occurring form.

The volatile compound β-ionone, also referred to as (E)-4-(2,6,6-trimethylcyclohexen-1-yl)but-3-en-2-one), is a ketone having organoleptic qualities described as sweet, fruity, woody, and berry-like with floral odor, and woody, floral, berry, and fruity with powdery nuanced taste (Mosciano, 1991b).

The volatile compound linalool, also referred to as 3,7-dimethylocta-1,6-dien-3-ol (IUPAC), is a naturally-occurring terpene alcohol having organoleptic qualities described as a soft, sweet, and floral odor, and a citrus, orange, lemon, floral, waxy, aldehydic and woody taste (Mosciano, 2007).

The volatile compound 1-hexanol, also referred to as hexan-1-ol (IUPAC), is an organic alcohol having organoleptic qualities described as fusel, oily, fruity, alcoholic, sweet, green, and fruit-like odor, and a green, fruity, apple-skin, and oily taste (Mosciano, 1997; Mosciano, 1993a).

The volatile compound 1-octen-3-ol, also referred to as, oct-1-en-3-ol (IUPAC), is a secondary alcohol and is formed during oxidative breakdown of linoleic acid. 1-octen-3-ol has organoleptic qualities described as mushroom, green, oily, and earth odor, and mushroom, earthy, fungal, green, oily, and vegetative taste (Mosciano, 1993a). 1-octen-3-ol has two isomers with slightly different odors, although taste sensation of either one, especially if unmixed with other compounds, is generally of mushrooms and fungi. In green beans, this organoleptic quality is different when mixed with other compounds. 1-octen-3-ol is considered to be a key volatile constituting "Blue Lake" bean flavor, but it only imparts this characteristic flavor when mixed in about a 1:4 ratio with 3-hexen-1-ol (Stevens et al. 1967b). In the relatively low concentrations found in green beans, 1-octen-3-ol mixes with 3-hexen-1-ol to form an earthy-green aroma. This compound is difficult to detect due to its low concentrations expressing an earthy green odor that blends into the overall aroma (Stevens et al., 1967b).

The volatile compound 1-penten-3-ol, also referred to as, pent-1-en-3-ol (IUPAC), is an organic alcohol having organoleptic qualities described as a horseradish-like and tropical fruity nuanced odor, and a green vegetable, fruity taste (Mosciano, 1991a).

The volatile compound 3-hexen-1-ol, also referred to as hex-3-en-1 (IUPAC), is an alcohol having organoleptic qualities described as a fresh, grassy, green, and oily odor, and a fresh, green, raw, fruity, and pungent taste (Stevens et al., 1967b).

Common Bean Plants SNP Expression

The present invention relates generally to common bean varietals, and more particularly to SNP markers, i.e., SNPs identified in SEQ ID NOs: 1-12 and SEQ ID NOs: 14-26, for common bean varietals phenotypically expressing one or more of 3-hexen-1-ol, 1-octen-3-ol, linalool, 1-penten-3-ol, 1-hexanol, or β-ionone.

TABLE A provides that the invention includes common bean plants with the presence of at least one of the single nucleotide polymorphisms (SNPs), i.e., SNP 1 through SNP 13, that are present at certain loci of certain chromosomes of the common bean genome (Phytozyme: *Phaseolus vulgaris*, v2.1). In the first round of the KASP assay reaction, the prevailing KASP forward primer hybridizes with its reverse complement on either the (+) strand or (−) strand of the denatured sample DNA. For example, the prevailing KASP forward primer for SNP 1 (allele X) matches the sequence of the (−) strand of the common bean genome (Phytozome, *P. vulgaris* v2.1) on Chromosome 1 from base pairs 2939721 to 2939690, and the prevailing KASP forward primer will hybridize with the reverse complementary sequence on the (+) strand of the DNA.

TABLE A

SNP #, SNP Locus, and Diagnostic KASP Primer BLAST ® Match (Phytozome *P. vulgaris* v2.1)

| SNP # | SNP, Locus | KASP Primer BLAST ® Match (allele) |
|---|---|---|
| SNP 1 | T or G at 2939690 | (5'→3') TTCTACTTTGAATATTAAGATTCATGTGCATT (SEQ ID NO: 1) Chr. 1: 2939721 . . . 2939690 (−) strand class = match length = 32 bp (X) |
| SNP 2 | G or A at 53768383 | (5'→3') GTAATCATATTCAAATAAGTTTTATTTATTCAA (SEQ ID NO: 2) Chr. 8: 53768415 . . . 53768383 (−) strand class = match_part length = 33 bp (Y) |
| SNP 3 | A or G at 14800672 | (5'→3') GTAAGATGACCTTCTGAAGGAACTGA (SEQ ID NO: 3) Chr. 6: 14800647 . . . 14800672 (+) strand class = match length = 26 bp (X) |
| SNP 4 | T or C at 47396341 | (5'→3') CTATTTACAGAGCATAAGTGGATTCTTC (SEQ ID NO: 4) Chr. 2: 47396314 . . . 47396341 (+) strand class = match length = 28 bp (Y) |
| SNP 5 | C or A at 19725396 | (5'→3') GAACATAGATCGTTAAGCAACTATGTC (SEQ ID NO: 5) Chr. 2: 19725422 . . . 19725396 (−) strand class = match length = 27 bp (X) |
| SNP 6 | T or G at 39538212 | (5'→3') TGATCTTTATCTATTTCCTTTTAAGACAACAT (SEQ ID NO: 6) Chr. 7: 39538243 . . . 39538212 (−) strand class = match length = 32 bp (X) |
| SNP 7 | G or T at 32623478 | (5'→3') AGGTTTTGATGAAAATATGCTTATTGATGG (SEQ ID NO: 7) Chr 7: 32623507 . . . 32623478 (−) strand class = match length = 30 bp (X) |
| SNP 8 | G or A at 44170119 | (5'→3') GTTTTCTAAGACTATGTTATTCTTGAGCA (SEQ ID NO: 8) Chr. 3: 44170091 . . . 44170119 (+) strand class = match length = 29 bp (Y) |
| SNP 9 | A or G at 32906019 | (5'→3') ACTCACTGCTCACTTCAGCTACTA (SEQ ID NO: 9) Chr. 3: 32906042 . . . 32906019 (−) strand class = match length = 24 bp (X) |
| SNP 10 | A or G at 54970429 | (5'→3') AGATTCTCTAACTCGTGCGTACG (SEQ ID NO: 10) Chr. 8: 54970451 . . . 54970429 (−) strand class = match_part length = 23 bp (Y) |
| SNP 11 | T or C at 51964707 | (5'→3') ACGTTTTGCCAAATTTATGGTGCAAATTT (SEQ ID NO: 11) Chr. 11: 51964679 . . . 51964707 (+) strand class = match length = 29 bp (X) |
| SNP 12 | T or G at 729615 | (5'→3') CATACAAATAATATAACTTTTAAGGATCCAAG (SEQ ID NO: 12) Chr. 2: 729646 . . . 729615 (−) strand class = match_part length = 32 bp (Y) |
| SNP 13 | C or A at 18092182 | (5'→3') CTGGTTAAATTCTCCTTGTCTTAGC (SEQ ID NO: 13) Chr. 7: 18092158 . . . 18092182 (+) strand class = match length = 25 bp (X) |

TABLE B summarizes the association of SNP 1 through SNP 13 with certain volatile compounds that provide certain flavor traits of the common bean.

TABLE B

Location of SNP on Chromosome and Relatedness of SNP to Volatile Compound Expression in Common Beans (Phytozyme: Phaseolus vulgaris v2.1).

| SNP Ref. # | SNP ID | Chromosome | Volatile Compound | IUPAC Nomenclature |
|---|---|---|---|---|
| SNP 1 | ss715645089 | 1 | 3-hexen-1-ol | hex-3-en-1-ol |
| SNP 2 | ss715645122 | 8 | 3-hexen-1-ol | hex-3-en-1-ol |
| SNP 3 | ss715645954 | 6 | 3-hexen-1-ol | hex-3-en-1-ol |
| SNP 4 | ss715646922 | 2 | 1-octen-3-ol | Oct-1-en-3-ol |
| SNP 5 | ss715649798 | 2 | 1-octen-3-ol | Oct-1-en-3-ol |
| SNP 6 | ss715645225 | 7 | 1-octen-3-ol | Oct-1-en-3-ol |
| SNP 7 | ss715648287 | 7 | linalool | 3,7-dimethylocta-1,6-dien-3-ol |
| SNP 8 | ss715639252 | 3 | 1-penten-3-ol | pent-1-en-3-ol |
| SNP 9 | ss715648169 | 3 | 1-penten-3-ol | pent-1-en-3-ol |
| SNP 10 | ss715639302 | 8 | 1-hexanol | Hexan-1-ol |
| SNP 11 | ss715640836 | 11 | 1-hexanol | Hexan-1-ol |
| SNP 12 | ss715639371 | 2 | β-ionone | (E)-4-(2,6,6-trimethylcyclohexen-1-yl)but-3-en-2-one |
| SNP 13 | ss715642582 | 7 | β-ionone | (E)-4-(2,6,6-trimethylcyclohexen-1-yl)but-3-en-2-one |

TABLE C identifies the flanking sequence (120 bp) at each SNP locus of common bean genome (Phytozyme: *Phaseolus vulgaris* v2.1). In certain instances, the SNP identified in the flanking sequence identified in Table C is the reverse complement of the SNP identified in Table A.

TABLE C

Flanking Sequence (120 bp) at SNP Locus of common bean genome (Phytozyme: *Phaseolus vulgaris*, v2.1).

| SNP # | Flanking Sequence at [SNP] (BLAST ® Result with Phytozome, *P. vulgaris*, v2.1) |
|---|---|
| SNP 1 | (5'→3') AGTTTGGTTCCTCTGAATTTATATTTATTTTATTACATGAGTTTTTT TTTTATAATAATT[AorC]ATGCACATGAATCTTAATATTCAAAGTAGAAAC TAATCTTGATACCACATATTTAAAGTG (SEQ ID NO: 14) (Chr. 1: 2939630 . . . 2939750 (+strand)) |
| SNP 2 | (5'→3') CAAAATTTGCTGACTGCTTAGGTTTTGCATATAATTGGTGAATACA GATTACCAATTTTA[TorC]TGAATAAATAAAACTTATTTGAATATGATTAC CTGCTGAGAAACACGAACTGCCTCTGTC (SEQ ID NO: 15) (Chr. 8: 53768323 . . . 53768443 (+strand)) |
| SNP 3 | (5'→3') GAAGAACTCAATATTTATGTCAAAAGAAAACGATAGTAAGATGA CCTTCTGAAGGAACTG[AorG]AAATTGTTGAATAAAACTTTTCAAGTCTGG ACCACTGGTTTTACCTGCATAGAGATTGTA (SEQ ID NO: 16) (Chr. 6: 14800612 . . . 14800732 (+strand)) |
| SNP 4 | (5'→3') TGTGTACAGAATGCGGGGTGAAAGAAAATGAAGAATGGTGGTGG CAGATTTATTTTGGAA[AorG]AAGAATCCACTTATGCTCTGTAAATAGTGT ATTCTGAAGGTATGGGTGAAGAGTGAAGAA (SEQ ID NO: 17) (Chr. 2: 47396281 . . . 47396401 (-strand)) |
| SNP 5 | (5'→3') ATTTCATCAACTTCACATCACCGATTCTCAAATTCTCTTTATTCTCA TGTGTTGCAAAAT[TorG]ACATAGTTGCTTAACGATCTATGTTCAGAATTC TGATTCGTTGCTAATTGTTAGTGATTA (SEQ ID NO: 18) (Chr. 2: 19725336 . . . 19725456 (+strand)) |
| SNP 6 | (5'→3') TTCTTCCTTCTACTTTGTATCACAGGCAGTTCCTTCTGACACATTAC AAGATTATATTTT[AorC]TGTTGTCTTAAAAGGAAATAGATAAAGATCAAG AAAAATAGGGgAAGGTAAACCATATGA (SEQ ID NO: 19) (Chr. 7: 39538152 . . . 39538272 (+strand)) |
| SNP 7 | (5'→3') TTTATTCTAGATTTGGCTGCTTGAAATTTATAGGTTTTGATGAAAA TATGCTTATTGATG[TorG]TCTTGTGCCTAGCAGAGGTTCTCTCATTAGCAC ACAATACAAACATGAACTACGTATTGA (SEQ ID NO: 20) (Chr. 7: 32623418 . . . 32623538 (-strand)) |

TABLE C-continued

Flanking Sequence (120 bp) at SNP Locus of common bean genome
(Phytozyme: *Phaseolus vulgaris*, v2.1).

| SNP # | Flanking Sequence at [SNP] (BLAST ® Result with Phytozome, *P. vulgaris*, v2.1) |
|---|---|
| SNP 8 | (5'→3')GGTCAAAGAAGCAATTAAAGATAAAAAAAaTAGACAAGGGTGAA ATCTGAATGTGATCTG[TorC]GCTCAAGAATAACATAGTCTTAGAAAACAT CTTCATTTTGAACAAAATCTTAAAGGGAGA (SEQ ID NO: 21) (Chr. 3: 44170059 . . . 44170179 (-strand)) |
| SNP 9 | (5'→3')TTCATCATTTCCTCCAACATAAACCATACTTCTTATTACTCACTGC TCACTTCAGCTACT[AorG]CTTCTGCTTGATTGCATTTCGATTAATCCGCTT CTTAATACTTCACAAATCTCAATACCC (SEQ ID NO: 22) (Chr. 3: 32905959 . . . 32906079 (-strand)) |
| SNP 10 | (5'→3')TTGTCGATGTGAGATTTTCAATACATCCGCTTACGTTGAGATTCTC TAACTCGTGCGTAC[GorA]ACTATATATTTATGAGTGGTCCGATAATAAAC CCAACAAACTCTCATTATGATAGATTCT (SEQ ID NO: 23) (Chr. 8: 54970369 . . . 54970489 (-strand)) |
| SNP 11 | (5'→3')ATTTGTCAAAGAGACAATAGTGTAAAGTTCCGGAGTAGGAGAGA AATTTTGGAAAATTAG[AorG]AATTTGCACCATAAATTTGGCAAAACGTG GATTAAGGTTTTTGTGAGAAACAAATAATGG (SEQ ID NO: 24) (Chr. 11: 51964647 . . . 51964767 (-strand)) |
| SNP 12 | (5'→3')ATATTTCATGCATCTCCATGTTTTCAAGTGGCCACATATAGAATAT CATCTGCATCTATT[CorA]TTGGATCCTTAAAAGTTATATTATTTGTATGAT TTCATATTCTCCTTACTATATCAATTA (SEQ ID NO: 25) (Chr. 2: 729555 . . . 729675 (+strand)) |
| SNP13 | (5'→3')TTCCAAATTGTGCATCTACTAACCATATTCCTTCCTGCAGCAACAT GGATAGTACCCCAA[GorT]CTAAGACAAGGAGAATTTAACCAGACCACAA CACAATGAGCATACCAGACCCTAGAGGAA (SEQ ID NO: 26) (Chr. 7: 18092122 . . . 18092242 (-strand)) |

Methods for identifying, selecting, introgressing, and breeding common bean varieties expressing one or more of the following volatile compounds: 3-hexen-1-ol, 1-octen-3-ol, linalool, 1-penten-3-ol, 1-hexanol, or β-ionone, are also described in further detail below.

Plant Material for *P. vulgaris*

The common bean genotypes were sourced from the Common Bean Coordinated Agricultural Project (Bean-CAP), which was a USDA-NIFA funded CAP to genotype and phenotype dry and snap bean diversity panels, including dry bean Mesoamerican and Andean diversity panels. Additionally, numerous common bean genotypes were sourced from an uncatalogued set of accessions collected by Michael Dickson (Emeritus, Cornell Univ., Ithaca, N.Y.) in China in 1991. A small number of genotypes were also sourced from seed catalogues specializing in heirloom types, and five came from a Spanish gene bank repository. In total, 50 common bean genotypes were utilized (see, TABLE D, TABLE E, and TABLE F).

TABLE D

Bush-type common bean lines of the Andean center of domestication

| Line | Accession # | Source of Material | PVP Cert. # | Type | Additional Geographic Parameters |
|---|---|---|---|---|---|
| Acclaim | PI 550420 | Seminis | 8900151 | commercial pureline | North America (Asgrow Seed) |
| B-1 | n/a | SerinXOregon5630 cross, F6 gen. | n/a | commercial pureline | North America |
| B-15 | n/a | SerinXOregon5630 cross, F6 gen. | n/a | commercial pureline | North America |
| B-28 | n/a | SerinXOregon5630 cross, F6 gen. | n/a | commercial pureline | North America |
| B-36 | n/a | SerinXOregon5630 cross, F6 gen. | n/a | commercial pureline | North America |
| B-37 | n/a | SerinXOregon5630 cross, F6 gen. | n/a | commercial pureline | North America |
| B-38 | n/a | SerinXOregon5630 cross, F6 gen. | n/a | commercial pureline | North America |
| B-41 | n/a | SerinXOregon5630 cross, F6 gen. | n/a | commercial pureline | North America |
| B-42 | n/a | SerinXOregon5630 cross, F6 gen. | n/a | commercial pureline | North America |
| BBL274 | n/a | Seminis | n/a | commercial pureline | North America |

TABLE D-continued

Bush-type common bean lines of the Andean center of domestication

| Line | Accession # | Source of Material | PVP Cert. # | Type | Additional Geographic Parameters |
|---|---|---|---|---|---|
| Benchmark | n/a | Syngenta | 9700096 | commercial pureline | North America (Novartis Seeds) |
| Booster | n/a | Syngenta | n/a | commercial pureline | likely North America |
| Calgreen | PI 538772 | Syngenta | 9000106 | commercial pureline | North America (Rogers Brothers Seed) |
| Castano | PI 612143 | Syngenta | 200000048 | commercial pureline | North America (Syngenta) |
| Coloma | PI 549954 | Syngenta | n/a | commercial pureline | North America (Rogers Brothers Seed |
| Cyclone | PI 599321 | Seminis | 9700327 | commercial pureline | North America (Seminis Vegetable Seeds) |
| Flavor Sweet | n/a | Harris Moran | n/a | commercial pureline | North America |
| Mercury | PI 661921 | Syngenta | 200000049 | commercial pureline | North America (Syngenta) |

TABLE E

Pole-type common bean lines of the Mesoamerican center of domestication

| Bean Line | Accession # | Source of material | PVP Cert. # | Type | Additional Geographic Parameters |
|---|---|---|---|---|---|
| 91-1009 | n/a | Dickson Collection | n/a | landrace | China |
| 91-1028 | n/a | Dickson Collection | n/a | landrace | China |
| 91-1145 | n/a | Dickson Collection | n/a | landrace | China |
| 91-1542 | n/a | Dickson Collection | n/a | landrace | China |
| 91-1643 | n/a | Dickson Collection | n/a | landrace | China |
| 91-1672 | n/a | Dickson Collection | n/a | landrace | China |
| 91-1728 | n/a | Dickson Collection | n/a | landrace | China |
| 91-1748 | n/a | Dickson Collection | n/a | landrace | China |
| 91-1750 | n/a | Dickson Collection | n/a | landrace | China |
| 91-1755 | n/a | Dickson Collection | n/a | landrace | China |
| 91-1759 | n/a | Dickson Collection | n/a | landrace | China |
| 91-1768 | n/a | Dickson Collection | n/a | landrace | China |
| 91-1976 | n/a | Dickson Collection | n/a | landrace | China |
| 91-2100 | n/a | Dickson Collection | n/a | landrace | China |
| 91-3346 | n/a | Dickson Collection | n/a | landrace | China |
| 91-3915 | n/a | Dickson Collection | n/a | landrace | China |
| 91-3918 | n/a | Dickson Collection | n/a | landrace | China |
| 91-3921 | n/a | Dickson Collection | n/a | landrace | China |

TABLE E-continued

Pole-type common bean lines of the Mesoamerican center of domestication

| Bean Line | Accession # | Source of material | PVP Cert. # | Type | Additional Geographic Parameters |
|---|---|---|---|---|---|
| 91-1033B | n/a | Dickson Collection | n/a | landrace | China |
| Cosse Violette Pole Bean | n/a | Amishland Heirloom Seeds, Reamstown, Pa. | n/a | heirloom | France |
| Blue Lake Stringless FM 1 | PI 549573 | USDA collection: Ferry-Morse Seed Company, Inc. | n/a | commercial pureline | North America |
| Fortex | n/a | Oregon State University | n/a | commercial pureline | France |
| Kentucky Wonder | PI 549742 | Syngenta | n/a | heirloom | North America (Kentucky) |
| New Mexico Cave Snap Pole | NA | Peace Seedlings, Corvallis, OR | n/a | heirloom | North America (New Mexico) |
| PHA-0315 | PHA-0315 | Misiòn Biològica de Galicia-CSIC. Pontevedra, Espàna | n/a | landrace | Spain |

TABLE F

Pole-type common bean lines of the Andean center of domestication

| Bean Line | Accession # | Material Source | PVP Cert.# | Type | Geographic Parameters |
|---|---|---|---|---|---|
| Aunt Ada's Italian | n/a | Turtle Tree Seed Copake, NY | n/a | heirloom | Italy (Turtle Tree Seed catalog: "came to Colorado from Italy with the Botanelli family circa 1900.") |
| Hidatsa Shield Figure Bean | n/a | Seed Savers Exchange, Decorah IA | n/a | landrace | North America (Hidatsa Native Americans, North Dakota) |
| PHA-0008 | PHA-0008 | Misiòn Biològica de Galicia-CSIC. Pontevedra, Espàna | n/a | landrace | Spain |
| PHA-0112 | PHA-0112 | Misiòn Biològica de Galicia-CSIC. Pontevedra, Espàna | n/a | landrace | Spain |
| PHA-0192 | PHA-0192 | Misiòn Biològica de Galicia-CSIC. Pontevedra, Espàna | n/a | landrace | Spain |
| PHA-0315 | PHA-0315 | Misiòn Biològica de Galicia-CSIC. Pontevedra, Espàna | n/a | landrace | Spain |
| Swiss Landfrauen Pole Bean | n/a | Amishland Heirloom Seeds, Reamstown, Pa. | n/a | heirloom | Switzerland |

The common bean plants for the 50 genotypes were grown in unreplicated plots (Oregon State University, Vegetable Research Farm, Corvallis, Oreg.). The plots have Chehalis silty clay loam soil and are located approximately 77 meters above sea level. Overhead irrigation provided one to two inches of water weekly, as needed. Pelleted fertilizer was banded beneath the row just prior to planting at the rate of 50 lbs of nitrogen per acre. After planting, seeds were treated with Captan fungicide and planted to a depth of approximately two inches in ten foot plots at a rate of 60 seeds per plot. Rows were 30 inches apart for bush types and 60 inches apart for pole types. Pole types were trellised on a metal wire approximately 6 feet above the ground, and bush types were unsupported. The picking time was varied to match the differing maturity dates of plots. Several representative pods from across the plot were picked and transported in a cooler to a freezer where they were frozen at −20° C.

GC-MS Analysis of Volatile Compounds Associated with Bean Flavor Traits

Gas chromatography and mass spectroscopy (GC-MS) was used to analyze the expression of volatile compounds associated with taste in the common bean. The results of the GC-MS analysis permitted the selection of volatile compounds based on (1) their importance to past flavor research in beans, (2) their presence in the biochemical pathway in common beans proposed by de Lumen et al. (1978), or (3) their novel organoleptic quality. Linalool, 1-octen-3-ol, 1-hexanol, 3-hexen-1-ol, 1-penten-3-ol, and β-ionone were selected as relevant volatile compounds to associate with candidate SNPs for marker assisted identification and selection.

GC-MS was conducted on a Shimadzu GC-2010 Plus and GCMS-QP2010 Ultra instruments with an attached Shimadzu AOC-5000 Plus auto sampler and chiller (Kyoto, Japan). The carrier gas was helium. The column was a 30 meter Stabilwax column with a 0.25 mm internal diameter from Restek (Bellefonte, Pa., USA). The solid-phase microextraction (SPME) fiber was a 50/30 μm Divinylbenzene/Carboxen/Polydimethylsiloxane with a 24 gauge needle size (Supelco/Sigma-Aldrich, Bellefonte, Pa., USA). Vials for the autosampler consisted of Restek 20 ml amber SPME vials with an 18 mm orifice and magnetic screw-thread caps (Bellefonte, Pa., USA) The GC parameters included a column oven temperature of 35° C., an injection temperature of 250° C., a pressure of 40 kpa, a total flow of 1.9 mL/min, a column flow of 0.45 ml/min, a linear velocity of 121 cm/sec, and a purge flow of 1.0 mL/min. The injection mode was split with a ratio of 1 and the flow control mode was pressure. The column oven temperature was set to 35° C. with a hold time of 10 minutes followed by a 4° C./min increase to a final temperature of 200° C. with a hold time of 2 minutes, then an additional ramp of 10° C./min to a final temperature of 250° C. for 5 minutes. The MS parameters were set to an ion surface temperature of 200° C., an interface temperature of 250° C., an absolute detector voltage of 1 k V, a solvent cut time of 3 minutes, a microscan width of 0, a microscan threshold of 200 u, and a GC program time of 61.25 minutes. The scan mode parameters were set to a start time of 3 minutes, and an end time of 60 minutes with an event time of 0.22, a scan speed of 1,428, and a starting and ending m/z of 33 to 330. The Combi Pal method consisted of pre-incubation for 10 minutes at 35° C. with agitation, vial penetration to 51 mm, extraction for 40 minutes at 35° C. with no agitation, injection penetration to 54 mm with desorption for 10 minutes. The Combi Pal agitation was on for 5 seconds and off for 2 seconds. There was a post-fiber-condition time of 10 minutes.

The green bean samples were thawed in groups of 30 to fill the chilled autosampler. One gram of material was weighed into a SPME vial and 1 μg of deuterated linalool was added, then the vial was capped and placed in the auto sampler. Samples were run continuously in a dedicated fashion with no major changes.

GC-MS data was analyzed using Shimadzu GCMS Postrun Analysis software and OpenChrom software. A NIST11 mass spectral library was integrated into the Shimadzu software, which allowed for the identification of mass spectrometry fragment patterns. All compounds mapped had been positively identified in green beans in previous published research and peak identification with the NIST11 library was in most cases at least a 95% or higher match (Stevens et al., 1967b; Toya et al., 1976; De Lumen et al., 1978; De Quirós et al., 2000; Barra et al., 2007).

Peak area for phenotyping bean cultivars was determined using the OpenChrom community edition software version 1.1.0.201607311225. Peaks were detected using the first derivative peak detector, and peak area was determined using the trapezoid peak integrator.

GWAS Analysis and Identification of SNPs Associated with Volatile Compounds

A genome-wide association study (GWAS), also known as whole genome association study (WGAS), was used to study the genome-wide set of genetic variants in the common bean genome (Phytozyme, *Phaseolus vulgaris* v2.1) to determine which genetic variants were associated with expression of specific volatile compounds associated with flavor, namely, 3-hexen-1-ol, 1-octen-3-ol, linalool, 1-penten-3-ol, 1-hexanol, or β-ionone. Genetic diversity of the GWAS population was determined using the HET and MTK functions of the GeneticSubsetter R package (Graebner et al, 2016). The bean lines were placed into either the Mesoamerican or Andean domestication pools using a discriminate principal component analysis in the adegenet R package (Jombart, 2008). Mean values were calculated for these pools for each volatile compound and the data was visualized with histograms. Homogeneity of variances (Fligner-Killeen test) and normality (Shapiro-Wilk test) were tested in addition to the histograms to determine the need for transforming the data, or for non-parametric tests. In some cases, the data met all assumptions of a t-test, and a 2-tailed t-test was performed comparing the mean values of Mesoamerican versus Andean lines. In certain cases, data was log transformed and if necessary, a non-parametric Mann-Whitney test was conducted. All visualizations, transformations, and analysis were performed using base R functions.

Figure 3:
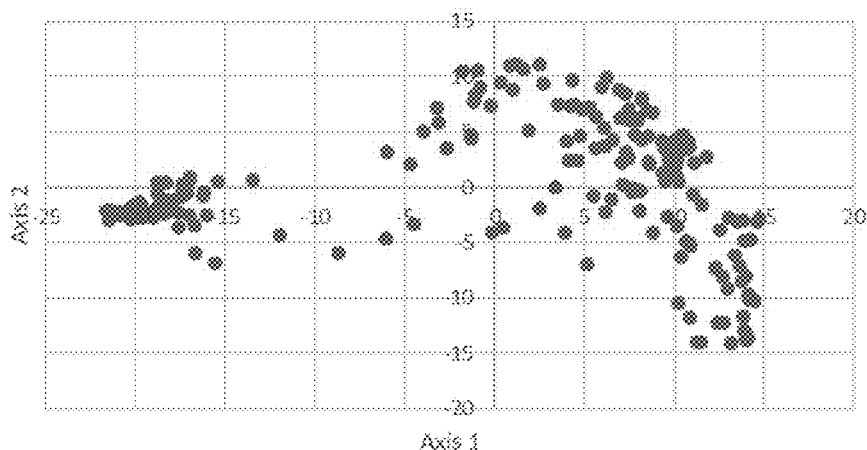
FIG. 3 is a biplot of the first and second axes of a principle components analysis (PCA) of the Bean CAP Snap Bean Diversity Panel (n=145) with an additional 56 snap bean lines of Chinese origin, genotyped using the Illumina Infinium Genechip BARCBEAN6K_3 platform Beadchip. The first and second axes account for 35.7% and 7.7% of the SNP variation, respectively. The first axis separates genotypes based on the Andean and Mesoamerican centers of domestication. The second axis separates European extra fine snap beans from others within the Mesoamerican center, and splits C phaseolin types (represented by Romanos and some snap beans) from T phaseolin snap beans within the Andean center.

To adjust for population structure, principal component analysis (PCA) was performed on the unfiltered SNP data using the adegenet R package (Jombart, 2008). The first axis accounted for 35.7% of the variation and the first three axes together accounted for nearly half the variation (see, FIG. 3). Four models were tested, namely, no principal component (PC), 1 PC, 2 PC, and 3 PC. GWAS was performed in both Tassel 5.2.24 (Bradbury et al., 2007) using a Mixed Linear Model (MLM) and in FarmCPU using the iterative fixed and random model (Liu et al., 2016). In both Tassel and FarmCPU, 1 PC usually resulted in the best QQ plot. A 1 PC model closely corresponded to the split between the centers of domestication. In no case did a 2 PC or 3 PC produce a tighter fit on the QQ plots. Due, in part, to the superior QQ plots and the biological basis of two centers of domestication, 1 PC was used as the method of population structure adjustment.

Association tests assume some degree of normality and transforming data to improve normality is one option (Goh and Yap, 2010). Histogram visualizations of the data and Shapiro-Wilke normality tests were conducted. Log transformation improved normality for 1-octen-3-ol and 3-hexen-1-ol as measured by a Shapiro-Wilke normality test, and improved normality for 1-penten-3-one and linalool. For these volatiles, GWAS was performed on both untransformed and transformed data sets. All log transformations, visualizations, and tests were performed using base R functions.

Manhattan plot cutoffs were generated using both α=0.05 Bonferroni cutoff and α=0.05 Bonferroni cutoff based on effective marker numbers. To correct for these inherent correlations between tests, effective marker numbers were calculated. The SimpleM method was used to calculate effective marker numbers. This changed the marker number from 5,317 total markers to 1,363 effective markers. Two lines were generated for all Manhattan plots showing these two cutoffs.

FarmCPU was used for GWAS with an added covariate of 1 PC. Analysis was performed in R using the FarmCPU source code provided by Liu et al. (2016). A minor allele frequency (MAF) of 0.05 was used, which reduced the SNP number to 4,540. An additional line of code was used to generate a complete list of SNPs in the results document: threshold.output=1. A Bonferroni cutoff at α=0.05 using all markers and a Bonferroni cutoff at α=0.05 using the effective marker number were generated using the following code: cutoff=c(0.05, 0.05*4,540/1,363). The negative log value of the p-value, which was used to construct Manhattan plots, were 4.958 and 4.435 respectively (see, TABLE G). Some models were also tested using a MLM in Tassel, version 5.2.24. These Tassel analyses used one or more PC and included a centered Identity By State (IBS) kinship generated by Tassel and 0.05 MAF filtering.

The proximity of local genes was determined using the BLAST® and Genome Browser tools of Phytozome (*Phaseolus vulgaris*, v2.1). A 50 Kbp flanking sequence was examined on either side of each significantly associated SNP (i.e. a 100 Kbp window). Structural genes relating to the fatty acid pathway and isoprenoid pathway (i.e. terpenoid/carotenoid pathway) were identified using a keyword search and their proximity to significantly associated SNPs were gauged. A keyword search in Phytozome for "lipoxygenase", "hydroperoxide lyase", and "alcohol dehydrogenase" resulted in 65 matches across the genome for "lipoxygenase" and "alcohol dehydrogenase", although there was only a single match on chromosome 5 for "hydroperoxide lyase". A similar search for "carotenoid cleavage dioxygenase", "linalool synthase", "geranylgeranyl diphosphate synthase", and "geranylgeranyl pyrophosphate synthase" in the isoprenoid pathway resulted in 15 matches across the genome but only 2 matches on chromosomes 2 and 6, respectively, for "linalool synthase".

Using a discriminate principal component analysis with two clusters in the adegenet R package (Jombart, 2008), the genotypes were divided into Mesoamerican genotypes for pole (see, TABLE E) and Andean genotypes for pole and bush (see, TABLE F and TABLE D, respectively). Tests of homogeneity of variances and normality were performed to determine which test to perform and whether or not to transform the data.

The results were highly significant for most volatiles. The Mesoamerican pool has statistically significant higher mean values for 1-octen-3-ol, 1-hexanol, 1-penten-3-ol, and 1-penten-3-one, but a statistically significant lower mean values for 3-hexen-1-ol, and β-ionone. The mean value for linalool was not significantly different between Mesoamerican and Andean centers of domestication.

Figure 4A:
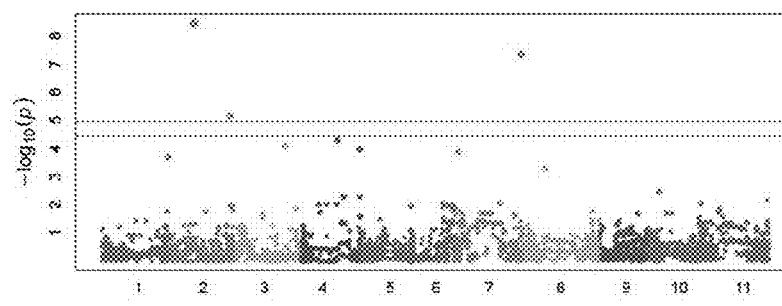
FIG. 4A shows a Manhattan plot and FIG. 4B shows a QQ plot for FarmCPU GWAS of 1-octen-3-ol peak area data. 1PC was used, and data was not transformed. Chromosomes are shown on the x-axis of the Manhattan plot and negative log p-values on the y-axis. Bonferroni cutoffs for all markers and effective markers are shown as lines across the Manhattan plot. Shown on the x-axis of the QQ plot are expected negative log p-values and on the y-axis are observed negative log p-values.
Figure 4B:
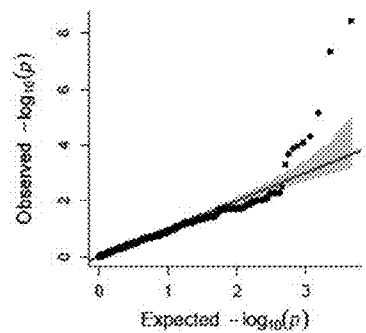
Figure 5A:
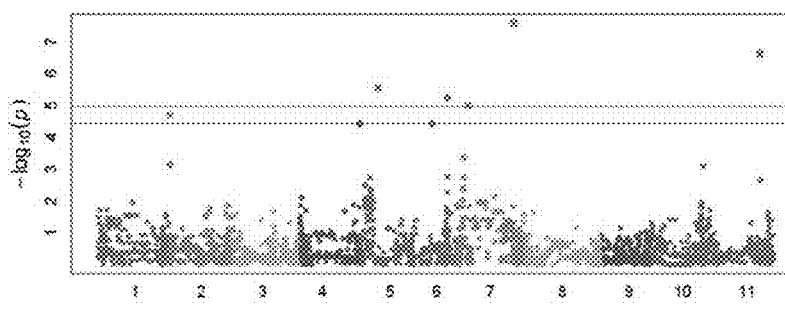
FIG. 5A shows a Manhattan plot and FIG. 5B shows a QQ plot for FarmCPU GWAS of linalool. 1PC was used, and data was not transformed. Chromosomes are shown on the x-axis of the Manhattan plot and negative log p-values on the y-axis. Bonferroni cutoffs for all markers and effective markers are shown as lines across the Manhattan plot. Shown on the x-axis of the QQ plot are expected negative log p-values and on the y-axis are observed negative log p-values.
Figure 5B:
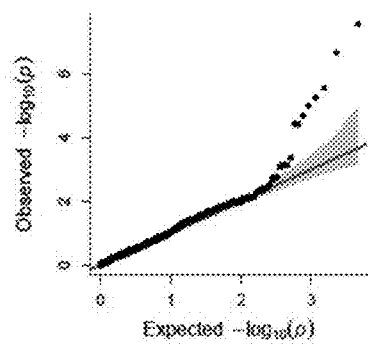

GWAS analysis using FarmCPU generated significant associations between SNP candidates and genes related to volatile compounds on 7 chromosomes of the common bean genome (Phytozyme: *Phaseolus vulgaris*, v2.1), namely, chromosomes 1, 2, 3, 6, 7, 8, and 11, related to expression of linalool, 1-octen-3-ol, 1-hexanol, 1-penten-3-ol, 1-penten-3-ol, and β-ionone (see, TABLE B). Manhattan plots and Quantile-Quantile (QQ) plots for 1-octen-3-ol are shown in FIGS. 4A and 4B, for linalool are shown in FIGS. 5A and 5B, for 1-hexanol are shown in FIGS. 6A and 6B, for 1-penten-3-ol are shown in FIGS. 7A and 7B, for β-ionone are shown in FIGS. 8A and 8B, and for 3-hexen-1-ol are shown in FIGS. 9A and 9B.

GWAS was also performed on log transformed data, if appropriate. Histograms were generated for all data sets and tests of normality were performed to determine if transformation might be beneficial.

TABLE G

GWAS and FarmCPU Selection Analysis

| SNP # | p-value | Neg. log p-value (used for GWAS Manhattan plot) | Minor allele frequency (MAF) |
|---|---|---|---|
| SNP 1 | 2.52E−06 | 5.60 | 0.23 |
| SNP 2 | 5.20E−09 | 8.28 | 0.40 |
| SNP 3 | 3.12E−06 | 5.51 | 0.37 |
| SNP 4 | 7.37E−06 | 5.13 | 0.09 |
| SNP 5 | 3.54E−09 | 8.45 | 0.16 |
| SNP 6 | 4.53E−08 | 7.34 | 0.24 |
| SNP 7 | 2.72E−08 | 7.57 | 0.16 |
| SNP 8 | 7.82E−06 | 5.11 | 0.33 |
| SNP 9 | 1.37E−05 | 4.86 | 0.23 |
| SNP 10 | 3.65E−07 | 6.44 | 0.47 |
| SNP 11 | 2.46E−07 | 6.61 | 0.11 |
| SNP 12 | 2.97E−05 | 4.53 | 0.20 |
| SNP 13 | 4.14E−06 | 5.38 | 0.21 |

The locations of structural genes were compared with the locations of candidate SNPs associated with expression of volatile compounds.

SNP 1 for 3-hexen-1-ol is at base pair location 2939690 on chromosome 1 (corresponding with position number 32 of SEQ ID NO. 1), which is 10,750 base pairs away from the transcription factor RAX-2 (panther), located from 2926823 bp to 2928940 bp (reverse) on chromosome 1 of the common bean genome (Phytozyme, *Phaseolus vulgaris*, v2.1).

SNP 2 for 3-hexen-1-ol is at base pair location 53768383 on chromosome 8 (corresponding with position number 33 of SEQ ID NO. 2), which is 121,050 base pairs away from the alpha/beta-hydrolysis superfamily, located from 53644804 bp to 53647333 bp (reverse) on chromosome 8 of the common bean genome (Phytozyme, *Phaseolus vulgaris*, v2.1).

SNP 3 for 3-hexen-1-ol is at base pair location 14800672 on chromosome 6 (corresponding with position number 26 of SEQ ID NO. 3), which is 30,190 base pairs away from the ring finger containing protein, located from 14830862 bp to 14837547 bp (reverse) on chromosome 6 of the common bean genome (Phytozyme, *Phaseolus vulgaris*, v2.1).

SNP 4 for 1-octen-3-ol is at base pair location 47396341 on chromosome 2 (corresponding with position number 28 of SEQ ID NO. 4), which is 0 base pairs away from the CCCH-type Zinc-finger protein, located from 47395507 bp to 47397585 bp (reverse) on chromosome 2 of the common bean genome (Phytozyme, *Phaseolus vulgaris*, v2.1).

SNP 5 for 1-octen-3-ol is at base pair location 19725396 on chromosome 2 (corresponding with position number 27 of SEQ ID NO. 5), which is 5,241 base pairs away from the lecithin-cholesterol gene, located from 19714226 bp to 19720155 bp (reverse) on chromosome 2 of the common bean genome (Phytozyme, *Phaseolus vulgaris*, v2.1).

SNP 6 for 1-octen-3-ol is at base pair location 39538212 on chromosome 7 (corresponding with position number 32 of SEQ ID NO. 6), which is 49,749 base pairs away from the aryl-alcohol dehydrogenase gene, located from 39483405 bp to 39488463 bp (reverse) on chromosome 7 of the common bean genome (Phytozyme, *Phaseolus vulgaris*, v2.1).

SNP 7 for linalool is at base pair location 32623478 on chromosome 7 (corresponding with position number 30 of SEQ ID NO. 7), which is 102,303 base pairs away from the transcription factor BHLH149 gene, located from 32520217 bp to 32521175 bp (forward) on chromosome 7 of the common bean genome (Phytozyme, *Phaseolus vulgaris*, v2.1).

SNP 8 for 1-penten-3-ol is at base pair location 44170119 on chromosome 3 (corresponding with position number 29 of SEQ ID NO. 8), which is 23,934 base pairs away from the alpha/beta-hydrolysis gene, located from 44140694 bp to 44146185 bp (forward) on chromosome 3 of the common bean genome (Phytozyme, *Phaseolus vulgaris*, v2.1).

SNP 9 for 1-penten-3-ol is at base pair location 32906019 on chromosome 3 (corresponding with position number 24 of SEQ ID NO. 9), which is 1,490 base pairs away from the protein ELF4-Like 2-Related gene, located from 32902817 bp to 32904529 bp (forward) on chromosome 3 of the common bean genome (Phytozyme, *Phaseolus vulgaris*, v2.1).

SNP 10 for 1-hexanol is at base pair location 54970429 on chromosome 8 (corresponding with position number 23 of SEQ ID NO. 10), which is 60,154 base pairs away from the F-box domain (F-box) gene, located from 54906455 bp to 54910275 bp (forward) on chromosome 8 of the common bean genome (Phytozyme, *Phaseolus vulgaris*, v2.1).

SNP 11 for 1-hexanol is at base pair location 51964707 on chromosome 11 (corresponding with position number 29 of SEQ ID NO. 11), which is 28,824 base pairs away from the VQ motif (VQ) gene, located from 51935530 bp to 51935883 bp (reverse) on chromosome 11 of the common bean genome (Phytozyme, *Phaseolus vulgaris*, v2.1).

SNP 12 for beta-ionone is at base pair location 729615 on chromosome 2 (corresponding with position number 32 of SEQ ID NO. 12), which is 35,848 base pairs away from the $C_2H_2$-type Zinc finger (zf-$C_2H_2$_6) gene, located from 765463 bp to 766998 bp (forward) on chromosome 2 of the common bean genome (Phytozyme, *Phaseolus vulgaris*, v2.1).

SNP 13 for beta-ionone is at base pair location 18092182 on chromosome 7 (corresponding with position number 25 of SEQ ID NO. 13), which is 4,418 base pairs away from the RNA recognition motif (a/k/a, RRM, RBD, or RNP domain) gene, located from 18085133 bp to 18087764 bp (forward) on chromosome 7 of the common bean genome (Phytozyme, *Phaseolus vulgaris*, v2.1).

Validation of KASP Primers with SNPs Identified in GWAS

KASP markers were developed for each of SNP 1 through SNP 13 (see, TABLE H). Each SNP-specific KASP marker comprises (1) competing allele-specific, forward primer sets having nucleotide sequences individually designed to match the target SNP marker and unique tail sequences labeled with either a fluorescent marker FAM or HEX that is associated with reporting the presence of a homozygous or heterozygous SNP, and (2) a reverse primer comprising a nucleotide sequence designed to amplify the target region.

Each of the 13 SNP-specific KASP markers was used to verify that the SNP markers identified and selected in the GWAS study, i.e., SNP 1 through SNP 13, amplified DNA extracted from 50 genotypes of common bean. The SNP primers were designed using the common bean genome (Phytozyme, *Phaseolus vulgaris*, v2.1) and were synthesized by LGC Limited (Herts, UK).

The frozen bean pods were ground into a fine powder with liquid nitrogen inside a specially modified steel Waring blender. The top of the blender had a long metal tube welded to the top to allow gases from the liquid nitrogen to vent while maintaining most of the liquid inside the blender. The slurry was allowed to boil off most of the liquid nitrogen within a plastic bag and then it was poured or tapped into a 40 ml amber vial with a PTFE liner (Supelco/Sigma-Aldrich, Bellefonte, Pa., USA).

'Acclaim', BBL274, 'Benchmark', 'Booster', 'Calgreen', 'Castano', 'Coloma', 'Cyclone', 'Flavor Sweet', 'Fortex', 'Kentucky Wonder', and 'Mercury', as well as the Dickson Collection genotypes were extracted using a modified CTAB method. Approximately 0.5 g of material from young trifoliate leaves taken early in the season were ground in 500 µl of CTAB buffer and then incubated for 1 hour at 65° C. This was extracted with 500 µl of chloroform. The supernatant was precipitated with 400 µl of 76% ethanol and 10% ammonium acetate. The pellets were dried and resuspended in 200 µl of TE buffer. The DNA was then treated with 8 µg of RNase A for 1 to 2 hours at 37° C. This was extracted with 300 µl of chloroform. The supernatant was precipitated with 15 µl of 3M sodium acetate (pH 5.2) and 300 µl of 95% ethanol. The resulting pellet was washed with 400 µl of 70% ethanol. The pellet was air dried and resuspended in 50 µl of TE buffer. The quality of the DNA was checked by running 1 µg of each sample on an agarose gel. Concentrations were determined by nanodrop (ND-1000 UV-Vis Spectrophotometer). All other BeanCAP genomic DNA samples were previously extracted and genotyped using the same method.

Extracted and concentrated DNA was used for the KASP assay using the SNP-specific KASP primers. The KASP assay was performed by mixing each of the DNA samples extracted from the 50 common beans with the SNP-specific KASP primers (i.e., competing allele-specific forward primers labeled with either FAM dye or HEX dye), the reverse primer, the KASP master mix containing FRET cassette plus taq polymerase in an optimized buffer solution. After a 94° C. 15 minute hot start to activate the Taq polymerase, the first cycle of PCR consists of 94° C. for 20 seconds, and 61° C. for 60 seconds. During this first round of PCR, the DNA sample was denatured to promote annealing whereby one of the competing forward primers matched the target SNP and the reverse primer amplified the target region. The second cycle of PCR consists of 94° C. for 20 seconds, and 60.4° C. for 60 seconds. During this second round of PCR, the complement of the allele-specific tail sequence of the forward primer was generated where the reverse primer binds, elongates and makes a complimentary copy of the allele specific tail. The third cycle of PCR consists of 94° C. for 20 seconds, and 59.8° C. for 60 seconds. During this third round of PCR, the cassette of FAM- or HEX-labeled primer hybridized to an oligo with covalently attached quencher binds to the complementary tail sequence, thereby releasing the fluorescence, i.e., FAM or HEX, from the quencher to generate a fluorescent signal that is read and plotted. In further rounds, the allele-specific tail increases.

TABLE H

KASP Primers for SNP 1 through SNP 13 Related to *P. vulgaris* Volatile Compounds

| SNP # | KASP Primers (target) | Nucleotide Sequence (5' to 3') |
|---|---|---|
| SNP 1 | Forward Primer 1 (allele X) | TTCTACTTTGAATATTAAGATTCATGTGCATT (SEQ ID NO: 27) |
| | Forward Primer 2 (allele Y) | CTACTTTGAATATTAAGATTCATGTGCATG (SEQ ID NO: 28) |
| | Reverse Primer | AGTTTGGTTCCTCTGAATTTATATTTATTT (SEQ ID NO: 29) |
| SNP 2 | Forward Primer 1 (allele X) | GTAATCATATTCAAATAAGTTTTATTTATTCAG (SEQ ID NO: 30) |
| | Forward Primer 2 (allele Y) | GTAATCATATTCAAATAAGTTTTATTTATTCAA (SEQ ID NO: 31) |
| | Reverse Primer | CTGCTTAGGTTTTGCATATAATTGGTGAAT (SEQ ID NO: 32) |
| SNP 3 | Forward Primer 1 (allele X) | GTAAGATGACCTTCTGAAGGAACTGA (SEQ ID NO: 33) |
| | Forward Primer 2 (allele Y) | AAGATGACCTTCTGAAGGAACTGG (SEQ ID NO: 34) |
| | Reverse Primer | CCAGTGGTCCAGACTTGAAAAGTTTTATT (SEQ ID NO: 35) |
| SNP 4 | Forward Primer 1 (allele X) | ACTATTTACAGAGCATAAGTGGATTCTTT (SEQ ID NO: 36) |
| | Forward Primer 2 (allele Y) | CTATTTACAGAGCATAAGTGGATTCTTC (SEQ ID NO: 37) |
| | Reverse Primer | AGAATGGTGGTGGCAGATTTATTTTGGAA (SEQ ID NO: 38) |
| SNP 5 | Forward Primer 1 (allele X) | GAACATAGATCGTTAAGCAACTATGTC (SEQ ID NO: 39) |
| | Forward Primer 2 (allele Y) | CTGAACATAGATCGTTAAGCAACTATGTA (SEQ ID NO: 40) |
| | Reverse Primer | CTTCACATCACCGATTCTCAAATTCTCTT (SEQ ID NO: 41) |
| SNP 6 | Forward Primer 1 (allele X) | TGATCTTTATCTATTTCCTTTTAAGACAACAT (SEQ ID NO: 42) |
| | Forward Primer 2 (allele Y) | GATCTTTATCTATTTCCTTTTAAGACAACAG (SEQ ID NO: 43) |
| | Reverse Primer | GCAGTTCCTTCTGACACATTACAAGATTA (SEQ ID NO: 44) |
| SNP 7 | Forward Primer 1 (allele X) | AGGTTTTGATGAAAATATGCTTATTGATGG (SEQ ID NO: 45) |
| | Forward Primer 2 (allele Y) | ATAGGTTTTGATGAAAATATGCTTATTGATGT (SEQ ID NO: 46) |
| | Reverse Primer | ATGAGAGAACCTCTGCTAGGCACAA (SEQ ID NO: 47) |
| SNP 8 | Forward Primer 1 (allele X) | GTTTTCTAAGACTATGTTATTCTTGAGCG (SEQ ID NO: 48) |
| | Forward Primer 2 (allele Y) | GTTTTCTAAGACTATGTTATTCTTGAGCA (SEQ ID NO: 49) |
| | Reverse Primer | AAATAGACAAGGGTGAAATCTGAATGTGAT (SEQ ID NO: 50) |
| SNP 9 | Forward Primer 1 (allele X) | ACTCACTGCTCACTTCAGCTACTA (SEQ ID NO: 51) |
| | Forward Primer 2 (allele Y) | CTCACTGCTCACTTCAGCTACTG (SEQ ID NO: 52) |
| | Reverse Primer | CGGATTAATCGAAATGCAATCAAGCAGAA (SEQ ID NO: 53) |
| SNP 10 | Forward Primer 1 (allele X) | GAGATTCTCTAACTCGTGCGTACA (SEQ ID NO: 54) |
| | Forward Primer 2 (allele Y) | AGATTCTCTAACTCGTGCGTACG (SEQ ID NO: 55) |
| | Reverse Primer | GTTGGGTTTATTATCGGACCACTCATAAA (SEQ ID NO: 56) |

TABLE H-continued

KASP Primers for SNP 1 through SNP 13 Related to *P. vulgaris* Volatile Compounds

| SNP # | KASP Primers (target) | Nucleotide Sequence (5' to 3') |
|---|---|---|
| SNP 11 | Forward Primer 1 (allele X) | ACGTTTTGCCAAATTTATGGTGCAAATTT (SEQ ID NO: 57) |
| | Forward Primer 2 (allele Y) | CGTTTTGCCAAATTTATGGTGCAAATTC (SEQ ID NO: 58) |
| | Reverse Primer | CCGGAGTAGGAGAGAAATTTTGGAAAATT (SEQ ID NO: 59) |
| SNP 12 | Forward Primer 1 (allele X) | CATACAAATAATATAACTTTTAAGGATCCAAT (SEQ ID NO: 60) |
| | Forward Primer 2 (allele Y) | CATACAAATAATATAACTTTTAAGGATCCAAG (SEQ ID NO: 61) |
| | Reverse Primer | GGCCACATATAGAATATCATCTGCATCTA (SEQ ID NO: 62) |
| SNP 13 | Forward Primer 1 (allele X) | CTGGTTAAATTCTCCTTGTCTTAGC (SEQ ID NO: 63) |
| | Forward Primer 2 (allele Y) | GTCTGGTTAAATTCTCCTTGTCTTAGA (SEQ ID NO: 64) |
| | Reverse Primer | TGCAGCAACATGGATAGTACCCCAA (SEQ ID NO: 65) |

Shown in TABLE I are the BLAST® searches in Phytozome, *Phaseolus vulgaris*, v2.1, for both competitive primers, i.e., forward primers 1 and 2, for each SNP locus. Only one of the two forward primers directly matches the target SNP in the sequence in the Phytozome, *Phaseolus vulgaris*, v2.1, genome and the alternative primer contains a mismatch to the genome at the 3' end of the primer. Other common bean (*Phaseolus vulgaris*) genomes not shown in Phytozome, *Phaseolus vulgaris*, v2.1, can contain the alternative SNP and will match the alternative forward primer that mismatches the Phytozome, *Phaseolus vulgaris*, v2.1, genome. The BLAST® searches matching to the (+) strand of the genome will match one additional nucleotide downstream representing the 3' end of the primer where the SNP is located. The BLAST® searches matching to the (−) strand of the genome will match one additional nucleotide upstream representing the 3' end of the primer where the SNP is located. This difference in BLAST® matches to the Phytozome, *Phaseolus vulgaris*, v2.1, genome demonstrating the competitive nature of the KASP reaction in which only one primer matches at the 3' end to the particular genomic DNA included in the KASP reaction.

TABLE I

BLAST ® Matches (Phytozome, *P. vulgaris*, v2.1) for KASP Forward Primers for SNP 1 through SNP 13

| SNP # | KASP Forward Primers | BLAST ® Match (Phytozome, *P. vulgaris*, v2.1) for KASP Primer (allele) |
|---|---|---|
| SNP 1 | Primer 1 (5'→3') | TTCTACTTTGAATATTAAGATTCATGTGCATT (SEQ ID NO: 66) |
| | | Chr. 1: 2939690 . . . 2939721 (−) strand class = match length = 32 bp (X) |
| | Primer 2 (5'→3') | CTACTTTGAATATTAAGATTCATGTGCAT (SEQ ID NO: 67) |
| | | Chr. 1: 2939691 . . . 2939719 (−) strand class = match length = 29 bp (Y) |
| SNP 2 | Primer 1 (5'→3') | GTAATCATATTCAAATAAGTTTTATTTATTCA (SEQ ID NO: 68) |
| | | Chr. 8: 53768384 . . . 53768415 (−) strand class = match length = 32 bp (X) |
| | Primer 2 (5'→3') | GTAATCATATTCAAATAAGTTTTATTTATTCAA (SEQ ID NO: 69) |
| | | Chr. 8: 53768383 . . . 53768415 (−) strand class = match_part length = 33 bp (Y) |
| SNP 3 | Primer 1 (5'→3') | GTAAGATGACCTTCTGAAGGAACTGA (SEQ ID NO: 70) |
| | | Chr. 6: 14800647 . . . 14800672 (+) strand class = match length = 26 bp (X) |
| | Primer 2 (5'→3') | AAGATGACCTTCTGAAGGAACTG (SEQ ID NO: 71) |
| | | Chr. 6: 14800649 . . . 14800671 (+) strand class = match length = 23 bp (Y) |
| SNP 4 | Primer 1 (5'→3') | ACTATTTACAGAGCATAAGTGGATTCTT (SEQ ID NO: 72) |
| | | Chr. 2: 47396313 . . . 47396340 (+) strand class = match_part length = 28 bp (X) |
| | Primer 2 (5'→3') | CTATTTACAGAGCATAAGTGGATTCTTC (SEQ ID NO: 73) |
| | | Chr. 2: 47396314 . . . 47396341 (+) strand class = match length = 28 bp (Y) |
| SNP 5 | Primer 1 (5'→3') | GAACATAGATCGTTAAGCAACTATGTC (SEQ ID NO: 74) |
| | | Chr. 2: 19725396 . . . 19725422 (−) strand class = match length = 27 bp (X) |
| | Primer 2 (5'→3') | CTGAACATAGATCGTTAAGCAACTATGT (SEQ ID NO: 75) |
| | | Chr. 2: 19725397 . . . 19725424 (−) strand class = match_part length = 28 bp (Y) |

TABLE I-continued

BLAST ® Matches (Phytozome, *P. vulgaris*, v2.1) for KASP Forward Primers for SNP 1 through SNP 13

| SNP # | KASP Forward Primers | BLAST ® Match (Phytozome, *P. vulgaris*, v2.1) for KASP Primer (allele) |
|---|---|---|
| SNP 6 | Primer 1(5'→3') | TGATCTTTATCTATTTCCTTTTAAGACAACAT (SEQ ID NO: 76)<br>Chr. 7: 39538212 . . . 39538243 (-) strand class = match length = 32 bp (X) |
|  | Primer 2(5'→3') | GATCTTTATCTATTTCCTTTTAAGACAACA (SEQ ID NO: 77)<br>Chr. 7: 39538213 . . . 39538242 (-strand) class = match length = 30 bp (Y) |
| SNP 7 | Primer 1(5'→3') | AGGTTTTGATGAAAATATGCTTATTGATGG (SEQ ID NO: 78)<br>Chr 7: 32623478 . . . 32623507 (-) strand class = match length = 30 bp (X) |
|  | Primer 2(5'→3') | ATAGGTTTTGATGAAAATATGCTTATTGATG (SEQ ID NO: 79)<br>Chr. 7: 32623479 . . . 32623509 (-) strand class = match length = 31 bp (Y) |
| SNP 8 | Primer 1(5'→3') | GTTTTCTAAGACTATGTTATTCTTGAGC (SEQ ID NO: 80)<br>Chr. 3: 44170091 . . . 44170118 (+) strand class = match length = 28 bp (X) |
|  | Primer 2(5'→3') | GTTTTCTAAGACTATGTTATTCTTGAGCA (SEQ ID NO: 81)<br>Chr. 3: 44170091 . . . 44170119 (+) strand class = match length = 29 bp (Y) |
| SNP 9 | Primer 1(5'→3') | ACTCACTGCTCACTTCAGCTACTA (SEQ ID NO: 82)<br>Chr. 3: 32906019 . . . 32906042 (-) strand class = match length = 24 bp (X) |
|  | Primer 2(5'→3') | CTCACTGCTCACTTCAGCTACT (SEQ ID NO: 83)<br>Chr. 3: 32906020 . . . 32906041 (-) strand class = match length = 22 bp (Y) |
| SNP 10 | Primer 1(5'→3') | GAGATTCTCTAACTCGTGCGTAC (SEQ ID NO: 84)<br>Chr. 8: 54970430 . . . 54970452 (-) strand class = match length = 23 bp (X) |
|  | Primer 2(5'→3') | AGATTCTCTAACTCGTGCGTACG (SEQ ID NO: 85)<br>Chr. 8: 54970429 . . . 54970451 (-) strand class = match_part length = 23 bp (Y) |
| SNP 11 | Primer 1(5'→3') | ACGTTTTGCCAAATTTATGGTGCAAATTT (SEQ ID NO: 86)<br>Chr. 11: 51964679 . . . 51964707 (+) strand class = match length = 29 bp (X) |
|  | Primer 2(5'→3') | CGTTTTGCCAAATTTATGGTGCAAATT (SEQ ID NO: 87)<br>Chr. 11: 51964680 . . . 51964706 (+) strand class = match length = 27 bp (Y) |
| SNP 12 | Primer 1(5'→3') | CATACAAATAATATAACTTTTAAGGATCCAA (SEQ ID NO: 88)<br>Chr. 2: 729616 . . . 729646 (-) strand class = match length = 31 bp (X) |
|  | Primer 2(5'→3') | CATACAAATAATATAACTTTTAAGGATCCAAG (SEQ ID NO: 89)<br>Chr. 2: 729615 . . . 729646 (-) strand class = match_part length = 32 bp (Y) |
| SNP 13 | Primer 1(5'→3') | CTGGTTAAATTCTCCTTGTCTTAGC (SEQ ID NO: 90)<br>Chr. 7: 18092158 . . . 18092182 (+) strand class = match length = 25 bp (X) |
|  | Primer 2(5'→3') | GTCTGGTTAAATTCTCCTTGTCTTAG (SEQ ID NO: 91)<br>Chr. 7: 18092156 . . . 18092181 (+) strand class = match_part length = 26 bp (Y) |

Referring to FIGS. 10-22 and TABLES J-V, the verification analysis of the SNP-specific KASP primers indicated that SNP 1, SNP 2, and SNP 3 are molecular markers for phenotypic expression of 3-hexen-1-ol; SNP 4, SNP 5, and SNP 6 are molecular markers for phenotypic expression of 1-octen-3-ol; SNP 7 is a molecular marker for phenotypic expression of linalool, SNP 8 and SNP 9 are molecular markers for phenotypic expression of 1-penten-3-ol; SNP 10 and SNP 11 are molecular markers for phenotypic expression of 1-hexanol; and SNP 12 and SNP 13 are molecular markers for phenotypic expression of β-ionone, all of which can be used in marker assisted identification and selection of common beans during breeding.

TABLE J

Validation Data for SNP 1 showing KASP Assay Results for FAM-labeled forward primer and HEX-labeled forward primer plotted in FIG. 10.

| Line | Source | X Axis | Y Axis |
|---|---|---|---|
| 91-1009 | Dickson Collection | 0.5984 | 0.88198 |
| 91-1028 | Dickson Collection | 0.2485 | 6.97081 |
| 91-1033B | Dickson Collection | 3.09628 | 1.11368 |
| 91-1145 | Dickson Collection | 0.24648 | 6.18636 |
| 91-1542 | Dickson Collection | 0.24537 | 6.4671 |
| 91-1643 | Dickson Collection | 0.27128 | 6.95263 |
| 91-1672 | Dickson Collection | 3.87982 | 1.11097 |
| 91-1728 | Dickson Collection | 0.66187 | 0.82435 |
| 91-1748 | Dickson Collection | 0.25121 | 7.35657 |
| 91-1750 | Dickson Collection | 0.28005 | 7.49073 |
| 91-1755 | Dickson Collection | 0.29119 | 5.43132 |
| 91-1759 | Dickson Collection | 0.5969 | 0.79968 |
| 91-1768 | Dickson Collection | 0.25641 | 5.63979 |
| 91-1976 | Dickson Collection | 0.21813 | 7.33254 |
| 91-2100 | Dickson Collection | 0.22989 | 6.74217 |
| 91-3346 | Dickson Collection | 0.26193 | 5.34192 |
| 91-3915 | Dickson Collection | 0.64774 | 0.76598 |
| 91-3918 | Dickson Collection | 0.65006 | 0.90608 |
| 91-3921 | Dickson Collection | 0.58251 | 0.91237 |
| Acclaim | Seminis | 4.23818 | 1.20249 |
| Aunt Ada | Turtle Tree Seed | 4.25325 | 1.22334 |
| B-1 | SerinXOregon5630 cross, F6 | 4.35606 | 1.3153 |
| B-15 | SerinXOregon5630 cross, F6 | 4.61934 | 1.25824 |
| B-28 | SerinXOregon5630 cross, F6 | 4.54766 | 1.2908 |
| B-36 | SerinXOregon5630 cross, F6 | 4.44619 | 1.23425 |

TABLE J-continued

Validation Data for SNP 1 showing KASP Assay Results for FAM-labeled forward primer and HEX-labeled forward primer plotted in FIG. 10.

| Line | Source | X Axis | Y Axis |
|---|---|---|---|
| B-37 | SerinXOregon5630 cross, F6 | 4.32529 | 1.16651 |
| B-38 | SerinXOregon5630 cross, F6 | 4.07886 | 1.15227 |
| B-41 | SerinXOregon5630 cross, F6 | 3.97587 | 1.20697 |
| B-42 | SerinXOregon5630 cross, F6 | 4.81584 | 1.14923 |
| BBL274 | Seminis | 4.25972 | 1.38086 |
| Benchmark | Syngenta | 4.25133 | 1.30206 |
| Booster | Syngenta | 4.17579 | 1.16724 |
| Calgreen | Syngenta | 0.62319 | 0.80559 |
| Castano | Syngenta | 4.51889 | 1.3394 |
| Coloma | Syngenta | 4.39793 | 1.18468 |
| Control 1 | No template controls | 0.40978 | 0.84356 |
| Control 2 | No template controls | 0.37827 | 0.75451 |
| Cosse Violette | Amishland Heirloom Seeds | 0.21266 | 6.70772 |
| Cyclone | Seminis | 4.01764 | 1.10299 |
| Flavor Sweet | Harris Moran | 4.19122 | 1.281 |
| FM1 Pole Blue | USDA collection: Ferry-Morse | 0.68506 | 0.86505 |
| Fortex | Oregon State University | 4.24477 | 1.12112 |
| Hidatsa Shield | Seed Savers Exchange | 4.65192 | 1.39007 |
| Kentucky Wonder | Syngenta | 0.27717 | 7.53372 |
| Mercury | Syngenta | 4.36642 | 1.31662 |
| New Mex Cave | Peace Seedlings | 0.26555 | 7.20314 |
| PHA0008 | Misiòn Biològica de Galicia-CSIC | 3.17102 | 1.02867 |
| PHA0112 | Misiòn Biològica de Galicia-CSIC | 3.15155 | 0.97708 |
| PHA0192 | Misiòn Biològica de Galicia-CSIC | 3.42415 | 1.078 |
| PHA0315 | Misiòn Biològica de Galicia-CSIC | 0.75644 | 0.85514 |
| Swiss Landfrauen | Amishland Heirloom Seeds | 2.93981 | 0.8578 |

TABLE K

Figure 11:
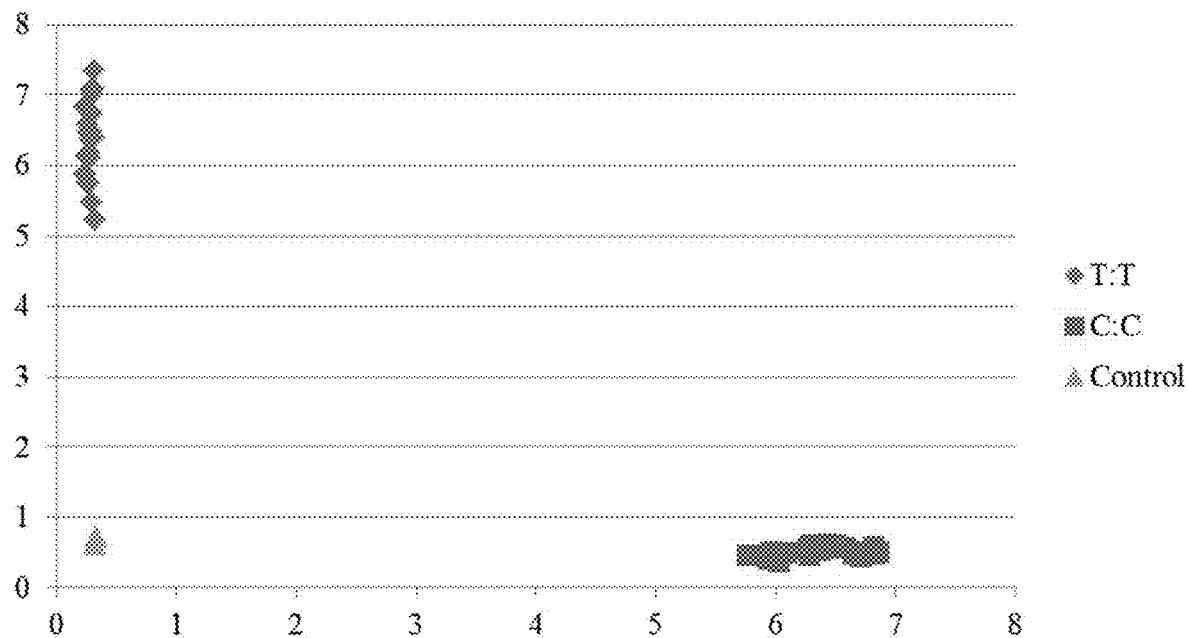
FIG. 11 illustrates a cluster (Cartesian) plot of fluorescent signals reporting each individual DNA sample obtained from a bean line (see, TABLE K) having SNP 2. The FAM fluorescence value associated with the FAM-labelled oligo sequence (FAM-labeled primer) is plotted on the X axis. The data points plotted close to the X axis represent high FAM signal and no HEX signal generated during the KASP reaction, and the related bean line samples (see, TABLE K), are homozygous for the allele reported by FAM, i.e., C. The HEX fluorescence value associated with the HEX-labelled oligo sequence (HEX-labeled primer) is plotted on the Y axis. The data points plotted close to the Y axis represent high HEX signal and no FAM signal generated during the KASP reaction, and the related bean line samples (see, TABLE K), are homozygous for the allele reported by HEX, i.e., T. The KASP reaction without any template DNA, i.e., no template control (NTC), is included as a negative control to ensure reliability and did not generate any fluorescence, and the data point is plotted at the origin.

Validation Data for SNP 2 showing KASP Assay Results for FAM-labeled forward primer and HEX-labeled forward primer plotted in FIG. 11.

| Line | Source | X Axis | Y Axis |
|---|---|---|---|
| 91-1009 | Dickson Collection | 0.29319 | 7.01143 |
| 91-1028 | Dickson Collection | 6.81403 | 0.59125 |
| 91-1033B | Dickson Collection | 0.28515 | 6.74703 |
| 91-1145 | Dickson Collection | 0.25597 | 6.59835 |
| 91-1542 | Dickson Collection | 0.28359 | 6.72257 |
| 91-1643 | Dickson Collection | 0.25569 | 5.74914 |
| 91-1672 | Dickson Collection | 6.50355 | 0.60881 |
| 91-1728 | Dickson Collection | 5.76201 | 0.46198 |
| 91-1748 | Dickson Collection | 0.28565 | 5.48493 |
| 91-1750 | Dickson Collection | 6.85853 | 0.51802 |
| 91-1755 | Dickson Collection | 0.32093 | 5.23192 |
| 91-1759 | Dickson Collection | 0.27394 | 6.12704 |
| 91-1768 | Dickson Collection | 6.28585 | 0.57643 |
| 91-1976 | Dickson Collection | 5.94292 | 0.40144 |
| 91-2100 | Dickson Collection | 0.27758 | 6.10905 |
| 91-3346 | Dickson Collection | 6.65692 | 0.50695 |
| 91-3915 | Dickson Collection | 6.08316 | 0.49083 |
| 91-3918 | Dickson Collection | 6.35787 | 0.52145 |
| 91-3921 | Dickson Collection | 6.71162 | 0.44488 |
| Acclaim | Seminis | 0.26953 | 5.74789 |
| Aunt Ada | Turtle Tree Seed | 0.25349 | 6.46159 |
| B-1 | SerinXOregon5630 cross, F6 | 6.4875 | 0.55701 |
| B-15 | SerinXOregon5630 cross, F6 | 6.34296 | 0.55454 |
| B-28 | SerinXOregon5630 cross, F6 | 5.96443 | 0.51123 |
| B-36 | SerinXOregon5630 cross, F6 | 6.267 | 0.56833 |
| B-37 | SerinXOregon5630 cross, F6 | 5.91607 | 0.43314 |
| B-38 | SerinXOregon5630 cross, F6 | 6.65012 | 0.47095 |
| B-41 | SerinXOregon5630 cross, F6 | 6.44948 | 0.57662 |
| B-42 | SerinXOregon5630 cross, F6 | 6.42705 | 0.62728 |
| BBL274 | Seminis | 0.25178 | 6.12088 |
| Benchmark | Syngenta | 6.0284 | 0.37332 |
| Booster | Syngenta | 6.4741 | 0.57329 |
| Calgreen | Syngenta | 0.29093 | 6.49088 |
| Castano | Syngenta | 0.27743 | 6.35964 |
| Coloma | Syngenta | 6.29138 | 0.59675 |
| Control 1 | No template controls | 0.33015 | 0.73083 |

TABLE K-continued

Validation Data for SNP 2 showing KASP Assay Results for FAM-labeled forward primer and HEX-labeled forward primer plotted in FIG. 11.

| Line | Source | X Axis | Y Axis |
|---|---|---|---|
| Control 2 | No template controls | 0.32355 | 0.62311 |
| Cosse Violette | Amishland Heirloom Seeds | 6.2704 | 0.55426 |
| Cyclone | Seminis | 0.23297 | 5.87261 |
| Flavor Sweet | Harris Moran | 0.24444 | 6.1306 |
| FM1 Pole Blue | USDA collection: Ferry-Morse | 5.87769 | 0.45884 |
| Fortex | Oregon State University | 6.57518 | 0.57293 |
| Hidatsa Shield | Seed Savers Exchange | 0.30698 | 6.4008 |
| Kentucky Wonder | Syngenta | 6.27795 | 0.46426 |
| Mercury | Syngenta | 0.2382 | 6.82793 |
| New Mex Cave | Peace Seedlings | 0.30589 | 7.35067 |
| PHA0008 | Misiòn Biològica de Galicia - CSIC | 0.27793 | 6.75335 |
| PHA0112 | Misiòn Biològica de Galicia - CSIC | 0.27134 | 6.17377 |
| PHA0192 | Misiòn Biològica de Galicia - CSIC | 0.30926 | 7.0966 |
| PHA0315 | Misiòn Biològica de Galicia - CSIC | 6.83179 | 0.47429 |
| Swiss Landfrauen | Amishland Heirloom Seeds | 0.28669 | 7.05639 |

TABLE L

Figure 12:
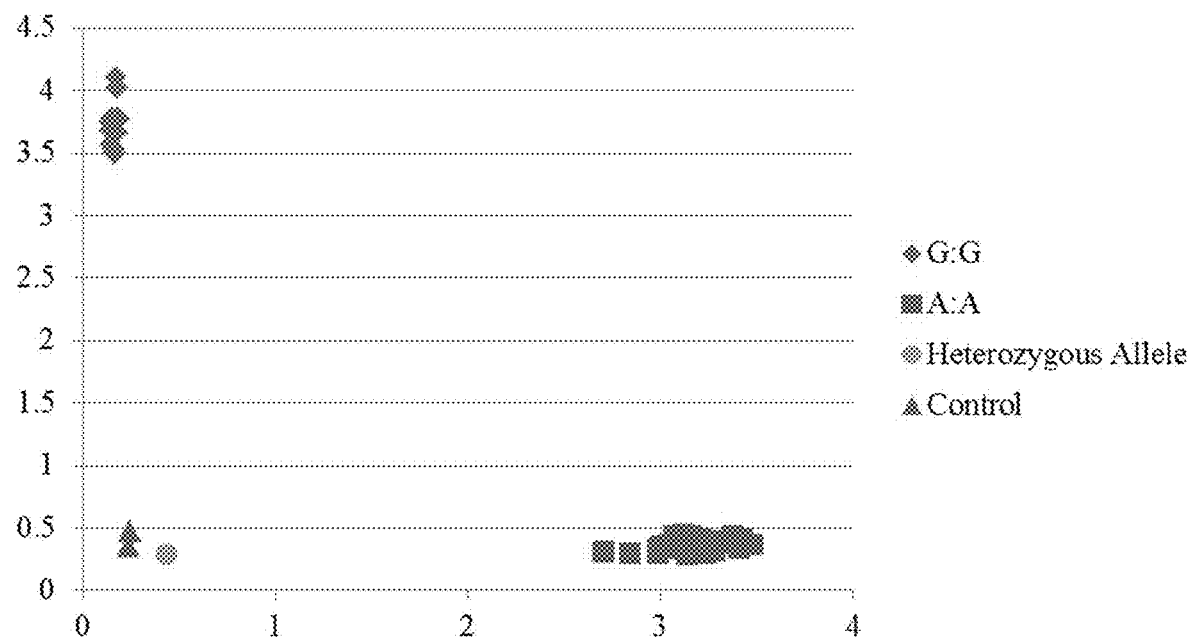
FIG. 12 illustrates a cluster (Cartesian) plot of fluorescent signals reporting each individual DNA sample obtained from a bean line (see, TABLE L) having SNP 3. The FAM fluorescence value associated with the FAM-labelled oligo sequence (FAM-labeled primer) is plotted on the X axis. The data points plotted close to the X axis represent high FAM signal and no HEX signal generated during the KASP reaction, and the related bean line samples (see, TABLE L), are homozygous for the allele reported by FAM, i.e., A. The HEX fluorescence value associated with the HEX-labelled oligo sequence (HEX-labeled primer) is plotted on the Y axis. The data points plotted close to the Y axis represent high HEX signal and no FAM signal generated during the KASP reaction, and the related bean line samples (see, TABLE L), are homozygous for the allele reported by HEX, i.e., G. A sample that is heterozygous contains both the allele reported by FAM and the allele reported by HEX and generated half as much FAM fluorescence and half as much HEX fluorescence in comparison to the samples that are homozygous for these alleles. This data point is plotted in the center of the plot, representing half FAM signal and half HEX signal. The KASP reaction without any template DNA, i.e., no template control (NTC), is included as a negative control to ensure reliability and did not generate any fluorescence, and the data point is plotted at the origin.

Validation Data for SNP 3 showing KASP Assay Results for FAM-labeled forward primer and HEX-labeled forward primer plotted in FIG. 12.

| Line | Source | X Axis | Y Axis |
|---|---|---|---|
| 91-1009 | Dickson Collection | 2.98932 | 0.3285 |
| 91-1028 | Dickson Collection | 0.43651 | 0.28611 |
| 91-1033B | Dickson Collection | 2.98719 | 0.30108 |
| 91-1145 | Dickson Collection | 3.13163 | 0.39918 |
| 91-1542 | Dickson Collection | 3.00643 | 0.35077 |
| 91-1643 | Dickson Collection | 2.70497 | 0.30639 |
| 91-1672 | Dickson Collection | 3.19626 | 0.2941 |
| 91-1728 | Dickson Collection | 3.05219 | 0.34021 |
| 91-1748 | Dickson Collection | 3.24047 | 0.35076 |
| 91-1750 | Dickson Collection | 3.11948 | 0.32518 |
| 91-1755 | Dickson Collection | 3.30006 | 0.39477 |
| 91-1759 | Dickson Collection | 2.84278 | 0.30122 |
| 91-1768 | Dickson Collection | 3.04282 | 0.3667 |
| 91-1976 | Dickson Collection | 3.21056 | 0.36774 |
| 91-2100 | Dickson Collection | 3.03259 | 0.33871 |
| 91-3346 | Dickson Collection | 3.05135 | 0.34813 |
| 91-3915 | Dickson Collection | 3.37135 | 0.44231 |
| 91-3918 | Dickson Collection | 3.40823 | 0.34219 |
| 91-3921 | Dickson Collection | 3.28515 | 0.31545 |
| Acclaim | Seminis | 0.15562 | 3.77654 |
| Aunt Ada | Turtle Tree Seed | 0.14983 | 3.57109 |
| B-1 | SerinXOregon5630 cross, F6 | 3.20797 | 0.42282 |
| B-15 | SerinXOregon5630 cross, F6 | 3.30078 | 0.39686 |
| B-28 | SerinXOregon5630 cross, F6 | 3.07062 | 0.43455 |
| B-36 | SerinXOregon5630 cross, F6 | 3.42957 | 0.42057 |
| B-37 | SerinXOregon5630 cross, F6 | 3.18097 | 0.3784 |
| B-38 | SerinXOregon5630 cross, F6 | 3.48032 | 0.37309 |
| B-41 | SerinXOregon5630 cross, F6 | 3.07163 | 0.34579 |
| B-42 | SerinXOregon5630 cross, F6 | 3.19652 | 0.37967 |
| BBL274 | Seminis | 0.16498 | 3.49217 |
| Benchmark | Syngenta | 3.15655 | 0.43871 |
| Booster | Syngenta | 3.23821 | 0.3029 |
| Calgreen | Syngenta | 0.15016 | 3.73407 |
| Castano | Syngenta | 3.27674 | 0.37297 |
| Coloma | Syngenta | 3.14359 | 0.41912 |
| Control 1 | No template controls | 0.24036 | 0.3528 |
| Control 2 | No template controls | 0.24316 | 0.47039 |
| Cosse Violette | Amishland Heirloom Seeds | 3.18613 | 0.37845 |
| Cyclone | Seminis | 0.15848 | 3.73606 |
| Flavor Sweet | Harris Moran | 0.1805 | 3.66036 |
| FM1 Pole Blue | USDA collection: Ferry-Morse | 3.11624 | 0.45069 |
| Fortex | Oregon State University | 3.23457 | 0.29483 |
| Hidatsa Shield | Seed Savers Exchange | 0.17127 | 4.09833 |
| Kentucky Wonder | Syngenta | 3.13497 | 0.28965 |

TABLE L-continued

Validation Data for SNP 3 showing KASP Assay Results for FAM-labeled forward primer and HEX-labeled forward primer plotted in FIG. 12.

| Line | Source | X Axis | Y Axis |
| --- | --- | --- | --- |
| Mercury | Syngenta | 0.19326 | 3.7665 |
| New Mex Cave | Peace Seedlings | 3.10607 | 0.36884 |
| PHA0008 | Misión Biológica de Galicia - CSIC | 0.18084 | 3.77493 |
| PHA0112 | Misión Biológica de Galicia - CSIC | 0.16705 | 3.5292 |
| PHA0192 | Misión Biológica de Galicia - CSIC | 0.14679 | 3.67822 |
| PHA0315 | Misión Biológica de Galicia - CSIC | 3.29994 | 0.37572 |
| Swiss Landfrauen | Amishland Heirloom Seeds | 0.18331 | 4.02182 |

TABLE M

Figure 13:
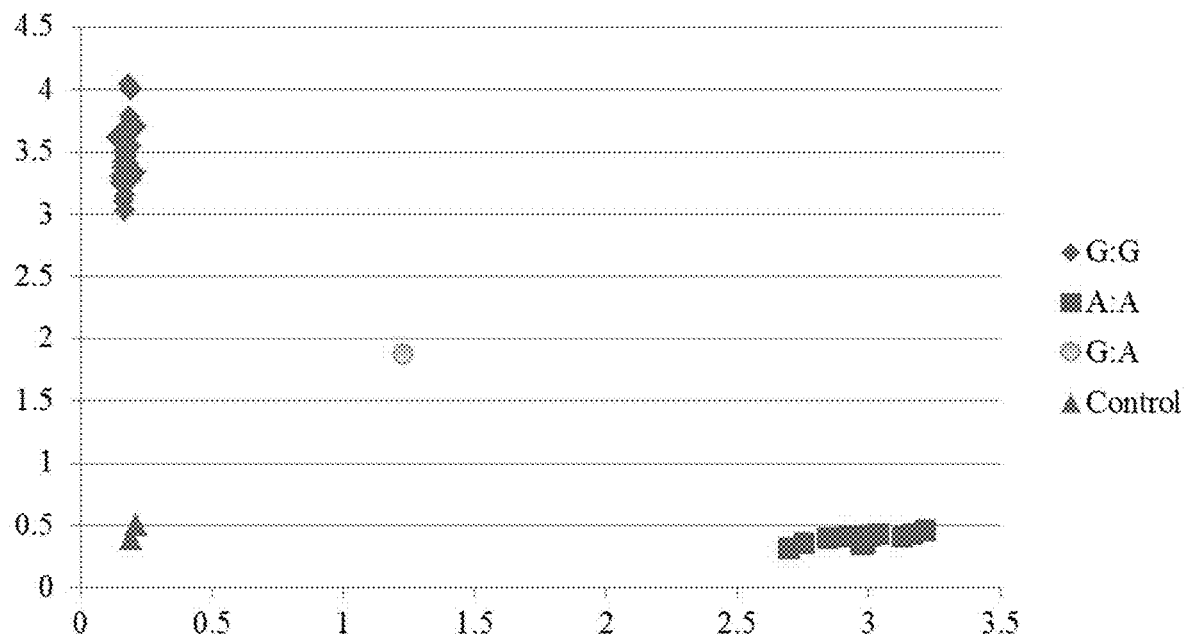
FIG. 13 illustrates a cluster (Cartesian) plot of fluorescent signals reporting each individual DNA sample obtained from a bean line (see, TABLE M) having SNP 4. The FAM fluorescence value associated with the FAM-labelled oligo sequence (FAM-labeled primer) is plotted on the X axis. The data points plotted close to the X axis represent high FAM signal and no HEX signal generated during the KASP reaction, and the related bean line samples (see, TABLE M), are homozygous for the allele reported by FAM, i.e., A. The HEX fluorescence value associated with the HEX-labelled oligo sequence (HEX-labeled primer) is plotted on the Y axis. The data points plotted close to the Y axis represent high HEX signal and no FAM signal generated during the KASP reaction, and the related bean line samples (see, TABLE M), are homozygous for the allele reported by HEX, i.e., G. A sample that is heterozygous contains both the allele reported by FAM and the allele reported by HEX and generated half as much FAM fluorescence and half as much HEX fluorescence in comparison to the samples that are homozygous for these alleles. This data point is plotted in the center of the plot, representing half FAM signal and half HEX signal. The KASP reaction without any template DNA, i.e., no template control (NTC), is included as a negative control to ensure reliability and did not generate any fluorescence, and the data point is plotted at the origin.

Validation Data for SNP 4 showing KASP Assay Results for FAM-labeled forward primer and HEX-labeled forward primer plotted in FIG. 13.

| Line | Source | X Axis | Y Axis |
| --- | --- | --- | --- |
| 91-1009 | Dickson Collection | 0.17222 | 3.50639 |
| 91-1028 | Dickson Collection | 1.22472 | 1.87659 |
| 91-1033B | Dickson Collection | 2.69721 | 0.31681 |
| 91-1145 | Dickson Collection | 0.16015 | 3.5935 |
| 91-1542 | Dickson Collection | 2.98447 | 0.35635 |
| 91-1643 | Dickson Collection | 2.96826 | 0.36478 |
| 91-1672 | Dickson Collection | 0.19272 | 4.0013 |
| 91-1728 | Dickson Collection | 0.16647 | 3.29102 |
| 91-1748 | Dickson Collection | 2.97397 | 0.34541 |
| 91-1750 | Dickson Collection | 3.16403 | 0.42817 |
| 91-1755 | Dickson Collection | 3.00646 | 0.41515 |
| 91-1759 | Dickson Collection | 2.75208 | 0.3599 |
| 91-1768 | Dickson Collection | 0.1753 | 3.61914 |
| 91-1976 | Dickson Collection | 2.84263 | 0.40259 |
| 91-2100 | Dickson Collection | 2.92402 | 0.40737 |
| 91-3346 | Dickson Collection | 3.21152 | 0.45493 |
| 91-3915 | Dickson Collection | 0.17437 | 3.3834 |
| 91-3918 | Dickson Collection | 0.19923 | 3.67364 |
| 91-3921 | Dickson Collection | 3.12925 | 0.40572 |
| Acclaim | Seminis | 0.18378 | 3.3166 |
| Aunt Ada | Turtle Tree Seed | 0.18876 | 3.5422 |
| B-1 | SerinXOregon5630 cross, F6 | 0.1866 | 4.04061 |
| B-15 | SerinXOregon5630 cross, F6 | 0.1779 | 3.5642 |
| B-28 | SerinXOregon5630 cross, F6 | 0.17825 | 3.51778 |
| B-36 | SerinXOregon5630 cross, F6 | 0.16945 | 3.02893 |
| B-37 | SerinXOregon5630 cross, F6 | 0.15464 | 3.30279 |
| B-38 | SerinXOregon5630 cross, F6 | 0.21011 | 3.33611 |
| B-41 | SerinXOregon5630 cross, F6 | 0.17183 | 3.57557 |
| B-42 | SerinXOregon5630 cross, F6 | 0.19133 | 3.78311 |
| BBL274 | Seminis | 0.16706 | 3.37157 |
| Benchmark | Syngenta | 0.17315 | 3.45924 |
| Booster | Syngenta | 0.17243 | 3.15514 |
| Calgreen | Syngenta | 0.17138 | 3.63631 |
| Castano | Syngenta | 0.14314 | 3.62095 |
| Coloma | Syngenta | 0.15486 | 3.25215 |
| Control 1 | No template controls | 0.21104 | 0.49981 |
| Control 2 | No template controls | 0.19332 | 0.38639 |
| Cosse Violette | Amishland Heirloom Seeds | 0.1842 | 3.66039 |
| Cyclone | Seminis | 0.16706 | 3.09727 |
| Flavor Sweet | Harris Moran | 0.1937 | 3.28372 |
| FM1 Pole Blue | USDA collection: Ferry-Morse | 0.16757 | 3.41375 |
| Fortex | Oregon State University | 0.21284 | 3.70081 |
| Hidatsa Shield | Seed Savers Exchange | 3.03461 | 0.42523 |
| Kentucky Wonder | Syngenta | 0.17115 | 3.48536 |
| Mercury | Syngenta | 0.18223 | 3.63484 |
| New Mex Cave | Peace Seedlings | 0.17183 | 3.59578 |
| PHA0008 | Misión Biológica de Galicia - CSIC | 0.16728 | 3.28031 |
| PHA0112 | Misión Biológica de Galicia - CSIC | 0.17995 | 3.40306 |
| PHA0192 | Misión Biológica de Galicia - CSIC | 0.18136 | 3.70846 |
| PHA0315 | Misión Biológica de Galicia - CSIC | 0.17255 | 3.55225 |
| Swiss Landfrauen | Amishland Heirloom Seeds | 0.17362 | 3.48291 |

TABLE N

Figure 14:
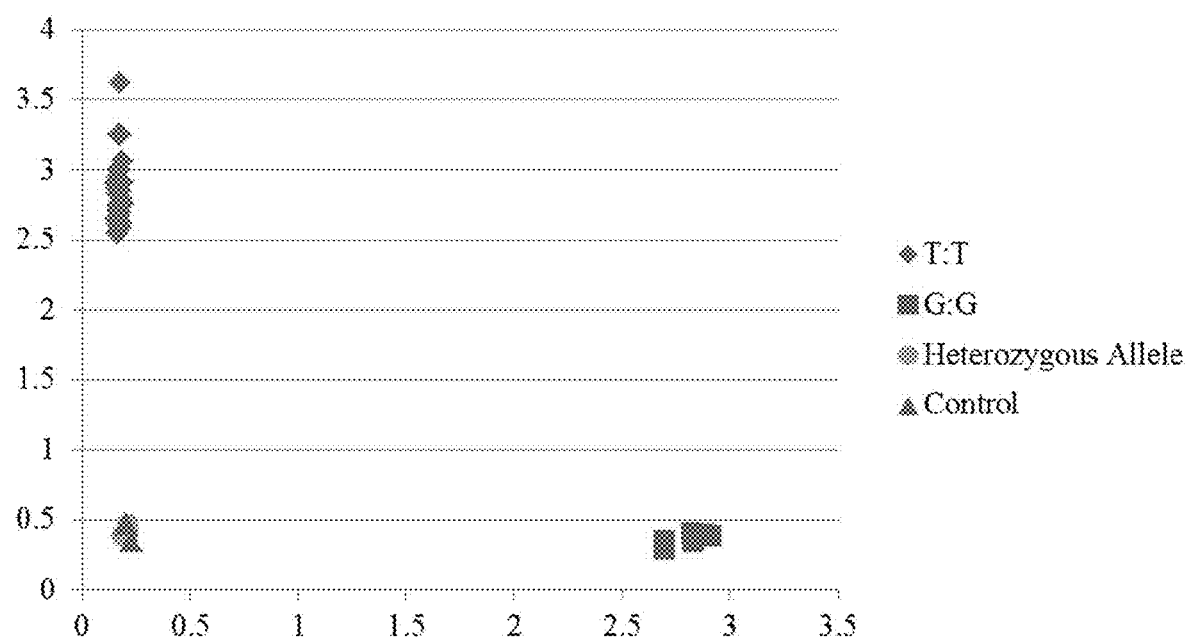
FIG. 14 illustrates a cluster (Cartesian) plot of fluorescent signals reporting each individual DNA sample obtained from a bean line (see, TABLE N) having SNP 5. The FAM fluorescence value associated with the FAM-labelled oligo sequence (FAM-labeled primer) is plotted on the X axis. The data points plotted close to the X axis represent high FAM signal and no HEX signal generated during the KASP reaction, and the related bean line samples (see, TABLE N), are homozygous for the allele reported by FAM, i.e., G. The HEX fluorescence value associated with the HEX-labelled oligo sequence (HEX-labeled primer) is plotted on the Y axis. The data points plotted close to the Y axis represent high HEX signal and no FAM signal generated during the KASP reaction, and the related bean line samples (see, TABLE N), are homozygous for the allele reported by HEX, i.e., T. A sample that is heterozygous contains both the allele reported by FAM and the allele reported by HEX and generated half as much FAM fluorescence and half as much HEX fluorescence in comparison to the samples that are homozygous for these alleles. This data point is plotted in the center of the plot, representing half FAM signal and half HEX signal. The KASP reaction without any template DNA, i.e., no template control (NTC), is included as a negative control to ensure reliability and did not generate any fluorescence, and the data point is plotted at the origin.

Validation Data for SNP 5 showing KASP Assay Results for FAM-labeled forward primer and HEX-labeled forward primer plotted in FIG. 14.

| Line | Source | X Axis | Y Axis |
| --- | --- | --- | --- |
| 91-1009 | Dickson Collection | 2.69464 | 0.29558 |
| 91-1028 | Dickson Collection | 0.18103 | 0.39386 |
| 91-1033B | Dickson Collection | 2.69506 | 0.35482 |
| 91-1145 | Dickson Collection | 0.21512 | 0.46795 |
| 91-1542 | Dickson Collection | 0.16745 | 2.86661 |
| 91-1643 | Dickson Collection | 0.16566 | 2.74874 |
| 91-1672 | Dickson Collection | 0.21559 | 0.42329 |
| 91-1728 | Dickson Collection | 0.16324 | 2.94317 |
| 91-1748 | Dickson Collection | 0.16989 | 2.72873 |
| 91-1750 | Dickson Collection | 0.16931 | 3.25066 |
| 91-1755 | Dickson Collection | 0.1943 | 2.9107 |
| 91-1759 | Dickson Collection | 0.17848 | 2.57813 |
| 91-1768 | Dickson Collection | 0.16813 | 3.00095 |
| 91-1976 | Dickson Collection | 0.18257 | 2.84894 |
| 91-2100 | Dickson Collection | 0.17449 | 2.66412 |
| 91-3346 | Dickson Collection | 0.17746 | 2.6926 |
| 91-3915 | Dickson Collection | 0.1688 | 2.7156 |
| 91-3918 | Dickson Collection | 0.17557 | 3.24658 |
| 91-3921 | Dickson Collection | 0.17101 | 2.87915 |
| Acclaim | Seminis | 0.17847 | 2.58831 |
| Aunt Ada | Turtle Tree Seed | 2.8206 | 0.40481 |
| B-1 | SerinXOregon5630 cross, F6 | 0.15415 | 2.90308 |
| B-15 | SerinXOregon5630 cross, F6 | 0.18201 | 3.25489 |
| B-28 | SerinXOregon5630 cross, F6 | 0.16887 | 2.99802 |
| B-36 | SerinXOregon5630 cross, F6 | 0.17836 | 2.99529 |
| B-37 | SerinXOregon5630 cross, F6 | 0.16778 | 2.86646 |
| B-38 | SerinXOregon5630 cross, F6 | 0.16776 | 2.54278 |
| B-41 | SerinXOregon5630 cross, F6 | 0.17196 | 2.62687 |
| B-42 | SerinXOregon5630 cross, F6 | 0.17529 | 3.62185 |
| BBL274 | Seminis | 0.17794 | 2.76165 |
| Benchmark | Syngenta | 0.16462 | 2.54611 |
| Booster | Syngenta | 0.1823 | 2.74354 |
| Calgreen | Syngenta | 0.1931 | 2.7569 |
| Castano | Syngenta | 0.18597 | 2.62432 |
| Coloma | Syngenta | 0.1761 | 2.7326 |
| Control 1 | No template controls | 0.22759 | 0.34804 |
| Control 2 | No template controls | 0.2079 | 0.46824 |
| Cosse Violette | Amishland Heirloom Seeds | 0.19172 | 3.06153 |
| Cyclone | Seminis | 0.17189 | 2.69337 |
| Flavor Sweet | Harris Moran | 0.18599 | 2.79518 |
| FM1 Pole Blue | USDA collection: Ferry-Morse | 0.17191 | 2.67397 |
| Fortex | Oregon State University | 0.16623 | 2.8278 |
| Hidatsa Shield | Seed Savers Exchange | 2.91142 | 0.38658 |
| Kentucky Wonder | Syngenta | 0.21148 | 0.39317 |
| Mercury | Syngenta | 0.15838 | 2.64976 |
| New Mex Cave | Peace Seedlings | 0.21477 | 0.44775 |
| PHA0008 | Misión Biológica de Galicia - CSIC | 2.88368 | 0.39792 |
| PHA0112 | Misión Biológica de Galicia - CSIC | 0.16359 | 2.60964 |
| PHA0192 | Misión Biológica de Galicia - CSIC | 2.82748 | 0.34163 |
| PHA0315 | Misión Biológica de Galicia - CSIC | 0.16915 | 2.90455 |
| Swiss Landfrauen | Amishland Heirloom Seeds | 0.18455 | 2.91128 |

TABLE O

Figure 15:
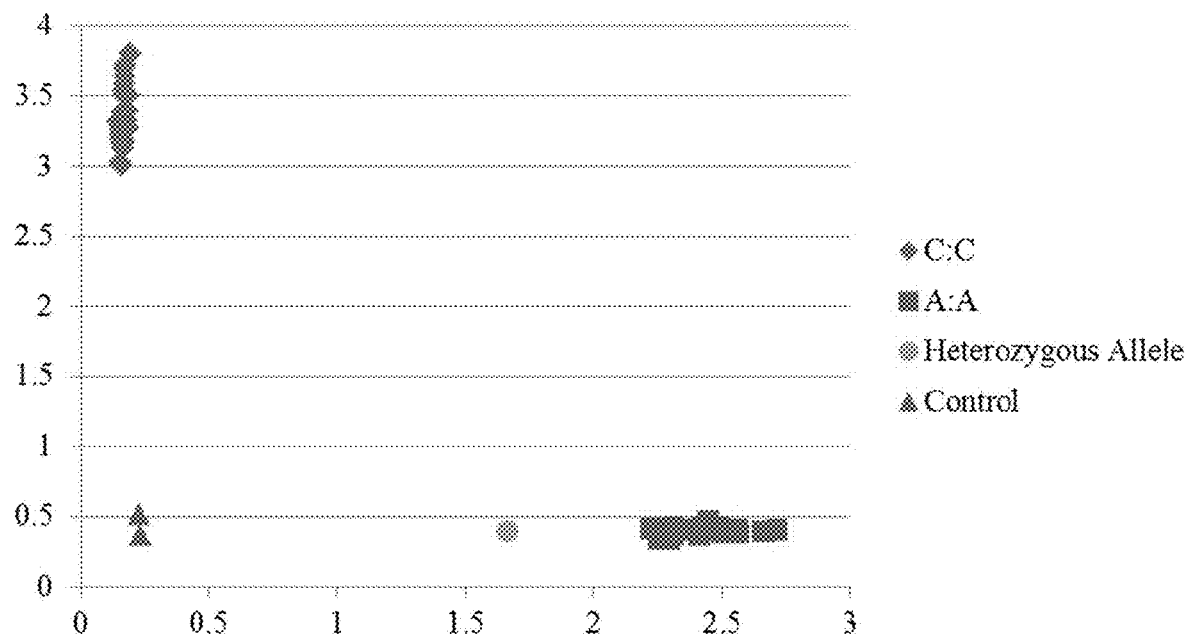
FIG. 15 illustrates a cluster (Cartesian) plot of fluorescent signals reporting each individual DNA sample obtained from a bean line (see, TABLE O) having SNP 6. The FAM fluorescence value associated with the FAM-labelled oligo sequence (FAM-labeled primer) is plotted on the X axis. The data points plotted close to the X axis represent high FAM signal and no HEX signal generated during the KASP reaction, and the related bean line samples (see, TABLE O), are homozygous for the allele reported by FAM, i.e., A. The HEX fluorescence value associated with the HEX-labelled oligo sequence (HEX-labeled primer) is plotted on the Y axis. The data points plotted close to the Y axis represent high HEX signal and no FAM signal generated during the KASP reaction, and the related bean line samples (see, TABLE O), are homozygous for the allele reported by HEX, i.e., C. A sample that is heterozygous contains both the allele reported by FAM and the allele reported by HEX and generated half as much FAM fluorescence and half as much HEX fluorescence in comparison to the samples that are homozygous for these alleles. This data point is plotted in the center of the plot, representing half FAM signal and half HEX signal. The KASP reaction without any template DNA, i.e., no template control (NTC), is included as a negative control to ensure reliability and did not generate any fluorescence, and the data point is plotted at the origin.

Validation Data for SNP 6 showing KASP Assay Results for FAM-labeled forward primer and HEX-labeled forward primer plotted in FIG. 15.

| Line | Source | X Axis | Y Axis |
| --- | --- | --- | --- |
| 91-1009 | Dickson Collection | 2.22733 | 0.41319 |
| 91-1028 | Dickson Collection | 2.67499 | 0.3956 |
| 91-1033B | Dickson Collection | 0.16452 | 3.12957 |
| 91-1145 | Dickson Collection | 2.2551 | 0.34578 |
| 91-1542 | Dickson Collection | 0.17148 | 3.51636 |
| 91-1643 | Dickson Collection | 2.30779 | 0.42273 |
| 91-1672 | Dickson Collection | 2.48833 | 0.42719 |
| 91-1728 | Dickson Collection | 2.37016 | 0.40683 |
| 91-1748 | Dickson Collection | 2.55802 | 0.40705 |

TABLE O-continued

Validation Data for SNP 6 showing KASP Assay Results for FAM-labeled forward primer and HEX-labeled forward primer plotted in FIG. 15.

| Line | Source | X Axis | Y Axis |
|---|---|---|---|
| 91-1750 | Dickson Collection | 0.17234 | 3.6416 |
| 91-1755 | Dickson Collection | 2.41103 | 0.37451 |
| 91-1759 | Dickson Collection | 0.17087 | 3.53704 |
| 91-1768 | Dickson Collection | 1.66538 | 0.39701 |
| 91-1976 | Dickson Collection | 2.44866 | 0.46717 |
| 91-2100 | Dickson Collection | 0.16174 | 3.01135 |
| 91-3346 | Dickson Collection | 0.18641 | 3.26232 |
| 91-3915 | Dickson Collection | 0.16397 | 3.19242 |
| 91-3918 | Dickson Collection | 0.16973 | 3.58031 |
| 91-3921 | Dickson Collection | 2.65639 | 0.4002 |
| Acclaim | Seminis | 0.17889 | 3.28047 |
| Aunt Ada | Turtle Tree Seed | 2.28856 | 0.37718 |
| B-1 | SerinXOregon5630 cross, F6 | 0.15997 | 3.25711 |
| B-15 | SerinXOregon5630 cross, F6 | 0.17208 | 3.50745 |
| B-28 | SerinXOregon5630 cross, F6 | 0.16292 | 3.3847 |
| B-36 | SerinXOregon5630 cross, F6 | 0.15982 | 3.15827 |
| B-37 | SerinXOregon5630 cross, F6 | 0.15344 | 3.29164 |
| B-38 | SerinXOregon5630 cross, F6 | 0.15376 | 3.02816 |
| B-41 | SerinXOregon5630 cross, F6 | 0.17071 | 3.32168 |
| B-42 | SerinXOregon5630 cross, F6 | 0.17331 | 3.71952 |
| BBL274 | Seminis | 0.15615 | 3.20055 |
| Benchmark | Syngenta | 0.15371 | 3.23138 |
| Booster | Syngenta | 0.17568 | 3.31913 |
| Calgreen | Syngenta | 0.17057 | 3.1735 |
| Castano | Syngenta | 0.1822 | 3.3974 |
| Coloma | Syngenta | 2.27744 | 0.34829 |
| Control 1 | No template controls | 0.23284 | 0.37226 |
| Control 2 | No template controls | 0.22699 | 0.51219 |
| Cosse Violette | Amishland Heirloom Seeds | 0.18971 | 3.50055 |
| Cyclone | Seminis | 0.16394 | 3.3106 |
| Flavor Sweet | Harris Moran | 0.15881 | 3.26545 |
| FM1 Pole Blue | USDA collection: Ferry-Morse | 0.17819 | 3.32263 |
| Fortex | Oregon State University | 0.19331 | 3.79546 |
| Hidatsa Shield | Seed Savers Exchange | 2.42017 | 0.42521 |
| Kentucky Wonder | Syngenta | 2.29632 | 0.34691 |
| Mercury | Syngenta | 0.14707 | 3.32372 |
| New Mex Cave | Peace Seedlings | 2.50019 | 0.38715 |
| PHA0008 | Misión Biológica de Galicia - CSIC | 2.71115 | 0.40785 |
| PHA0112 | Misión Biológica de Galicia - CSIC | 2.47373 | 0.40871 |
| PHA0192 | Misión Biológica de Galicia - CSIC | 0.17182 | 3.69406 |
| PHA0315 | Misión Biológica de Galicia - CSIC | 2.31074 | 0.3732 |
| Swiss Landfrauen | Amishland Heirloom Seeds | 2.56686 | 0.39063 |

TABLE P

Figure 16:
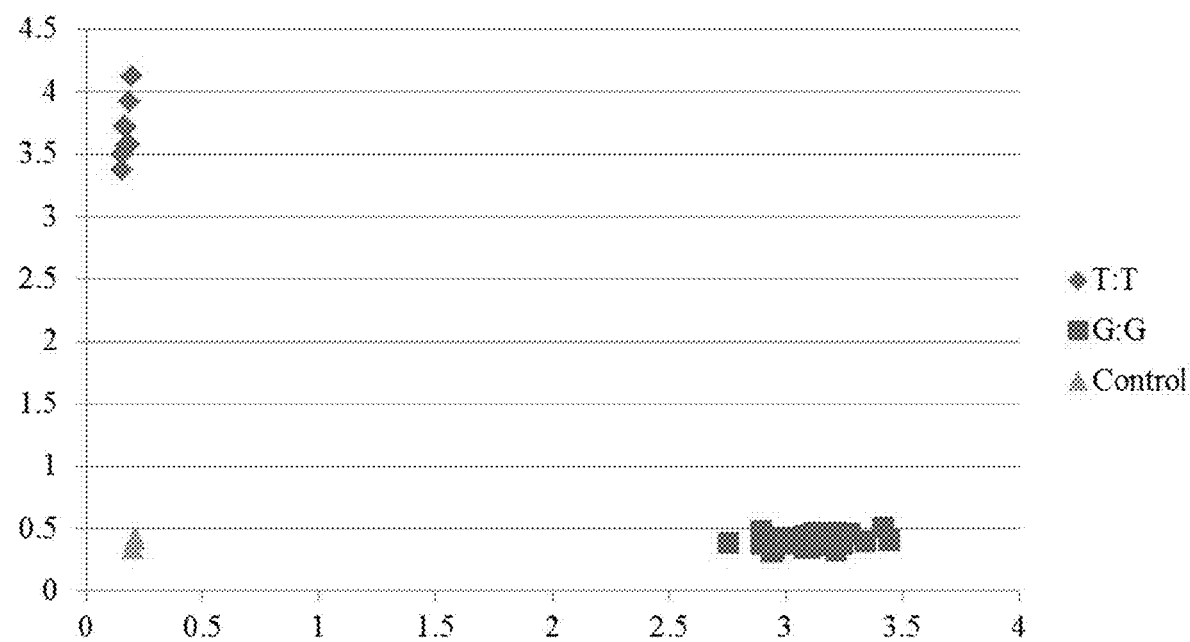
FIG. 16 illustrates a cluster (Cartesian) plot of fluorescent signals reporting each individual DNA sample obtained from a bean line (see, TABLE P) having SNP 7. The FAM fluorescence value associated with the FAM-labelled oligo sequence (FAM-labeled primer) is plotted on the X axis. The data points plotted close to the X axis represent high FAM signal and no HEX signal generated during the KASP reaction, and the related bean line samples (see, TABLE P), are homozygous for the allele reported by FAM, i.e., G. The HEX fluorescence value associated with the HEX-labelled oligo sequence (HEX-labeled primer) is plotted on the Y axis. The data points plotted close to the Y axis represent high HEX signal and no FAM signal generated during the KASP reaction, and the related bean line samples (see, TABLE P), are homozygous for the allele reported by HEX, i.e., T. The KASP reaction without any template DNA, i.e., no template control (NTC), is included as a negative control to ensure reliability and did not generate any fluorescence, and the data point is plotted at the origin.

Validation Data for SNP 7 showing KASP Assay Results for FAM-labeled forward primer and HEX-labeled forward primer plotted in FIG. 16.

| Line | Source | X Axis | Y Axis |
|---|---|---|---|
| 91-1009 | Dickson Collection | 3.34088 | 0.39763 |
| 91-1028 | Dickson Collection | 3.04704 | 0.42102 |
| 91-1033B | Dickson Collection | 3.21568 | 0.33183 |
| 91-1145 | Dickson Collection | 2.94862 | 0.34966 |
| 91-1542 | Dickson Collection | 3.24088 | 0.38352 |
| 91-1643 | Dickson Collection | 3.09495 | 0.42795 |
| 91-1672 | Dickson Collection | 2.99141 | 0.37427 |
| 91-1728 | Dickson Collection | 2.89229 | 0.47823 |
| 91-1748 | Dickson Collection | 3.444 | 0.41153 |
| 91-1750 | Dickson Collection | 3.07855 | 0.42465 |
| 91-1755 | Dickson Collection | 2.93988 | 0.3207 |
| 91-1759 | Dickson Collection | 3.06372 | 0.42732 |
| 91-1768 | Dickson Collection | 3.09663 | 0.4457 |
| 91-1976 | Dickson Collection | 3.41422 | 0.50615 |
| 91-2100 | Dickson Collection | 2.98657 | 0.43286 |
| 91-3346 | Dickson Collection | 3.10725 | 0.38013 |
| 91-3915 | Dickson Collection | 3.08977 | 0.37621 |
| 91-3918 | Dickson Collection | 3.21681 | 0.46647 |

TABLE P-continued

Validation Data for SNP 7 showing KASP Assay Results for FAM-labeled forward primer and HEX-labeled forward primer plotted in FIG. 16.

| Line | Source | X Axis | Y Axis |
|---|---|---|---|
| 91-3921 | Dickson Collection | 3.07506 | 0.42439 |
| Acclaim | Seminis | 3.10162 | 0.4319 |
| Aunt Ada | Turtle Tree Seed | 3.27296 | 0.45545 |
| B-1 | SerinXOregon5630 cross, F6 | 0.16495 | 3.72614 |
| B-15 | SerinXOregon5630 cross, F6 | 0.17446 | 3.56493 |
| B-28 | SerinXOregon5630 cross, F6 | 0.17237 | 3.70608 |
| B-36 | SerinXOregon5630 cross, F6 | 0.17433 | 3.5628 |
| B-37 | SerinXOregon5630 cross, F6 | 0.17969 | 3.56402 |
| B-38 | SerinXOregon5630 cross, F6 | 0.19557 | 4.12391 |
| B-41 | SerinXOregon5630 cross, F6 | 0.15516 | 3.50039 |
| B-42 | SerinXOregon5630 cross, F6 | 0.18824 | 3.57258 |
| BBL274 | Seminis | 2.97922 | 0.38087 |
| Benchmark | Syngenta | 2.75492 | 0.38972 |
| Booster | Syngenta | 0.18599 | 3.92434 |
| Calgreen | Syngenta | 3.15367 | 0.37116 |
| Castano | Syngenta | 3.06345 | 0.3887 |
| Coloma | Syngenta | 3.15044 | 0.37845 |
| Control 1 | No template controls | 0.20284 | 0.34437 |
| Control 2 | No template controls | 0.21363 | 0.41926 |
| Cosse Violette | Amishland Heirloom Seeds | 3.12259 | 0.46873 |
| Cyclone | Seminis | 3.11352 | 0.44231 |
| Flavor Sweet | Harris Moran | 0.15396 | 3.37487 |
| FM1 Pole Blue | USDA collection: Ferry-Morse | 3.16923 | 0.39541 |
| Fortex | Oregon State University | 3.04324 | 0.38775 |
| Hidatsa Shield | Seed Savers Exchange | 3.10036 | 0.34765 |
| Kentucky Wonder | Syngenta | 3.1198 | 0.37744 |
| Mercury | Syngenta | 3.09895 | 0.379 |
| New Mex Cave | Peace Seedlings | 3.08121 | 0.43604 |
| PHA0008 | Misión Biológica de Galicia - CSIC | 3.09032 | 0.42517 |
| PHA0112 | Misión Biológica de Galicia - CSIC | 2.89351 | 0.37754 |
| PHA0192 | Misión Biológica de Galicia - CSIC | 3.12987 | 0.37616 |
| PHA0315 | Misión Biológica de Galicia - CSIC. | 3.15225 | 0.36849 |
| Swiss Landfrauen | Amishland Heirloom Seeds | 3.07912 | 0.35056 |

TABLE Q

Figure 17:
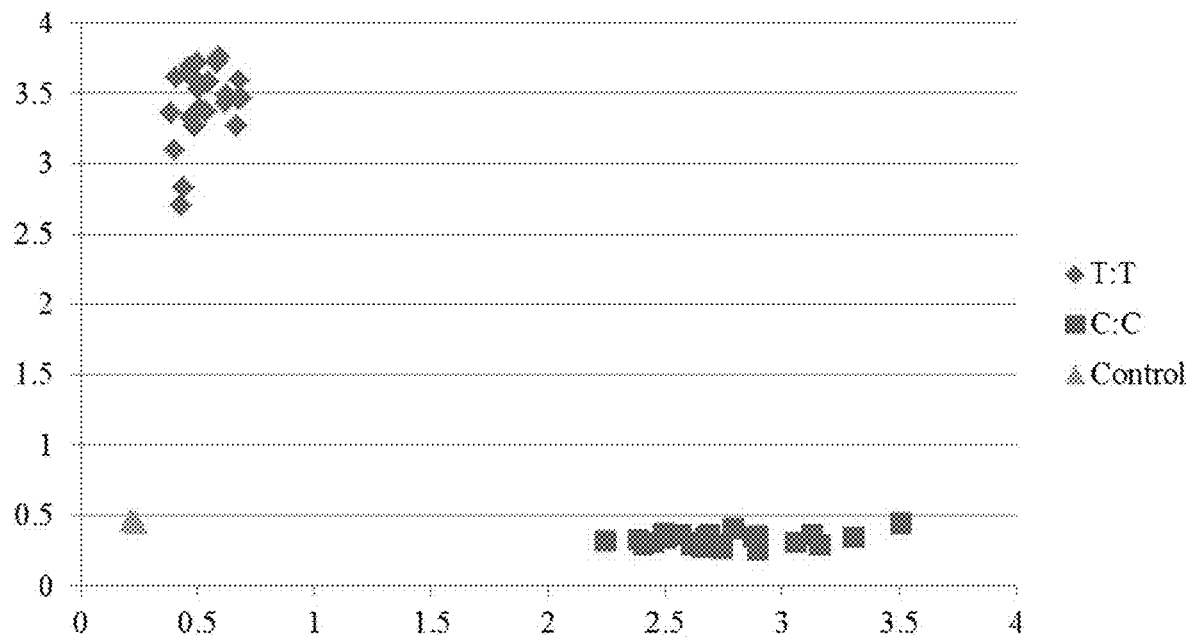
FIG. 17 illustrates a cluster (Cartesian) plot of fluorescent signals reporting each individual DNA sample obtained from a bean line (see, TABLE Q) having SNP 8. The FAM fluorescence value associated with the FAM-labelled oligo sequence (FAM-labeled primer) is plotted on the X axis. The data points plotted close to the X axis represent high FAM signal and no HEX signal generated during the KASP reaction, and the related bean line samples (see, TABLE Q), are homozygous for the allele reported by FAM, i.e., C. The HEX fluorescence value associated with the HEX-labelled oligo sequence (HEX-labeled primer) is plotted on the Y axis. The data points plotted close to the Y axis represent high HEX signal and no FAM signal generated during the KASP reaction, and the related bean line samples (see, TABLE Q), are homozygous for the allele reported by HEX, i.e., T. The KASP reaction without any template DNA, i.e., no template control (NTC), is included as a negative control to ensure reliability and did not generate any fluorescence, and the data point is plotted at the origin.

Validation Data for SNP 8 showing KASP Assay Results for FAM-labeled forward primer and HEX-labeled forward primer plotted in FIG. 17.

| Line | Source | X Axis | Y Axis |
|---|---|---|---|
| 91-1009 | Dickson Collection | 2.65545 | 0.27227 |
| 91-1028 | Dickson Collection | 2.71869 | 0.29532 |
| 91-1033B | Dickson Collection | 2.50133 | 0.3561 |
| 91-1145 | Dickson Collection | 2.49229 | 0.37678 |
| 91-1542 | Dickson Collection | 2.68824 | 0.36102 |
| 91-1643 | Dickson Collection | 2.45136 | 0.30695 |
| 91-1672 | Dickson Collection | 2.67258 | 0.34626 |
| 91-1728 | Dickson Collection | 2.89519 | 0.35105 |
| 91-1748 | Dickson Collection | 3.50596 | 0.44755 |
| 91-1750 | Dickson Collection | 3.15899 | 0.2885 |
| 91-1755 | Dickson Collection | 2.64738 | 0.29182 |
| 91-1759 | Dickson Collection | 2.38636 | 0.32876 |
| 91-1768 | Dickson Collection | 2.56267 | 0.36553 |
| 91-1976 | Dickson Collection | 2.61124 | 0.29516 |
| 91-2100 | Dickson Collection | 2.50524 | 0.33432 |
| 91-3346 | Dickson Collection | 2.87654 | 0.34764 |
| 91-3915 | Dickson Collection | 2.89525 | 0.2586 |
| 91-3918 | Dickson Collection | 3.30865 | 0.34921 |
| 91-3921 | Dickson Collection | 3.0553 | 0.3126 |
| Acclaim | Seminis | 0.38807 | 3.36219 |
| Aunt Ada | Turtle Tree Seed | 0.46122 | 3.64603 |
| B-1 | SerinXOregon5630 cross, F6 | 0.59132 | 3.75289 |
| B-15 | SerinXOregon5630 cross, F6 | 0.5827 | 3.72283 |
| B-28 | SerinXOregon5630 cross, F6 | 0.40549 | 3.09901 |
| B-36 | SerinXOregon5630 cross, F6 | 0.42897 | 2.70381 |
| B-37 | SerinXOregon5630 cross, F6 | 0.67498 | 3.46223 |
| B-38 | SerinXOregon5630 cross, F6 | 0.62687 | 3.48664 |

TABLE Q-continued

Validation Data for SNP 8 showing KASP Assay Results for FAM-labeled forward primer and HEX-labeled forward primer plotted in FIG. 17.

| Line | Source | X Axis | Y Axis |
| --- | --- | --- | --- |
| B-41 | SerinXOregon5630 cross, F6 | 0.48772 | 3.27123 |
| B-42 | SerinXOregon5630 cross, F6 | 0.67802 | 3.59005 |
| BBL274 | Seminis | 0.47324 | 3.32763 |
| Benchmark | Syngenta | 0.50856 | 3.532 |
| Booster | Syngenta | 0.69226 | 3.46483 |
| Calgreen | Syngenta | 0.51235 | 3.39406 |
| Castano | Syngenta | 0.47656 | 3.61731 |
| Coloma | Syngenta | 0.50291 | 3.71843 |
| Control 1 | No template controls | 0.21905 | 0.46523 |
| Control 2 | No template controls | 0.24224 | 0.44601 |
| Cosse Violette | Amishland Heirloom Seeds | 2.24747 | 0.32069 |
| Cyclone | Seminis | 0.40893 | 3.61301 |
| Flavor Sweet | Harris Moran | 0.43874 | 2.83083 |
| FM1 Pole Blue | USDA collection: Ferry-Morse | 2.74284 | 0.26764 |
| Fortex | Oregon State University | 3.12538 | 0.36637 |
| Hidatsa Shield | Seed Savers Exchange | 0.48456 | 3.3537 |
| Kentucky Wonder | Syngenta | 2.64661 | 0.30572 |
| Mercury | Syngenta | 0.46854 | 3.68858 |
| New Mex Cave | Peace Seedlings | 2.40839 | 0.28737 |
| PHA0008 | Misión Biológica de Galicia - CSIC | 0.53725 | 3.37202 |
| PHA0112 | Misión Biológica de Galicia - CSIC | 0.61781 | 3.43037 |
| PHA0192 | Misión Biológica de Galicia - CSIC | 0.67108 | 3.26721 |
| PHA0315 | Misión Biológica de Galicia - CSIC | 2.79359 | 0.40714 |
| Swiss Landfrauen | Amishland Heirloom Seeds | 0.54869 | 3.58084 |

TABLE R

Figure 18:
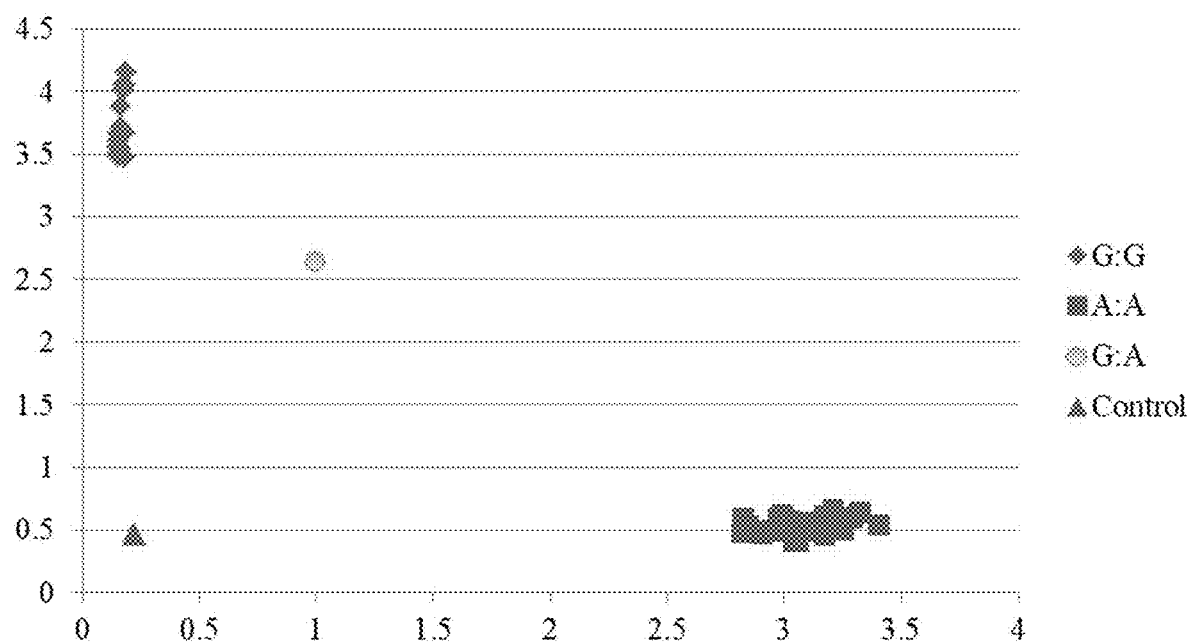
FIG. 18 illustrates a cluster (Cartesian) plot of fluorescent signals reporting each individual DNA sample obtained from a bean line (see, TABLE R) having SNP 9. The FAM fluorescence value associated with the FAM-labelled oligo sequence (FAM-labeled primer) is plotted on the X axis. The data points plotted close to the X axis represent high FAM signal and no HEX signal generated during the KASP reaction, and the related bean line samples (see, TABLE R), are homozygous for the allele reported by FAM, i.e., A. The HEX fluorescence value associated with the HEX-labelled oligo sequence (HEX-labeled primer) is plotted on the Y axis. The data points plotted close to the Y axis represent high HEX signal and no FAM signal generated during the KASP reaction, and the related bean line samples (see, TABLE R), are homozygous for the allele reported by HEX, i.e., G. A sample that is heterozygous contains both the allele reported by FAM and the allele reported by HEX and generated half as much FAM fluorescence and half as much HEX fluorescence in comparison to the samples that are homozygous for these alleles. This data point is plotted in the center of the plot, representing half FAM signal and half HEX signal. The KASP reaction without any template DNA, i.e., no template control (NTC), is included as a negative control to ensure reliability and did not generate any fluorescence, and the data point is plotted at the origin.

Validation Data for SNP 9 showing KASP Assay Results for FAM-labeled forward primer and HEX-labeled forward primer plotted in FIG. 18.

| Line | Source | X Axis | Y Axis |
| --- | --- | --- | --- |
| 91-1009 | Dickson Collection | 0.15673 | 3.55871 |
| 91-1028 | Dickson Collection | 2.91944 | 0.49148 |
| 91-1033B | Dickson Collection | 0.15389 | 3.60819 |
| 91-1145 | Dickson Collection | 2.96718 | 0.49533 |
| 91-1542 | Dickson Collection | 0.16035 | 3.67093 |
| 91-1643 | Dickson Collection | 0.16605 | 3.88226 |
| 91-1672 | Dickson Collection | 0.16479 | 3.50322 |
| 91-1728 | Dickson Collection | 0.15252 | 3.48394 |
| 91-1748 | Dickson Collection | 0.16009 | 3.65412 |
| 91-1750 | Dickson Collection | 0.16557 | 3.71586 |
| 91-1755 | Dickson Collection | 0.17759 | 4.00857 |
| 91-1759 | Dickson Collection | 0.18017 | 4.04768 |
| 91-1768 | Dickson Collection | 0.17857 | 3.47398 |
| 91-1976 | Dickson Collection | 0.1674 | 3.64638 |
| 91-2100 | Dickson Collection | 0.15241 | 3.49516 |
| 91-3346 | Dickson Collection | 3.29075 | 0.60278 |
| 91-3915 | Dickson Collection | 2.90512 | 0.46863 |
| 91-3918 | Dickson Collection | 3.32113 | 0.63873 |
| 91-3921 | Dickson Collection | 3.00748 | 0.48654 |
| Acclaim | Seminis | 3.07099 | 0.50743 |
| Aunt Ada | Turtle Tree Seed | 3.17147 | 0.60971 |
| B-1 | SerinXOregon5630 cross, F6 | 3.10419 | 0.5628 |
| B-15 | SerinXOregon5630 cross, F6 | 0.99334 | 2.6473 |
| B-28 | SerinXOregon5630 cross, F6 | 0.16646 | 3.55019 |
| B-36 | SerinXOregon5630 cross, F6 | 2.97352 | 0.59096 |
| B-37 | SerinXOregon5630 cross, F6 | 0.15683 | 3.66409 |
| B-38 | SerinXOregon5630 cross, F6 | 3.08191 | 0.50315 |
| B-41 | SerinXOregon5630 cross, F6 | 3.19122 | 0.55479 |
| B-42 | SerinXOregon5630 cross, F6 | 0.18448 | 4.15766 |
| BBL274 | Seminis | 2.84364 | 0.53455 |
| Benchmark | Syngenta | 3.05734 | 0.54038 |
| Booster | Syngenta | 3.25422 | 0.5001 |
| Calgreen | Syngenta | 3.17186 | 0.45585 |
| Castano | Syngenta | 3.40431 | 0.5398 |
| Coloma | Syngenta | 3.0209 | 0.54896 |
| Control 1 | No template controls | 0.22663 | 0.46316 |

TABLE R-continued

Validation Data for SNP 9 showing KASP Assay Results for FAM-labeled forward primer and HEX-labeled forward primer plotted in FIG. 18.

| Line | Source | X Axis | Y Axis |
| --- | --- | --- | --- |
| Control 2 | No template controls | 0.22131 | 0.46411 |
| Cosse Violette | Amishland Heirloom Seeds | 3.20714 | 0.52 |
| Cyclone | Seminis | 3.01691 | 0.57453 |
| Flavor Sweet | Harris Moran | 3.05847 | 0.41037 |
| FM1 Pole Blue | USDA collection: Ferry-Morse | 2.99279 | 0.61766 |
| Fortex | Oregon State University | 0.17949 | 3.66895 |
| Hidatsa Shield | Seed Savers Exchange | 3.24756 | 0.58641 |
| Kentucky Wonder | Syngenta | 3.04001 | 0.41252 |
| Mercury | Syngenta | 2.99227 | 0.58212 |
| New Mex Cave | Peace Seedlings | 2.8189 | 0.48048 |
| PHA0008 | Misión Biológica de Galicia - CSIC | 3.20725 | 0.66017 |
| PHA0112 | Misión Biológica de Galicia - CSIC | 2.82483 | 0.58944 |
| PHA0192 | Misión Biológica de Galicia - CSIC | 3.20459 | 0.60099 |
| PHA0315 | Misión Biológica de Galicia - CSIC | 3.13025 | 0.49312 |
| Swiss Landfrauen | Amishland Heirloom Seeds | 2.94708 | 0.5021 |

TABLE S

Figure 19:
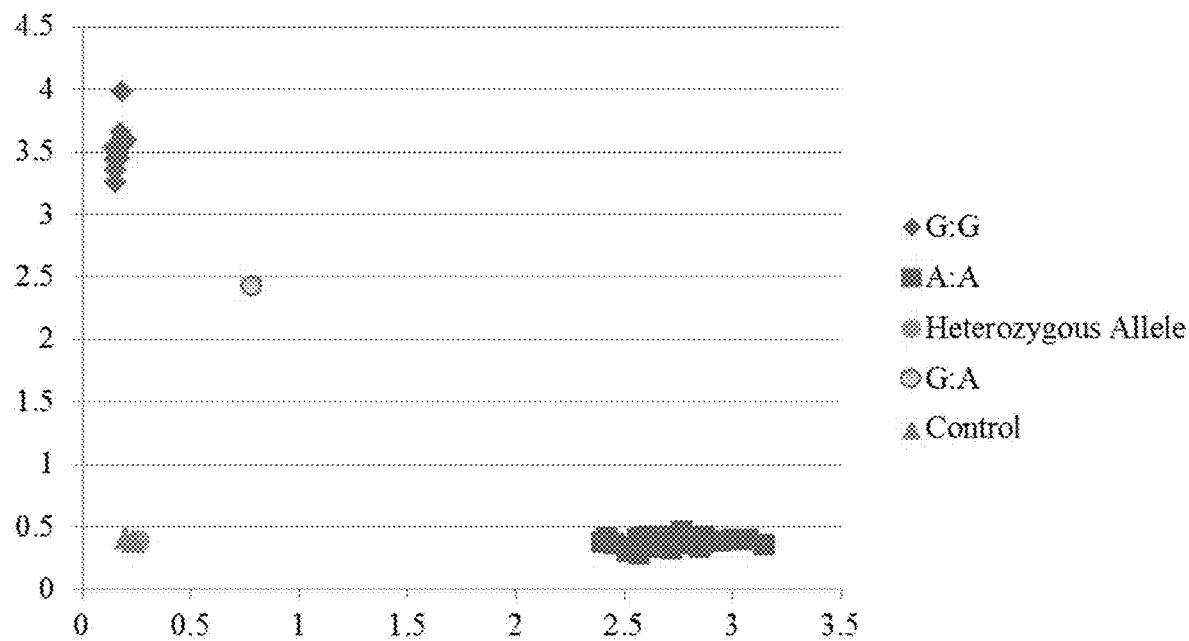
FIG. 19 illustrates a cluster (Cartesian) plot of fluorescent signals reporting each individual DNA sample obtained from a bean line (see, TABLE S) having SNP 10. The FAM fluorescence value associated with the FAM-labelled oligo sequence (FAM-labeled primer) is plotted on the X axis. The data points plotted close to the X axis represent high FAM signal and no HEX signal generated during the KASP reaction, and the related bean line samples (see, TABLE S), are homozygous for the allele reported by FAM, i.e., A. The HEX fluorescence value associated with the HEX-labelled oligo sequence (HEX-labeled primer) is plotted on the Y axis. The data points plotted close to the Y axis represent high HEX signal and no FAM signal generated during the KASP reaction, and the related bean line samples (see, TABLE S), are homozygous for the allele reported by HEX, i.e., G. A sample that is heterozygous contains both the allele reported by FAM and the allele reported by HEX and generated half as much FAM fluorescence and half as much HEX fluorescence in comparison to the samples that are homozygous for these alleles. This data point is plotted in the center of the plot, representing half FAM signal and half HEX signal. The KASP reaction without any template DNA, i.e., no template control (NTC), is included as a negative control to ensure reliability and did not generate any fluorescence, and the data point is plotted at the origin.

Validation Data for SNP 10 showing KASP Assay Results for FAM-labeled forward primer and HEX-labeled forward primer plotted in FIG. 19.

| Line | Source | X Axis | Y Axis |
| --- | --- | --- | --- |
| 91-1009 | Dickson Collection | 2.60209 | 0.35423 |
| 91-1028 | Dickson Collection | 2.76008 | 0.39459 |
| 91-1033B | Dickson Collection | 0.77834 | 2.42874 |
| 91-1145 | Dickson Collection | 2.65178 | 0.36831 |
| 91-1542 | Dickson Collection | 3.06598 | 0.39764 |
| 91-1643 | Dickson Collection | 2.59983 | 0.42802 |
| 91-1672 | Dickson Collection | 2.73162 | 0.39909 |
| 91-1728 | Dickson Collection | 2.5305 | 0.34253 |
| 91-1748 | Dickson Collection | 3.00609 | 0.39735 |
| 91-1750 | Dickson Collection | 2.94737 | 0.38742 |
| 91-1755 | Dickson Collection | 2.69435 | 0.42533 |
| 91-1759 | Dickson Collection | 2.45165 | 0.36684 |
| 91-1768 | Dickson Collection | 2.69924 | 0.42671 |
| 91-1976 | Dickson Collection | 2.56846 | 0.29004 |
| 91-2100 | Dickson Collection | 2.51388 | 0.31215 |
| 91-3346 | Dickson Collection | 2.75915 | 0.37223 |
| 91-3915 | Dickson Collection | 2.76661 | 0.47324 |
| 91-3918 | Dickson Collection | 3.14508 | 0.36307 |
| 91-3921 | Dickson Collection | 2.71613 | 0.33267 |
| Acclaim | Seminis | 0.15755 | 3.42331 |
| Aunt Ada | Turtle Tree Seed | 0.16717 | 3.50515 |
| B-1 | SerinXOregon5630 cross, F6 | 2.84922 | 0.33582 |
| B-15 | SerinXOregon5630 cross, F6 | 2.87049 | 0.38264 |
| B-28 | SerinXOregon5630 cross, F6 | 2.86166 | 0.43279 |
| B-36 | SerinXOregon5630 cross, F6 | 2.81808 | 0.37013 |
| B-37 | SerinXOregon5630 cross, F6 | 2.80509 | 0.39138 |
| B-38 | SerinXOregon5630 cross, F6 | 2.56026 | 0.34672 |
| B-41 | SerinXOregon5630 cross, F6 | 2.39797 | 0.37697 |
| B-42 | SerinXOregon5630 cross, F6 | 2.83194 | 0.40878 |
| BBL274 | Seminis | 0.18266 | 3.56678 |
| Benchmark | Syngenta | 2.42107 | 0.4081 |
| Booster | Syngenta | 2.56313 | 0.39348 |
| Calgreen | Syngenta | 0.15533 | 3.44557 |
| Castano | Syngenta | 0.17039 | 3.44449 |
| Coloma | Syngenta | 2.60566 | 0.35811 |
| Control 1 | No template controls | 0.23864 | 0.37768 |
| Control 2 | No template controls | 0.19975 | 0.40586 |
| Cosse Violette | Amishland Heirloom Seeds | 2.66453 | 0.33814 |
| Cyclone | Seminis | 0.1529 | 3.25501 |
| Flavor Sweet | Harris Moran | 0.1659 | 3.48368 |
| FM1 Pole Blue | USDA collection: Ferry-Morse | 0.25673 | 3.39231 |
| Fortex | Oregon State University | 2.72999 | 0.39932 |
| Hidatsa Shield | Seed Savers Exchange | 0.15035 | 3.54095 |
| Kentucky Wonder | Syngenta | 2.75448 | 0.3829 |

TABLE S-continued

Validation Data for SNP 10 showing KASP Assay Results for FAM-labeled forward primer and HEX-labeled forward primer plotted in FIG. 19.

| Line | Source | X Axis | Y Axis |
| --- | --- | --- | --- |
| Mercury | Syngenta | 0.1822 | 3.98059 |
| New Mex Cave | Peace Seedlings | 2.74046 | 0.42594 |
| PHA0008 | Misión Biológica de Galicia - CSIC | 0.17755 | 3.65782 |
| PHA0112 | Misión Biológica de Galicia - CSIC | 0.15651 | 3.35327 |
| PHA0192 | Misión Biológica de Galicia - CSIC | 0.20235 | 3.5959 |
| PHA0315 | Misión Biológica de Galicia - CSIC | 2.57635 | 0.42038 |
| Swiss Landfrauen | Amishland Heirloom Seeds | 0.18666 | 3.55535 |

TABLE T

Figure 20:
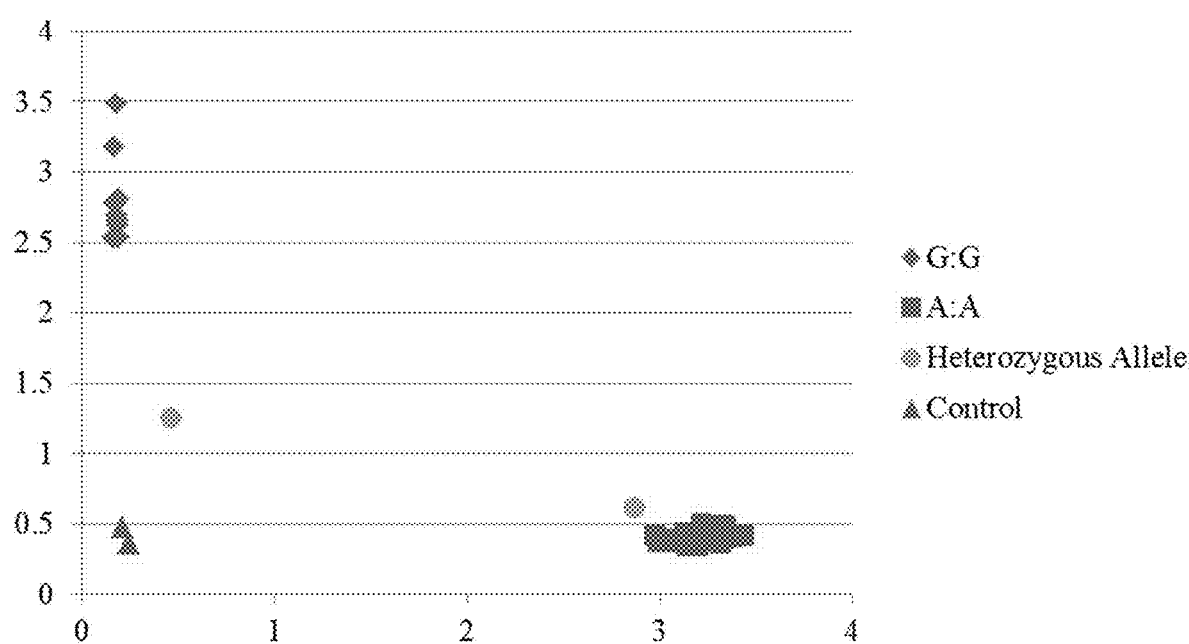
FIG. 20 illustrates a cluster (Cartesian) plot of fluorescent signals reporting each individual DNA sample obtained from a bean line (see, TABLE T) having SNP 11. The FAM fluorescence value associated with the FAM-labelled oligo sequence (FAM-labeled primer) is plotted on the X axis. The data points plotted close to the X axis represent high FAM signal and no HEX signal generated during the KASP reaction, and the related bean line samples (see, TABLE T), are homozygous for the allele reported by FAM, i.e., A. The HEX fluorescence value associated with the HEX-labelled oligo sequence (HEX-labeled primer) is plotted on the Y axis. The data points plotted close to the Y axis represent high HEX signal and no FAM signal generated during the KASP reaction, and the related bean line samples (see, TABLE T), are homozygous for the allele reported by HEX, i.e., G. A sample that is heterozygous contains both the allele reported by FAM and the allele reported by HEX and generated half as much FAM fluorescence and half as much HEX fluorescence in comparison to the samples that are homozygous for these alleles. This data point is plotted in the center of the plot, representing half FAM signal and half HEX signal. The KASP reaction without any template DNA, i.e., no template control (NTC), is included as a negative control to ensure reliability and did not generate any fluorescence, and the data point is plotted at the origin.

Validation Data for SNP 11 showing KASP Assay Results for FAM-labeled forward primer and HEX-labeled forward primer plotted in FIG. 20.

| Line | Source | X Axis | Y Axis |
| --- | --- | --- | --- |
| 91-1009 | Dickson Collection | 3.03621 | 0.36898 |
| 91-1028 | Dickson Collection | 3.10616 | 0.39185 |
| 91-1033B | Dickson Collection | 3.12924 | 0.38382 |
| 91-1145 | Dickson Collection | 2.99038 | 0.37011 |
| 91-1542 | Dickson Collection | 3.27228 | 0.4238 |
| 91-1643 | Dickson Collection | 3.20785 | 0.40234 |
| 91-1672 | Dickson Collection | 3.33506 | 0.4724 |
| 91-1728 | Dickson Collection | 3.26944 | 0.43703 |
| 91-1748 | Dickson Collection | 3.28615 | 0.38083 |
| 91-1750 | Dickson Collection | 3.12991 | 0.42755 |
| 91-1755 | Dickson Collection | 3.29326 | 0.40917 |
| 91-1759 | Dickson Collection | 3.13191 | 0.43782 |
| 91-1768 | Dickson Collection | 3.14061 | 0.39885 |
| 91-1976 | Dickson Collection | 3.36627 | 0.40684 |
| 91-2100 | Dickson Collection | 0.46519 | 1.2562 |
| 91-3346 | Dickson Collection | 0.17252 | 2.77941 |
| 91-3915 | Dickson Collection | 0.16962 | 2.53472 |
| 91-3918 | Dickson Collection | 0.16774 | 3.17628 |
| 91-3921 | Dickson Collection | 0.1748 | 2.77345 |
| Acclaim | Seminis | 3.20928 | 0.38082 |
| Aunt Ada | Turtle Tree Seed | 3.19605 | 0.34772 |
| B-1 | SerinXOregon5630 cross, F6 | 3.3395 | 0.47932 |
| B-15 | SerinXOregon5630 cross, F6 | 3.43602 | 0.41629 |
| B-28 | SerinXOregon5630 cross, F6 | 0.17914 | 2.79523 |
| B-36 | SerinXOregon5630 cross, F6 | 0.19179 | 2.81258 |
| B-37 | SerinXOregon5630 cross, F6 | 3.18714 | 0.42912 |
| B-38 | SerinXOregon5630 cross, F6 | 3.14268 | 0.34328 |
| B-41 | SerinXOregon5630 cross, F6 | 2.86759 | 0.61457 |
| B-42 | SerinXOregon5630 cross, F6 | 0.17799 | 3.48269 |
| BBL274 | Seminis | 3.38187 | 0.40966 |
| Benchmark | Syngenta | 0.19146 | 2.53218 |
| Booster | Syngenta | 3.31775 | 0.36801 |
| Calgreen | Syngenta | 3.22992 | 0.47837 |
| Castano | Syngenta | 3.25032 | 0.39349 |
| Coloma | Syngenta | 3.076 | 0.39071 |
| Control 1 | No template controls | 0.24698 | 0.35309 |
| Control 2 | No template controls | 0.2121 | 0.46867 |
| Cosse Violette | Amishland Heirloom Seeds | 3.19218 | 0.41714 |
| Cyclone | Seminis | 3.31633 | 0.41874 |
| Flavor Sweet | Harris Moran | 2.97518 | 0.41565 |
| FM1 Pole Blue | USDA collection: Ferry-Morse | 0.18557 | 2.66057 |
| Fortex | Oregon State University | 3.13048 | 0.40355 |
| Hidatsa Shield | Seed Savers Exchange | 3.32596 | 0.44501 |
| Kentucky Wonder | Syngenta | 0.18574 | 2.62277 |
| Mercury | Syngenta | 3.36895 | 0.4065 |
| New Mex Cave | Peace Seedlings | 3.28272 | 0.42779 |
| PHA0008 | Misión Biológica de Galicia - CSIC | 3.21922 | 0.5015 |
| PHA0112 | Misión Biológica de Galicia - CSIC | 3.17257 | 0.38654 |
| PHA0192 | Misión Biológica de Galicia - CSIC | 3.32578 | 0.3997 |
| PHA0315 | Misión Biológica de Galicia - CSIC | 0.17805 | 2.69582 |
| Swiss Landfrauen | Amishland Heirloom Seeds, | 3.32756 | 0.49083 |

TABLE U

Figure 21:
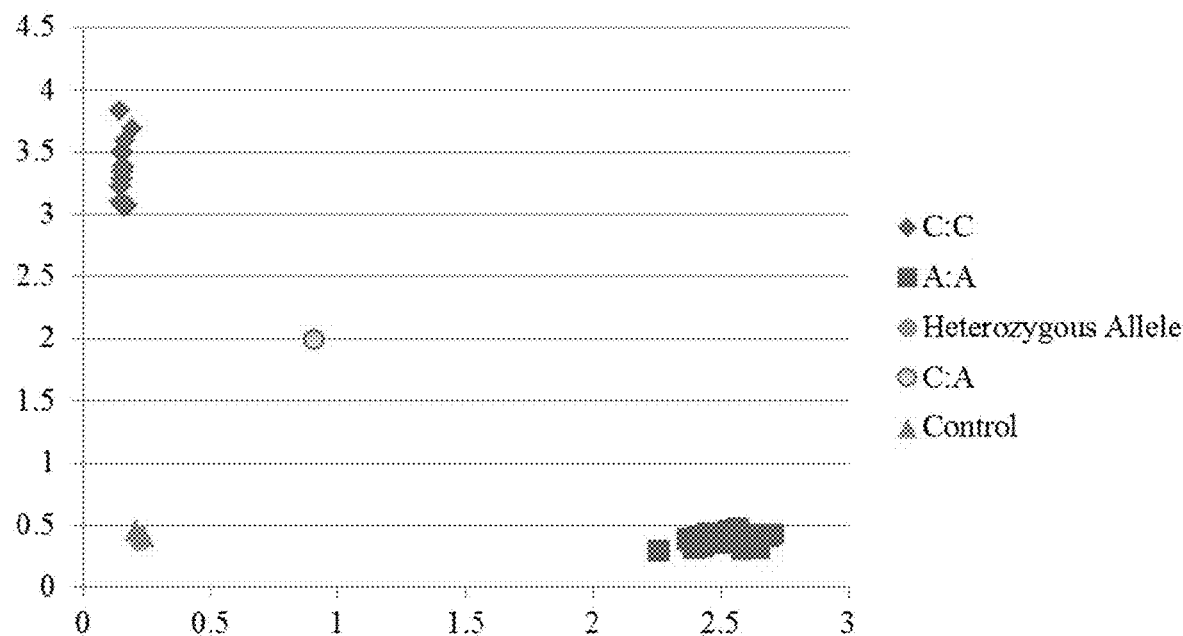
FIG. 21 illustrates a cluster (Cartesian) plot of fluorescent signals reporting each individual DNA sample obtained from a bean line (see, TABLE U) having SNP 12. The FAM fluorescence value associated with the FAM-labelled oligo sequence (FAM-labeled primer) is plotted on the X axis. The data points plotted close to the X axis represent high FAM signal and no HEX signal generated during the KASP reaction, and the related bean line samples (see, TABLE U), are homozygous for the allele reported by FAM, i.e., A. The HEX fluorescence value associated with the HEX-labelled oligo sequence (HEX-labeled primer) is plotted on the Y axis. The data points plotted close to the Y axis represent high HEX signal and no FAM signal generated during the KASP reaction, and the related bean line samples (see, TABLE U), are homozygous for the allele reported by HEX, i.e., C. A sample that is heterozygous contains both the allele reported by FAM and the allele reported by HEX and generated half as much FAM fluorescence and half as much HEX fluorescence in comparison to the samples that are homozygous for these alleles. This data point is plotted in the center of the plot, representing half FAM signal and half HEX signal. The KASP reaction without any template DNA, i.e., no template control (NTC), is included as a negative control to ensure reliability and did not generate any fluorescence, and the data point is plotted at the origin.

Validation Data for SNP 12 showing KASP Assay Results for FAM-labeled forward primer and HEX-labeled forward primer plotted in FIG. 21.

| Line | Source | X Axis | Y Axis |
| --- | --- | --- | --- |
| 91-1009 | Dickson Collection | 0.16198 | 3.06916 |
| 91-1028 | Dickson Collection | 0.15524 | 3.3488 |
| 91-1033B | Dickson Collection | 2.463 | 0.35942 |
| 91-1145 | Dickson Collection | 2.43235 | 0.33108 |
| 91-1542 | Dickson Collection | 2.58492 | 0.42343 |
| 91-1643 | Dickson Collection | 0.19239 | 3.68522 |
| 91-1672 | Dickson Collection | 2.60558 | 0.36366 |
| 91-1728 | Dickson Collection | 0.16448 | 3.58839 |
| 91-1748 | Dickson Collection | 2.59786 | 0.35527 |
| 91-1750 | Dickson Collection | 2.60812 | 0.34419 |
| 91-1755 | Dickson Collection | 2.25441 | 0.29954 |
| 91-1759 | Dickson Collection | 2.48683 | 0.3697 |
| 91-1768 | Dickson Collection | 2.40768 | 0.35921 |
| 91-1976 | Dickson Collection | 2.56628 | 0.47501 |
| 91-2100 | Dickson Collection | 2.40634 | 0.40903 |
| 91-3346 | Dickson Collection | 2.68503 | 0.41072 |
| 91-3915 | Dickson Collection | 2.58062 | 0.31006 |
| 91-3918 | Dickson Collection | 2.59024 | 0.43236 |
| 91-3921 | Dickson Collection | 2.52766 | 0.4481 |
| Acclaim | Seminis | 2.47505 | 0.43409 |
| Aunt Ada | Turtle Tree Seed | 0.1605 | 3.38161 |
| B-1 | SerinXOregon5630 cross, F6 | 2.63674 | 0.36506 |
| B-15 | SerinXOregon5630 cross, F6 | 2.53499 | 0.3593 |
| B-28 | SerinXOregon5630 cross, F6 | 0.22614 | 0.37617 |
| B-36 | SerinXOregon5630 cross, F6 | 0.90288 | 1.99513 |
| B-37 | SerinXOregon5630 cross, F6 | 2.44537 | 0.44062 |
| B-38 | SerinXOregon5630 cross, F6 | 2.63715 | 0.42584 |
| B-41 | SerinXOregon5630 cross, F6 | 2.41056 | 0.37658 |
| B-42 | SerinXOregon5630 cross, F6 | 0.14487 | 3.833 |
| BBL274 | Seminis | 2.59254 | 0.35037 |
| Benchmark | Syngenta | 2.40477 | 0.35509 |
| Booster | Syngenta | 2.38134 | 0.36859 |
| Calgreen | Syngenta | 0.15007 | 3.21978 |
| Castano | Syngenta | 2.36557 | 0.38395 |
| Coloma | Syngenta | 2.4541 | 0.39351 |
| Control 1 | No template controls | 0.20731 | 0.4592 |
| Control 2 | No template controls | 0.23645 | 0.41051 |
| Cosse Violette | Amishland Heirloom Seeds | 2.48444 | 0.36979 |
| Cyclone | Seminis | 2.52658 | 0.46091 |
| Flavor Sweet | Harris Moran | 2.39128 | 0.32193 |
| FM1 Pole Blue | USDA collection: Ferry-Morse | 2.43201 | 0.41716 |
| Fortex | Oregon State University | 2.65066 | 0.3219 |
| Hidatsa Shield | Seed Savers Exchange | 0.15361 | 3.28314 |
| Kentucky Wonder | Syngenta | 2.58751 | 0.38544 |
| Mercury | Syngenta | 2.5774 | 0.34331 |
| New Mex Cave | Peace Seedlings | 2.70531 | 0.42929 |
| PHA0008 | Misión Biológica de Galicia - CSIC | 0.15721 | 3.49821 |
| PHA0112 | Misión Biológica de Galicia - CSIC | 0.15176 | 3.10384 |
| PHA0192 | Misión Biológica de Galicia - CSIC | 0.17246 | 3.07206 |
| PHA0315 | Misión Biológica de Galicia - CSIC | 2.55066 | 0.42747 |
| Swiss Landfrauen | Amishland Heirloom Seeds | 2.51479 | 0.3818 |

TABLE V

Figure 22:
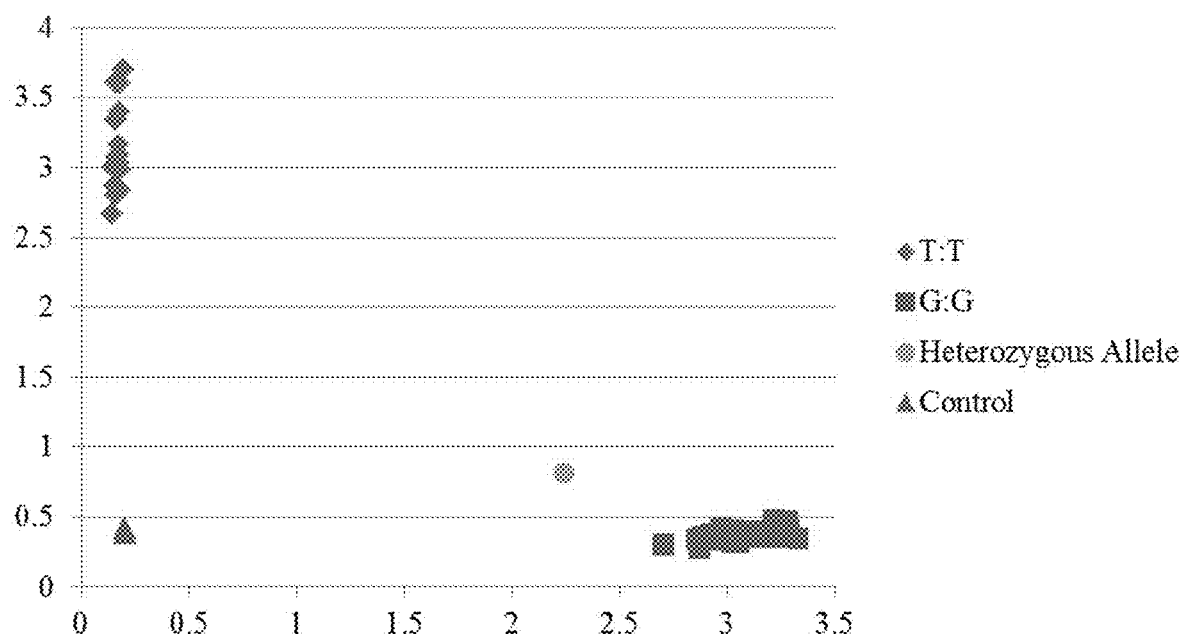
FIG. 22 illustrates a cluster (Cartesian) plot of fluorescent signals reporting each individual DNA sample obtained from a bean line (see, TABLE V) having SNP 13. The FAM fluorescence value associated with the FAM-labelled oligo sequence (FAM-labeled primer) is plotted on the X axis. The data points plotted close to the X axis represent high FAM signal and no HEX signal generated during the KASP reaction, and the related bean line samples (see, TABLE V), are homozygous for the allele reported by FAM, i.e., G. The HEX fluorescence value associated with the HEX-labelled oligo sequence (HEX-labeled primer) is plotted on the Y axis. The data points plotted close to the Y axis represent high HEX signal and no FAM signal generated during the KASP reaction, and the related bean line samples (see, TABLE V), are homozygous for the allele reported by HEX, i.e., T. A sample that is heterozygous contains both the allele reported by FAM and the allele reported by HEX and generated half as much FAM fluorescence and half as much HEX fluorescence in comparison to the samples that are homozygous for these alleles. This data point is plotted in the center of the plot, representing half FAM signal and half HEX signal. The KASP reaction without any template DNA, i.e., no template control (NTC), is included as a negative control to ensure reliability and did not generate any fluorescence, and the data point is plotted at the origin.

Validation Data for SNP 13 showing KASP Assay Results for FAM-labeled forward primer and HEX-labeled forward primer plotted in FIG. 22.

| Line | Source | X Axis | Y Axis |
| --- | --- | --- | --- |
| 91-1009 | Dickson Collection | 3.10841 | 0.38093 |
| 91-1028 | Dickson Collection | 2.24016 | 0.81145 |
| 91-1033B | Dickson Collection | 2.92268 | 0.34008 |
| 91-1145 | Dickson Collection | 2.8799 | 0.35795 |
| 91-1542 | Dickson Collection | 0.1697 | 3.16456 |
| 91-1643 | Dickson Collection | 0.15745 | 2.80353 |
| 91-1672 | Dickson Collection | 3.26693 | 0.39388 |
| 91-1728 | Dickson Collection | 0.16273 | 3.34493 |
| 91-1748 | Dickson Collection | 0.17163 | 3.08966 |

TABLE V-continued

Validation Data for SNP 13 showing KASP Assay Results for FAM-labeled forward primer and HEX-labeled forward primer plotted in FIG. 22.

| Line | Source | X Axis | Y Axis |
|---|---|---|---|
| 91-1750 | Dickson Collection | 0.16161 | 3.6146 |
| 91-1755 | Dickson Collection | 0.1699 | 2.98614 |
| 91-1759 | Dickson Collection | 0.15516 | 2.86673 |
| 91-1768 | Dickson Collection | 0.16916 | 3.02308 |
| 91-1976 | Dickson Collection | 0.1652 | 3.03809 |
| 91-2100 | Dickson Collection | 0.17726 | 2.83823 |
| 91-3346 | Dickson Collection | 0.17767 | 3.60114 |
| 91-3915 | Dickson Collection | 0.15755 | 3.06934 |
| 91-3918 | Dickson Collection | 0.1931 | 3.70302 |
| 91-3921 | Dickson Collection | 0.17772 | 3.39293 |
| Acclaim | Seminis | 3.17649 | 0.36004 |
| Aunt Ada | Turtle Tree Seed | 2.96191 | 0.37548 |
| B-1 | SerinXOregon5630 cross, F6 | 2.92444 | 0.37348 |
| B-15 | SerinXOregon5630 cross, F6 | 2.97164 | 0.33928 |
| B-28 | SerinXOregon5630 cross, F6 | 3.32621 | 0.34471 |
| B-36 | SerinXOregon5630 cross, F6 | 2.90168 | 0.34392 |
| B-37 | SerinXOregon5630 cross, F6 | 2.95565 | 0.33864 |
| B-38 | SerinXOregon5630 cross, F6 | 3.14711 | 0.35636 |
| B-41 | SerinXOregon5630 cross, F6 | 3.02356 | 0.32217 |
| B-42 | SerinXOregon5630 cross, F6 | 3.21701 | 0.48128 |
| BBL274 | Seminis | 3.02105 | 0.35681 |
| Benchmark | Syngenta | 3.23229 | 0.35855 |
| Booster | Syngenta | 3.28359 | 0.41183 |
| Calgreen | Syngenta | 3.25326 | 0.39753 |
| Castano | Syngenta | 3.02685 | 0.40919 |
| Coloma | Syngenta | 0.18002 | 2.98312 |
| Control 1 | No template controls | 0.19892 | 0.4191 |
| Control 2 | No template controls | 0.19986 | 0.3771 |
| Cosse Violette | Amishland Heirloom Seeds | 0.14402 | 2.6688 |
| Cyclone | Seminis | 3.04205 | 0.36791 |
| Flavor Sweet | Harris Moran | 3.04627 | 0.32019 |
| FM1 Pole Blue | USDA collection: Ferry-Morse | 2.93494 | 0.36738 |
| Fortex | Oregon State University | 3.2798 | 0.47279 |
| Hidatsa Shield | Seed Savers Exchange | 2.87072 | 0.27742 |
| Kentucky Wonder | Syngenta | 3.12825 | 0.39701 |
| Mercury | Syngenta | 2.70235 | 0.30458 |
| New Mex Cave | Peace Seedlings | 0.1491 | 2.99625 |
| PHA0008 | Misión Biológica de Galicia - CSIC | 2.86092 | 0.33557 |
| PHA0112 | Misión Biológica de Galicia - CSIC | 2.92541 | 0.36835 |
| PHA0192 | Misión Biológica de Galicia - CSIC | 2.95004 | 0.3512 |
| PHA0315 | Misión Biológica de Galicia - CSIC | 3.05227 | 0.32702 |
| Swiss Landfrauen | Amishland Heirloom Seeds | 2.96679 | 0.42883 |

Methods for Marker Assisted Identification and Selection of Common Bean Plants

Figure 2:
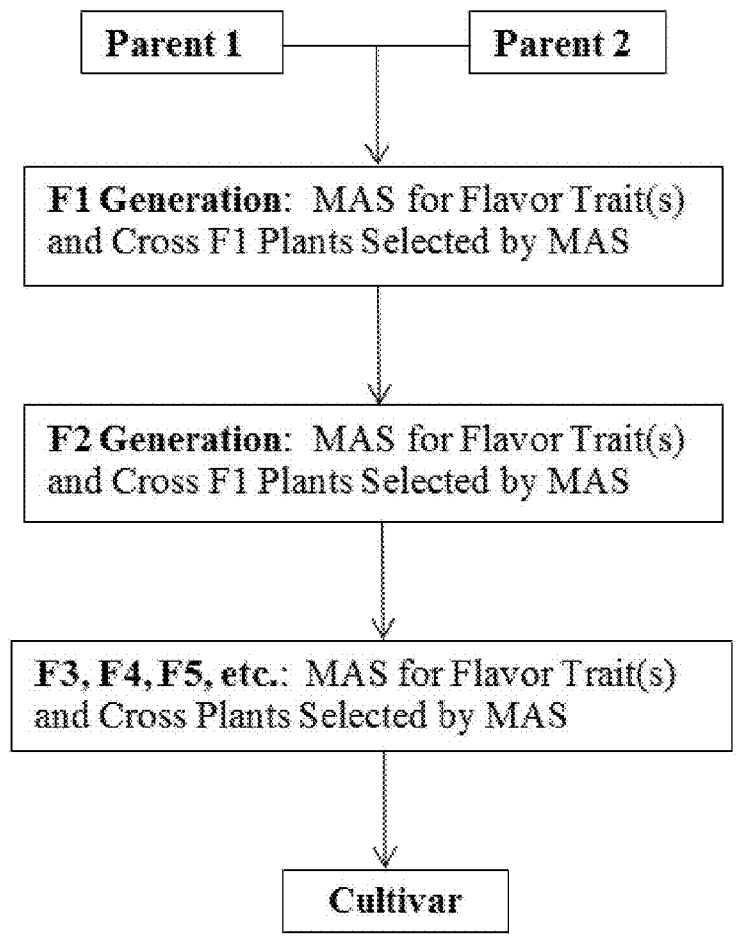
FIG. 2 is a flow chart illustrating methods of the molecular marker selection used in the development of pureline expression of certain volatile compounds in a common bean plant.

Generally, and in reference to FIGS. 1 and 2, the invention includes methods for marker assisted identification and selection of common bean plants with desired flavor traits associated with any one or more of the following volatile compounds: linalool, 1-octen-3-ol, 1-hexanol, 1-penten-3-ol, 1-penten-3-ol, and β-ionone, as well as any combination of two or more of the foregoing volatile compounds. The methods also include marker assisted identification and selection of common bean plants with desired flavor traits that do not express any one or more of linalool, 1-octen-3-ol, 1-hexanol, 1-penten-3-ol, 1-penten-3-ol, and β-ionone, for the purposes of introgressing genes, which are associated with the expression of volatile compounds related to flavor traits known in certain common beans, into other common beans that may not express the desired volatile compound expression, but some other favorable trait, such as high yield.

For example, the methods could be used for selecting plants having desired flavor traits from expressing any one or more of linalool, 1-octen-3-ol, 1-hexanol, 1-penten-3-ol, 1-penten-3-ol, and β-ionone, and then breeding those plants having other favorable traits, such as, upright bush habit (e.g., as expressed by Huntington, Pismo), high percentage of snipped pods (e.g., as expressed by Caprice, Nadia, Cabot), mouth appeal with firm pod texture (e.g., as expressed by Camaro, Tahoe), aphanomyces root rot resistance (e.g., as expressed by BA 1001, SV1136GF), bacteria brown spot blight resistance (e.g., as expressed by Crockett, Hystyle, Caprice), enhanced blue lake flavor (e.g., as expressed by EZ-Pick, FM1 Pole, and OSU 5402), or high yield (e.g., as expressed by Huntington and Pismo) for introgressing the flavor traits into bean lines having other favorable traits.

Marker Assisted Identification and Selection Using SNP 1, SNP 2, and/or SNP 3

Embodiments of the invention includes methods for producing a common bean plant phenotypically expressing at least the following volatile compound, namely, 3-hexen-1-ol, the method comprising the steps of: (1) screening a population of common bean plants for at least one of the following SNPs: SNP 1, which comprises a T to G nucleotide at position number 32 in SEQ ID NO: 1 or at position number 2939690 of Chromosome 1; SNP 2, which comprises a G to A nucleotide pair at position number 33 in SEQ ID NO: 2 or at position number 53768383 of Chromosome 8; and SNP 3, which comprises an A or G nucleotide pair at position number 26 in SEQ ID NO: 3 or at position number 14800672 of Chromosome 6; (2) selecting a first common bean plant having at least one SNP 1 through SNP 3; (3) crossing the first selected common bean plant having at least one of SNP 1 through SNP 3 with a second common bean plant having at least one of SNP 1 through SNP 3; (4) repeating steps (2) and (3) to obtain common bean plants homozygous for at least one of SNP 1 through SNP 3; and (5) screening the common bean plants to confirm the presence of at least one of SNP 1 through SNP 3 in homozygous form to produce a common bean plant, wherein the seeds of the common bean plant have phenotypic expression of 3-hexen-1-ol.

In an embodiment, the method involves stacking or pyramiding the SNPs for 3-hexen-1-ol, i.e., SNP 1, SNP 2, SNP 3, such that more than one desirable SNP is homozygous in a bean plant.

In further embodiments, the method involves stacking or pyramiding the beneficial SNPs for 3-hexen-1-ol, i.e., SNP 1, SNP 2, SNP 3, in combination with other SNPs, e.g., SNP 4, SNP 5, and/or SNP 6 for 1-octen-3-ol; SNP 7 for linalool; SNP 8 and/or SNP 9 for 1-penten-3-ol; SNP 10 and/or SNP 11 for 1-hexanol; and/or SNP 12 and/or SNP 13 for β-ionone, such that a bean plant is homozygous for SNPs associated with two or more volatile compounds selected from the group consisting of: 3-hexen-1-ol, 1-octen-3-ol, linalool, 1-penten-3-ol, 1-hexanol, and β-ionone. In a non-limiting example, stacking or pyramiding can be used to breed a bean plant that is homozygous for SNPs for 3-hexen-1-ol, i.e., SNP 1, SNP 2, and/or SNP 3, and for SNPs for 1-octen-3-ol, i.e., SNP 4, SNP 5, and SNP 6. Other combinations of homozygous expression of two or more SNPs specific to the volatile compounds can occur using stacking or pyramiding.

Marker Assisted Identification and Selection Using SNP 4, SNP 5, and/or SNP 6

An embodiment of the invention includes a method for producing a common bean plant phenotypically expressing at least the following volatile compound, namely, 1-octen-3-ol, the method comprising the steps of: (1) screening a population of common bean plants for at least one of the following SNPS: SNP 4, which comprises a T or C nucleotide pair at position number 28 in SEQ ID NO: 4 or at position number 47396341 of Chromosome 2; SNP 5, which comprises a C or A nucleotide pair at position number 27 in SEQ ID NO: 5 or at position number 19725396 of Chromosome 2; and SNP 6, which comprises a T or G nucleotide pair at position number 32 in SEQ ID NO: 6 or at position number 39538212 of Chromosome 7; (2) selecting a first common bean plant having at least one of SNP 4 through SNP 6; (3) crossing the first selected common bean plant having at least one of SNP 4 through SNP 6 with a second common bean plant having at least one of SNP 4 through SNP 6; (4) repeating steps (2) and (3) to obtain common bean plants homozygous for at least one of SNP 4 through SNP 6; and (5) screening the common bean plants to confirm the presence of at least one of SNP 4 through SNP 6 in homozygous form to produce a common bean plant, wherein the seeds of the common bean plant have phenotypic expression of 1-octen-3-ol.

In an embodiment, the method involves stacking or pyramiding the beneficial SNPs for 1-octen-3-ol, i.e., SNP 4, SNP 5, SNP 6, such that more than one desirable SNP was homozygous in a bean plant.

In further embodiments, the method involves stacking or pyramiding the beneficial SNPs for 1-octen-3-ol, i.e., SNP 4, SNP 5, and/or SNP 6, in combination with other SNPs, e.g., SNP 1, SNP 2, and/or SNP 3 for 3-hexen-1-ol; SNP 7; SNP 8 and/or SNP 9 for 1-penten-3-ol; SNP 10 and/or SNP 11 for 1-hexanol; and/or SNP 12 and/or SNP 13 for beta ionone, such that a bean plant is homozygous for SNPs associated with two or more volatile compounds selected from the group consisting of: 3-hexen-1-ol, 1-octen-3-ol, linalool, 1-penten-3-ol, 1-hexanol, and β-ionone. In a non-limiting example, stacking or pyramiding can be used to breed a bean plant that is homozygous for SNPs for 1-octen-3-ol, i.e., SNP 4, SNP 5, and/or SNP 6, and for SNPs for 3-hexen-1-ol, i.e., SNP 1, SNP 2, and SNP 3. Other combinations of homozygous expression of two or more SNPs specific to the volatile compounds can occur using stacking or pyramiding.

Marker Assisted Identification and Selection Using SNP 7

An embodiment of the invention includes a method for producing a common bean plant phenotypically expressing at least the following volatile compound, namely, linalool, the method comprising the steps of: (1) screening a population of common bean plants for SNP 7, which comprises a G or T nucleotide pair at position number 30 in SEQ ID NO: 7 or at position number 32623478 of Chromosome 7; (2) selecting a first common bean plant having SNP 7; (3) crossing the first selected common bean plant having SNP 7 with a second common bean plant having SNP 7; (4) repeating steps (2) and (3) to obtain common bean plants homozygous for SNP 7; and (5) screening the common bean plants to confirm the presence of SNP 7 in homozygous form to produce a common bean plant, wherein the seeds of the common bean plant have phenotypic expression of linalool.

In an embodiment, the method involves stacking or pyramiding the beneficial SNP for linalool, i.e., SNP 7, in combination with other SNPs, e.g., SNP 1, SNP 2, and/or SNP 3 for 3-hexen-1-ol; SNP 4, SNP 5, and/or SNP 6 for 1-octen-3-ol; SNP 7; SNP 8 and/or SNP 9 1-penten-3-ol; SNP 10 and/or SNP 11 for 1-hexanol; and/or SNP 12 and/or SNP 13 for β-ionone, such that a bean plant is homozygous for SNPs associated with two or more volatile compounds selected from the group consisting of: 3-hexen-1-ol, 1-octen-3-ol, linalool, 1-penten-3-ol, 1-hexanol, and β-ionone. In a non-limiting example, stacking or pyramiding can be used to breed a bean plant that expresses SNP 7 and is also homozygous for SNPs for 1-octen-3-ol, i.e., SNP 4, SNP 5, and/or SNP 6. Other combinations of expression of SNP 7 with homozygous expression of two or more SNPs specific to the volatile compounds can occur using stacking or pyramiding.

Marker Assisted Identification and Selection Using SNP 8 and/or SNP 9

An embodiment of the invention includes a method for producing a common bean plant phenotypically expressing at least the following volatile compound, namely, 1-penten-3-ol, the method comprising the steps of: (1) screening a population of common bean plants for at least one of the following SNPS: SNP 8, which comprises a G or A nucleotide pair at position number 29 in SEQ ID NO: 8 or at position number 44170119 of Chromosome 3; and SNP 9, which comprises an A or G nucleotide pair at position number 24 in SEQ ID NO: 9 or at position number 32906019 of Chromosome 3; (2) selecting a first common bean plant having at least one of SNP 8 and SNP 9; (3) crossing the first selected common bean plant having at least one of SNP 8 and SNP 9 with a second common bean plant having at least one of SNP 8 and SNP 9; (4) repeating steps (2) and (3) to obtain common bean plants homozygous for at least one of SNP 8 and SNP 9; and (5) screening the common bean plants to confirm the presence of at least one of SNP 8 and SNP 9 in homozygous form to produce a common bean plant, wherein the seeds of the common bean plant have phenotypic expression of 1-penten-3-ol.

In an embodiment, the method involves stacking or pyramiding the beneficial SNPs for 1-penten-3-ol, i.e., SNP 8 and SNP 9, such that more than one desirable SNP is homozygous in a bean plant.

In a further embodiment, the method involves stacking or pyramiding the beneficial SNPs for 1-penten-3-ol, i.e., SNP 8 and SNP 9, in combination with other SNPs, e.g., SNP 1, SNP 2, and/or SNP 3 for 3-hexen-1-ol; SNP 7 for linalool; SNP 8 and/or SNP 9 for 1-penten-3-ol; SNP 10 and/or SNP 11 for 1-hexanol; and/or SNP 12 and/or SNP 13 for β-ionone, such that a bean plant is homozygous for SNPs associated with two or more volatile compounds selected from the group consisting of: 3-hexen-1-ol, 1-octen-3-ol, linalool, 1-penten-3-ol, 1-hexanol, and β-ionone. In a non-limiting example, stacking or pyramiding can be used to breed a bean plant that is homozygous for SNPs for 1-penten-3-ol, i.e., SNP 8 and SNP 9, and for SNPs for 3-hexen-1-ol, i.e., SNP 1, SNP 2, and SNP 3. Other combinations of homozygous expression of SNPs specific to two or more volatile compounds can occur using stacking or pyramiding.

Marker Assisted Identification and Selection Using SNP 10 and/or SNP 11

An embodiment of the invention includes a method for producing a common bean plant phenotypically expressing at least the following volatile compound, namely, 1-hexanol, the method comprising the steps of: (1) screening a population of common bean plants for at least one of the following SNPS: SNP 10, which comprises an A or G nucleotide pair at position number 23 in SEQ ID NO: 10 or at position number 54970429 of Chromosome 8; and SNP 11, which comprises a T or C nucleotide pair at position number 29 in SEQ ID NO: 11 or at position number 51964707 of Chromosome 11; (2) selecting a first common bean plant having at least one of SNP 10 and SNP 11; (3) crossing the first selected common bean plant having at least one of SNP 10 and SNP 11 with a second common bean plant having at least one of SNP 10 and SNP 11; (4) repeating steps (2) and (3) to obtain common bean plants homozygous for at least one of SNP 10 and SNP 11; and (5) screening the common bean plants to confirm the presence of at least one of SNP 10 and SNP 11 in homozygous form to produce a common bean plant, wherein the seeds of the common bean plant have phenotypic expression of 1-hexanol.

In an embodiment, the method involves stacking or pyramiding the beneficial SNPs for 1-hexanol, i.e., SNP 10 and SNP 11, such that more than one desirable SNP is homozygous in a bean plant.

In a further embodiment, the method involves stacking or pyramiding the beneficial SNPs for 1-hexanol, i.e., SNP 10 and SNP 11, in combination with other SNPs, e.g., SNP 1, SNP 2, and/or SNP 3 for 3-hexen-1-ol; SNP 4, SNP 5, and/SNP 6 for 1-octen-3-ol; SNP 7; SNP 8 and/or SNP 9 for 1-penten-3-ol; SNP 10 and/or SNP 11 for 1-hexanol; and/or SNP 12 and/or SNP 13 for β-ionone, such that a bean plant is homozygous for SNPs associated with two or more volatile compounds selected from the group consisting of: 3-hexen-1-ol, 1-octen-3-ol, linalool, 1-penten-3-ol, 1-hexanol, and β-ionone. Other combinations of homozygous expression of SNPs specific to two or more volatile compounds can occur using stacking or pyramiding.

Marker Assisted Identification and Selection Using SNP 12 and/or SNP 13

An embodiment of the invention includes a method for producing a common bean plant phenotypically expressing at least the following volatile compound, namely, β-ionone, the method comprising the steps of: (1) screening a population of common bean plants for at least one of the following SNPS: SNP 12, which comprises a T or G nucleotide pair at position number 32 in SEQ ID NO: 12 or at position number 729615 of Chromosome 2; and SNP 13, which comprises a C or A nucleotide pair at position number 25 in SEQ ID NO: 13 or at position number 18092182 of Chromosome 7; (2) selecting a first common bean plant having at least one of SNP 12 and SNP 13; (3) crossing the first selected common bean plant having at least one of SNP 12 and SNP 13 with a second common bean plant having at least one of SNP 12 and SNP 13; (4) repeating steps (2) and (3) to obtain common bean plants homozygous for at least one of SNP 12 and SNP 13; and (5) screening the common bean plants to confirm the presence of at least one of SNP 12 and SNP 13 in homozygous form to produce a common bean plant, wherein the seeds of the common bean plant have phenotypic expression of β-ionone.

In an embodiment, the method involves stacking or pyramiding the beneficial SNPs for beta ionone, i.e., SNP 12 and SNP 13, such that more than one desirable SNP is homozygous in a bean plant.

In a further embodiment, the method involves stacking or pyramiding the beneficial SNPs for β-ionone, i.e., SNP 12 and SNP 13, in combination with other SNPs, e.g., SNP 1, SNP 2, and/or SNP 3 for 3-hexen-1-ol; SNP 4, SNP 5, and/SNP 6 for 1-octen-3-ol; SNP 7 for linalool; SNP 8 and/or SNP 9 for 1-penten-3-ol; and/or SNP 10 and/or SNP 11 for 1-hexanol, such that a bean plant is homozygous for SNPs associated with two or more volatile compounds selected from the group consisting of: 3-hexen-1-ol, 1-octen-3-ol, linalool, 1-penten-3-ol, 1-hexanol, and β-ionone. Other combinations of homozygous expression of SNPs specific to two or more volatile compounds can occur using stacking or pyramiding.

The invention provides common bean plants containing up to 13 SNP markers, i.e., SNP 1 through SNP 13, in homozygous form. The invention describes common bean plants containing three SNPs, i.e., SNP 1 through SNP 3, that are shown to be associated with the phenotypic expression of the volatile compound 3-hexen-1-ol, three SNPs, i.e., SNP 4 through SNP 6, that are shown to be associated with the phenotypic expression of the volatile compound 1-octen-3-ol, one SNP, i.e., SNP 7, that is shown to be associated with the phenotypic expression of the volatile compound linalool, two SNPs, i.e., SNP 8 and SNP 9, that are shown to be associated with the phenotypic expression of the volatile compound 1-penten-3-ol, two SNPs, i.e., SNP 10 and SNP 11, that are shown to be associated with the phenotypic expression of the volatile compound 1-hexanol, and two SNPs, i.e., SNP 12 and SNP 13, that are shown to be associated with the phenotypic expression of the volatile compound β-ionone.

Embodiments also provide methods for screening common bean plants containing any one or more of the 13 SNPs, as well as methods and steps for using these SNPs in marker assisted breeding to produce common bean plants phenotypically expressing at least one or more of 3-hexen-1-ol, 1-octen-3-ol, linalool, 1-penten-3-ol, 1-hexanol, and/or β-ionone, or plants phenotypically expressing at least two or more of 3-hexen-1-ol, 1-octen-3-ol, linalool, 1-penten-3-ol, 1-hexanol, and/or β-ionone, or plants phenotypically expressing at least three or more of 3-hexen-1-ol, 1-octen-3-ol, linalool, 1-penten-3-ol, 1-hexanol, and/or β-ionone, or plants phenotypically expressing at least four or more of 3-hexen-1-ol, 1-octen-3-ol, linalool, 1-penten-3-ol, 1-hexanol, and/or β-ionone, or plants phenotypically expressing at least five or more of 3-hexen-1-ol, 1-octen-3-ol, linalool, 1-penten-3-ol, 1-hexanol, and/or β-ionone, or plants phenotypically expressing 3-hexen-1-ol, 1-octen-3-ol, linalool, 1-penten-3-ol, 1-hexanol, and β-ionone.

Also provided with the invention are methods for introgressing at least one of, at least two of, or all three SNPs associated with 3-hexen-1-ol, i.e., SNP 1, SNP 2, and SNP 3, into common bean plants by selecting plants comprising for one or more of the SNPs and breeding with such plants to confer such desirable phenotypes to plant progeny.

Also provided with the invention are methods for introgressing at least one of, at least two of, or all three SNPs associated with 1-octen-3-ol, i.e., SNP 4, SNP 5, and SNP 6, into common bean plants by selecting plants comprising for one or more of the SNPs and breeding with such plants to confer such desirable phenotypes to plant progeny.

Also provided with the invention are methods for introgressing at SNP associated with linalool, i.e., SNP 7, into common bean plants by selecting plants comprising SNP 7 and breeding with such plants to confer such desirable phenotypes to plant progeny.

Also provided with the invention are methods for introgressing at least one of, or both SNPs associated with 1-penten-3-ol, i.e., SNP 8 and SNP 9, into common bean plants by selecting plants comprising for one or more of the SNPs and breeding with such plants to confer such desirable phenotypes to plant progeny.

Also provided with the invention are methods for introgressing at least one of, or both SNPs associated with 1-hexanol, i.e., SNP 10 and SNP 11, into common bean plants by selecting plants comprising for one or more of the SNPs and breeding with such plants to confer such desirable phenotypes to plant progeny.

Also provided with the invention are methods for introgressing at least one of, or both SNPs associated with β-ionone, i.e., SNP 12 and SNP 13, into common bean plants by selecting plants comprising for one or more of the SNPs and breeding with such plants to confer such desirable phenotypes to plant progeny.

Accordingly, the KASP primers of the present invention can be used for analyzing genetic and phenotypic relationships within common bean lines including linkage analysis, association mapping, and the like; calculating the genetic distance between varieties of the common bean lines; identifying identical or related plants; evaluating the purity of varieties; identifying hybrids; breeding; selecting qualitative traits; selecting the genome of a recurrent parent and against the markers of the donor parent; reducing the number of crosses and/or backcrosses in a breeding program; identifying, and including or excluding, certain sources of germplasm of parental varieties or ancestors of a plant by tracking genetic profiles through crosses and into progeny; and the development of new common bean varieties, seed cultivation, and evaluating new innovation in common bean breeding (to produce seeds and planting material). The information gained from these markers can be used to determine if a plant carries a trait of interest, or if a plant is sufficiently similar or sufficiently different for breeding purposes, and selection of optimal plants for breeding, predicting plant traits and generation of distinct cultivars.

Other Molecular Assays that could Target SNP 1 Through SNP 13 Using the Oligos in the KASP Primers A molecular assay that can be used as an alternative to the KASP assay, while using the oligo sequences of the competitive KASP primers, include methods that directly target the SNP marker, such as Cleaved Amplified Polymorphic Sequences (CAPS). Another alternative molecular assay called PCR-sequence specific amplification (SSP). PCR-SSP is simply a form of polymerase chain reaction (PCR) that involves using primers that are based on one or more of the oligos of the competitive KASP primers so that the primers will or will not allow amplification (the 3'-mismatch principle). One would set up separate reactions for the alternative forms of the primer that end in different SNP. This would not be a competitive reaction and only the correct primer should amplify and alternative primers should fail to amplify the DNA. The output from the assay would be either (1) it amplified, or (2) it did not amplify (see, Rev Immunogenet. 1999; 1(2):157-76).

While the invention has been described in conjunction with specific embodiments, it is evident that many alternatives, modifications, permutations, and variations will become apparent to those skilled in the art, in light of the foregoing description. Accordingly, it is intended that the present invention embraces all such alternatives, modifications, and variations as falling within the scope of the claims below.

What is claimed is:

1. A method for producing a common bean plant with enhanced flavor traits, the enhanced flavor traits comprising phenotypic expression of a volatile compound comprising 1-penten-3-ol, the method comprising,
   providing a first common bean plant having a single nucleotide polymorphism (SNP) identified as SNP 9 having an A or G nucleotide at a position that corresponds to position 24 of SEQ ID NO. 9;
   providing a second common bean plant that does not have a single nucleotide polymorphism (SNP) that corresponds with expression by the first common bean plant of SNP 9;
   crossing the first common bean plant with the second common bean plant to produce an F1 generation; and
   identifying one or more members of the F1 generation for a presence of SNP 9.

2. The method of claim 1 further comprising selecting a first F1 generation plant and a second F1 generation plant based on the presence of SNP 9, crossing the first F1 generation plant and the second F1 generation plant, and then identifying the presence of SNP 9 in one or more members of a F2 generation.

3. The method of claim 2 further comprising selecting members of the F2 generation based on the presence of SNP 9 for growth of pedigrees selected for the presence of SNP 9.

4. The method of claim 2 wherein SNP 9 is associated with phenotypic expression of 1-penten-3-ol in the first common bean plant, in the members of the F1 generation having SNP 9, and in the members of the F2 generation having SNP 9.

5. The method of claim 4 wherein identifying expression of volatile compound 1-penten-3-ol comprises using a pair of PCR Primers comprising SEQ ID NO: 51 and SEQ ID NO: 52 configured to identify SNP 9.

6. A method for introgressing a gene associated with phenotypic expression of flavor traits of 1-penten-3-ol expressed in a common bean plant, the method comprising:
   screening a population of common bean plants for the presence of SNP 9 with a PCR reaction or a modified PCR reaction with KASP primers, the PCR reaction or modified PCR reaction comprising a primer pair comprising SEQ ID NO: 51 and SEQ ID NO: 52 configured to identify SNP 9;
   selecting from the population a first common bean plant having SNP 9 associated with the desired flavor traits of 1-penten-3-ol;
   crossing the first common bean plant with a second common bean plant that may or may not have SNP 9;
   repeating the steps of selecting and crossing to obtain a progeny common bean plant homozygous for SNP 9; and
   screening the progeny to confirm presence of SNP 9 in homozygous form to produce a common bean seed.

* * * * *